(12) United States Patent
Liou et al.

(10) Patent No.: US 11,479,528 B2
(45) Date of Patent: Oct. 25, 2022

(54) HEAT SHOCK PROTEIN 90 INHIBITORS

(71) Applicant: TAIPEI MEDICAL UNIVERSITY, Taipei (TW)

(72) Inventors: Jing-ping Liou, Taipei (TW); Che-ming Teng, Taipei (TW); Shiow-lin Pan, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 16/496,355

(22) PCT Filed: Mar. 20, 2018

(86) PCT No.: PCT/CN2018/079563
§ 371 (c)(1),
(2) Date: Sep. 20, 2019

(87) PCT Pub. No.: WO2018/171575
PCT Pub. Date: Sep. 27, 2018

(65) Prior Publication Data
US 2020/0039923 A1   Feb. 6, 2020

Related U.S. Application Data

(60) Provisional application No. 62/473,708, filed on Mar. 20, 2017.

(51) Int. Cl.
| | |
|---|---|
| C07C 235/60 | (2006.01) |
| C07C 49/835 | (2006.01) |
| A61K 9/00 | (2006.01) |
| C07D 295/135 | (2006.01) |
| C07D 295/192 | (2006.01) |
| C07D 213/75 | (2006.01) |
| C07D 209/08 | (2006.01) |
| C07D 471/04 | (2006.01) |
| C07D 231/56 | (2006.01) |
| C07D 487/04 | (2006.01) |
| C07D 215/38 | (2006.01) |
| C07D 261/20 | (2006.01) |
| C07C 233/75 | (2006.01) |
| C07C 311/21 | (2006.01) |
| C07C 39/15 | (2006.01) |
| A61P 35/00 | (2006.01) |

(52) U.S. Cl.
CPC .......... *C07C 235/60* (2013.01); *A61K 9/0053* (2013.01); *A61P 35/00* (2018.01); *C07C 39/15* (2013.01); *C07C 49/835* (2013.01); *C07C 233/75* (2013.01); *C07C 311/21* (2013.01); *C07D 209/08* (2013.01); *C07D 213/75* (2013.01); *C07D 215/38* (2013.01); *C07D 231/56* (2013.01); *C07D 261/20* (2013.01); *C07D 295/135* (2013.01); *C07D 295/192* (2013.01); *C07D 471/04* (2013.01); *C07D 487/04* (2013.01)

(58) Field of Classification Search
CPC ... C07C 235/60; C07C 49/835; C07C 233/75; C07C 311/21; C07C 39/15; A61K 9/0053; A61P 35/00; C07D 295/135; C07D 295/197; C07D 213/75; C07D 209/08; C07D 471/04; C07D 231/56; C07D 487/04; C07D 215/38; C07D 261/20
USPC ........................................................ 546/304
See application file for complete search history.

(56) References Cited

U.S. PATENT DOCUMENTS

2007/0259886 A1*  11/2007  Chessari .............. C07D 209/44
                                                       514/254.09

FOREIGN PATENT DOCUMENTS

| EP | 1512396 A1 | 3/2005 |
|---|---|---|
| WO | 2001044172 A1 | 6/2001 |
| WO | 2006109085 A1 | 10/2006 |
| WO | 2006117669 A1 | 11/2006 |
| WO | 2008044027 A2 | 4/2008 |
| WO | 2009066060 A2 | 5/2009 |
| WO | 2015040425 A1 | 3/2015 |

OTHER PUBLICATIONS

Goel et al, Synthesis, optical resolution, absolute configuration, and osteogenic activity of cis-pterocarpans, Organic & Bimolecular Chemistry, 2012, 10, p. 9583-9592 (Year: 2012).*

Al-Asril et al , From carbohydrates to drug-like fragments: Rational development of novel a-amylase inhibitors, Bioorganic & Medicinal Chemistry, 23, 2015, p. 6725-6732 (Year: 2015).*

(Continued)

*Primary Examiner* — Taylor V Oh
(74) *Attorney, Agent, or Firm* — Duane Morris LLP

(57) ABSTRACT

This disclosure is related to aromatic compounds of formula (I), and methods of their use in treating medical conditions associated with Heat Shock Protein-90 (HSP90), e.g., cancer. Compounds of formula (I) have the following structure:

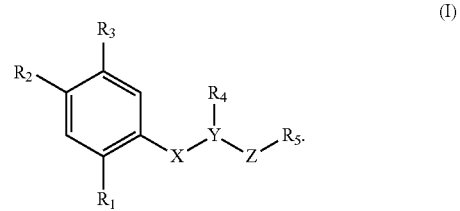

Also disclosed are pharmaceutical compositions comprising compounds of formula (I).

19 Claims, No Drawings

(56) References Cited

OTHER PUBLICATIONS

Shokol et al , Reaction of the α-azahetaryl-2-hydroxyacetophenones with chloroacetyl chlorideFrench-Ukrainian Journal of Chemistry, 2013, 1(1), 10-14). (Year: 2013).*
Giacomini et al, A Ligand-Based Virtual Screening Approach to Identify Small Molecules as hERG Channel Activators, Combinational Chemistry & High throughput Screening, 2015, 18(3), p. 169-280) . . . (Year: 2015).*
Frasinyuk et al ,Cyclic Carboxylic Anhydrides as New Reagents for Formation of Chromone Ring, Journal of Heterocycle Chem., 2014, 51, 768-774 (Year: 2014).*
International Search Report in International Patent Application No. PCT/CN2018/079563, dated Jun. 29, 2018, in 2 pages.
Jeong, Ju Hui, et al. "Targeting the entry region of Hsp90's ATP binding pocket with a novel 6, 7-dihydrothieno [3, 2-c] pyridin-5 (4H)-yl amide." European Journal of Medicinal Chemistry 124 (2016): 1069-1080.
Yu, Gui Jun, et al. "Potent s-cis-locked bithiazole correctors of ΔF508 cystic fibrosis transmembrane conductance regulator cellular processing for cystic fibrosis therapy." Journal of Medicinal Chemistry 51.19 (2008): 6044-6054.
Office Action in Taiwan Counterpart Application No. 107109520, dated Nov. 26, 2018, in 10 pages; English translation provided.
George A. Patani et al."Bioisosterism: A Rational Approach in Drug Design." Chemical Reviews. 1996, 96, 3147-3176.
Partial Supplementary European Search Report in EP Application No. 18770931.6 dated Sep. 25, 2020, in 13 pages.
Cikotiene, Inga, et al. "5-AryI-4-(5-substituted-2, 4-dihydroxyphenyl)-1,2, 3-thiadiazoles as inhibitors of Hsp90 chaperone." Bioorganic & Medicinal Chemistry Letters 19.4 (2009): 1089-1092.
Jia, Jian-Min, et al. "Hybrids of the Benzofuran Core from Natural Products and the 2, 4-Dihydroxy-5-isopropylbenzene Fragment as Potent Hsp90 Inhibitors: Design, Synthesis and Bioevaluation." Molecular Informatics 33.8 (2014): 495-502.
Huang, Renjie, et al. "Virtual screening and biophysical studies lead to HSP90 inhibitors." Bioorganic & Medicinal Chemistry Letters 27.2 (2017): 277-281.
Chemical Abstract Compound: "1-(2,4-dihydroxyphenyl)-2-thiazolyl-ethanone derivative", STNNEXT-REGISTRY, Entered STN: Nov. 1, 2000 (Nov. 1, 2000), XP55768181, Chemcats, RN 300 713-67-1.
Chemical Abstract Compound: "1(2,4-dihydroxyphenyl)-2-thiazolyl-ethanone derivative", STNNEXT-REGISTRY, Entered STN: Nov. 2, 2000 (Nov. 2, 2000), XP55768182, Chemcats, RN 300 826-42-0.
Chemical Abstract Compound: "1-(2,4-dihydroxyphenyl)-2-pyridinyl derivative", STNNEXT-REGISTRY, Entered STN: Nov. 2, 2000 (Nov. 2, 2000), XP55768183, Chemcats, RN 300 826-25-9.
Chemical Abstract Compound: "1-(2,4-dihydroxyphenyl)-2-benzimidazolyl-ethanone derivative", STNNEXT-REGISTRY, Entered STN: Nov. 3, 2000 (Nov. 3, 2000), XP55768185, Chemcats, RN 301 159-83-1.
Chemical Abstract Compound: "1-(2,4-dighydroxyphenyl)-2-benzofuranyl-ethanone derivative", STNNEXT-REGISTRY, Entered STN: Jan. 9, 2001 (Jan. 9, 2001), XP55768187, Chemcats, RN 313 253-62-2.
Extended European Search Report in EP Application No. 18770931.6, dated Feb. 3, 2021, in 18 pages.
Office Action in Japan Counterpart Application No. 2019-551970, dated Dec. 7, 2021, in 6 pages; English translation provided.

* cited by examiner

HEAT SHOCK PROTEIN 90 INHIBITORS

This application claims priority to International Patent Application No. PCT/CN2018/079563, filed Mar. 20, 2018, which claims the benefit of U.S. Provisional Application No. 62/473,708, filed on Mar. 20, 2017, both of which are incorporated herein in their entirety by reference.

FIELD

This disclosure relates to the field of treating medical conditions associated with Heat shock protein 90 (HSP90) using compounds of formula (I). In particular, this disclosure relates to treating cancer with compounds of formula (I).

BACKGROUND

Molecular chaperones guide polypeptides to fold correctly so that they lower the risk of protein assembly while exposing to the protein-rich intracellular environment. Heat shock protein 90 (HSP90), a molecular chaperone, functions as a stabilizer and activator of HSP90 client proteins, such as protein kinase B, cyclin-dependent kinase 4, and fms-like tyrosine kinase 3. Certain HSP90 client proteins, crucial in cell growth, are termed oncoproteins.

HSP90 has become an attractive target due to its close connection with numerous client proteins. One of the advantages of inhibiting HSP90 is that the inhibition causes simultaneous shut-down of several oncoproteins. As a result, inhibition of HSP90 leads to gradual degradation of certain oncoproteins and eventually suppresses cancer growth.

Several HSP90 inhibitors have been identified and tested in clinical trials. In general, HSP90 inhibitors are categorized into two groups: natural product and synthetic molecule. Natural HSP90 inhibitors derive from 17-allylamino-17-desmethoxygeldanamycin (17-AAG), of which the structures typically have a symbolic quinone ring fused with a macrocycle ring. Synthetic HSP90 inhibitors are classified as purine derivatives (e.g., BIIBO21 from Biogen Idec and NVP-HSP990 from Novatis), resorcinol derivatives (e.g., NVP-AUY922 from Novatis and AT13387 from Astex), and benzamide derivatives (e.g., SNX-2112 from Pfizer). These HSP90 inhibitors have certain drawbacks, including difficult synthesis, low efficacy, and poor safety margin.

SUMMARY

The present invention is based on an unexpected discovery that certain substituted aromatic compounds effectively inhibit HSP90 with good safety profiles.

In one aspect, this invention relates to substituted aromatic compounds of formula (I):

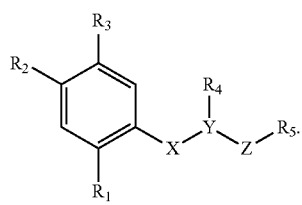

(I)

wherein X is CO, $SO_2$, $CH_2$, $NR_a$, or a bond, $R_a$ being H or $C_{1-6}$ alkyl; Y is N, $CH_2$, CO, $SO_2$, or a bond;

Z is aryl or heteroaryl;
each of $R_1$ and $R_2$, independently, is OH or $NH_2$;
$R_3$ is $C_{1-6}$ alkyl or halogen;
$R_4$ is H, $C_{1-6}$ alkyl, $C_{3-8}$ cycloalkyl, $C_{1-6}$ alkylamine, or $C_{1-6}$ alkylalcohol; and
$R_5$ is $CF_3$, CN, $NO_2$, $NR_6R_7$, —$NHCO(CH_2)_n CONHOH$, —$CONH(CH_2)_n CONHOH$, CONHOH, $CO_2NH_2$, $C_{1-6}$ alkoxyl, $C_{3-10}$ cycloalkyl, $C_{3-10}$ heterocycloalkyl, aryl, or heteroaryl when Z is aryl;
or $R_5$ is H, halogen, $CF_3$, CN, $NO_2$, $NR_6R_7$, —NHCO$(CH_2)_n$CONHOH, —CONH$(CH_2)_n$CONHOH, CONHOH, $CO_2NH_2$, $CH_2NR_6R_7$, $C_{1-6}$ alkyl, $C_{1-6}$ alkoxyl, $C_{3-10}$ cycloalkyl, $C_{3-10}$ heterocycloalkyl, aryl, or heteroaryl when Z is heteroaryl, in which case each of $R_6$ and $R_7$, independently, is H, $C_{1-6}$ alkyl, $C_{1-6}$ alkoxyl, $C_{3-10}$ cycloalkyl, $C_{3-10}$ heterocycloalkyl, aryl, or heteroaryl;
or $R_6$, together with $R_7$ and the nitrogen atom bonded to $R_6$ and $R_7$, is $C_{3-10}$ heterocycloalkyl;
or $R_6$, together with Z and the nitrogen atom bonded to $R_6$ and $R_7$, forms a fused bicycle;
and n is 5 to 7.

The term "alkyl" herein refers to a saturated, linear or branched hydrocarbon moiety, such as —$CH_3$ or branched —$C_3H_7$. The term "cycloalkyl" refers to a non-aromatic, monocyclic, bicyclic, tricyclic, or tetracyclic hydrocarbon moiety, such as cyclohexyl, cyclohexen-3-yl, or adamantyl. The term "alkoxyl" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "heterocycloalkyl" refers to a non-aromatic, monocyclic, bicyclic, tricyclic, or tetracyclic moiety having one or more ring heteroatoms (e.g., N, O, or S), such as 4-tetrahydropyranyl or 4-pyranyl.

The term "aryl" refers to a hydrocarbon moiety having one or more aromatic rings. Examples of aryl include, but are not limited to, phenyl (Ph), phenylene, naphthyl, naphthylene, pyrenyl, anthryl, and phenanthryl.

The term "heteroaryl" refers to a moiety having one or more aromatic rings that contain at least one heteroatom (e.g., N, O, or S). Examples of heteroaryl include, but are not limited to, furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

The term "alkylamine" refers to an alkyl that is substituted with at least one amino group. Examples of alkylamine include aminomethyl and 2-aminoethyl.

The term "alkylalcohol" refers to an alkyl that is substituted with at least one hydroxyl group. Examples of alkylalcohol include hydroxyl methyl and hydroxyl ethyl.

Alkyl, cycloalkyl, alkoxyl, heterocycloalkyl, aryl, heteroaryl, alkylamine, and alkylalcohol mentioned herein include both substituted and unsubstituted moieties, unless specified otherwise. Possible substituents on cycloalkyl, heterocycloalkyl, aryl, and heteroaryl include $C_{1-10}$ alkyl, $C_{2-10}$ alkenyl, $C_{2-10}$ alkynyl, $C_{3-20}$ cycloalkyl, $C_{3-20}$ cycloalkenyl, $C_{1-20}$ heterocycloalkyl, $C_{1-20}$ heterocycloalkenyl, $C_{1-10}$ alkoxy, aryl, aryloxy, heteroaryl, heteroaryloxy, amino, $C_{1-10}$ alkylamino, $C_{1-20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The substituted aromatic compounds described above include the compounds themselves, as well as their salts, prodrugs, and solvates, if applicable. A salt, for example, can be formed between an anion and a positively charged group (e.g., amino) on a substituted aromatic compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a substituted aromatic compound. Suitable cations include sodium ion, potassium ion, magnesium ion, calcium ion, and an ammonium cation such as tetramethylammonium ion. The substituted aromatic compounds also include those salts containing quaternary nitrogen atoms. Examples of prodrugs include esters and other pharmaceutically acceptable derivatives, which, upon administering to a subject, are capable of providing active heterocyclic compounds. A solvate refers to a complex formed between an active substituted aromatic compound and a pharmaceutically acceptable solvent. Examples of a pharmaceutically acceptable solvent include water, ethanol, isopropanol, ethyl acetate, acetic acid, and ethanolamine.

"Pharmaceutically acceptable diluents, carriers and/or excipients" is intended to include substances that are useful in preparing a pharmaceutical composition, may be co-administered with compounds of Formula (I), and analogs of any of the foregoing compounds, while allowing it to perform its intended function, and are generally safe, non-toxic and neither biologically nor otherwise undesirable. Pharmaceutically acceptable diluents, carriers and/or excipients include those suitable for veterinary use as well as human pharmaceutical use. Suitable carriers and/or excipients will be readily appreciated by persons of ordinary skill in the art, having regard to the nature of compounds of Formula (I), and analogs of any of the foregoing compounds. Suitable diluents may include or exclude diluents, carriers and/or excipients include solutions, solvents, dispersion media, delay agents, polymeric and lipidic agents, emulsions and the like. By way of further example, suitable liquid carriers, especially for injectable solutions, include water, aqueous saline solution, aqueous dextrose solution, and the like, with isotonic solutions being preferred for intravenous, intraspinal, and intracisternal administration and vehicles such as liposomes being also especially suitable for administration of agents.

In some embodiments, the substituted aromatic compounds of formula (I) may comprise a non-aromatic double bond and one or more asymmetric centers. Thus, they can occur as racemates or racemic mixtures, single enantiomers, individual diastereomers, diastereomeric mixtures, or cis- or trans-isomeric forms. All such isomeric forms are contemplated.

Another aspect of this invention relates to a method for treating a medical condition associated with HSP90. The method includes administering to a subject in need thereof an effective amount of one or more of the substituted aromatic compounds of formula (I) described above. The medical condition associated with HSP90 can be cancer. Examples of the cancer include breast cancer, non-small cell lung cancer, gastric cancer, lymphoma, and multiple myeloma.

Also within the scope of this invention is a pharmaceutical composition comprising one or more of the above-described substituted aromatic compounds of formula (I). The pharmaceutical composition can be used for treating a medical condition associated with HSP90. An exemplary medical condition associated with HSP90 is cancer.

This invention also features use of one or more of the above-described substituted aromatic compounds of formula (I) for the manufacture of a medicament for treating a medical condition associated with HSP90 (e.g., cancer).

The term "treating" or "treatment" refers to administering one or more of the substituted aromatic compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

Doses, Amounts and Concentrations

As will be appreciated, the dose of compounds of formula (I) administered, the period of administration, and the general administration regime may differ between subjects depending on such variables as the target site to which it is to be delivered, the severity of any symptoms of a subject to be treated, the type of disorder to be treated, size of unit dosage, the mode of administration chosen, and the age, sex and/or general health of a subject and other factors known to those of ordinary skill in the art.

To practice the method of the present invention, a composition having one or more of the above-described substituted aromatic compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

Compositions useful in the invention may comprise any appropriate level of compound of formula (I), and analogs of any of the foregoing compounds, having regard to the dosage form and mode of administration. However, by way of example, compositions of use in the invention may contain from approximately 0.1% to approximately 99% by weight, preferably from approximately 1% to approximately 60% of a compound of formula (I), depending on the method of administration. A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions.

In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The compositions may be formulated in accordance with standard techniques as may be found in such standard references as Gennaro A R: Remington: The Science and Practice of Pharmacy, 20$^{th}$ ed., Lippincott, Williams & Wilkins, 2000, for example.

A nasal aerosol or inhalation composition can be prepared according to techniques well known in the art of pharmaceutical formulation. For example, such a composition can be prepared as a solution in saline, employing any suitable preservative or absorption promoter (e.g., benzyl alcohol) or any solubilizing or dispersing agent (e.g., fluorocarbon).

A composition having one or more of the above-described substituted aromatic compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound of formula (I). In some embodiments, the compositions of this disclosure comprise 1,5-diphenyl-penta-1,4-dien-3-one. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed in detail below are substituted aromatic compounds of formula (I):

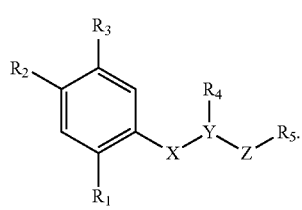
(I)

wherein $R_1$, $R_2$, $R_3$, $R_4$, $R_5$, X, Y, and Z are as described herein.

In one embodiment, this disclosure provides for compounds of formula (I) wherein each of $R_1$ and $R_2$ is OH, and $R_3$ is isopropyl. In some embodiments, X is CO, Y is N, Z is phenyl, and $R_5$ is —NHCO(CH$_2$)$_n$CONHOH or —CONH(CH$_2$)$_n$CONHOH. In some embodiments, Z is

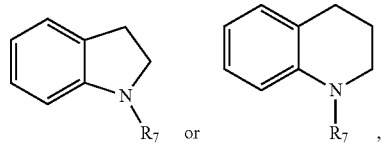

wherein $R_7$ is $C_{1-6}$ alkyl. In some embodiments, Z is heteroaryl, (selected from

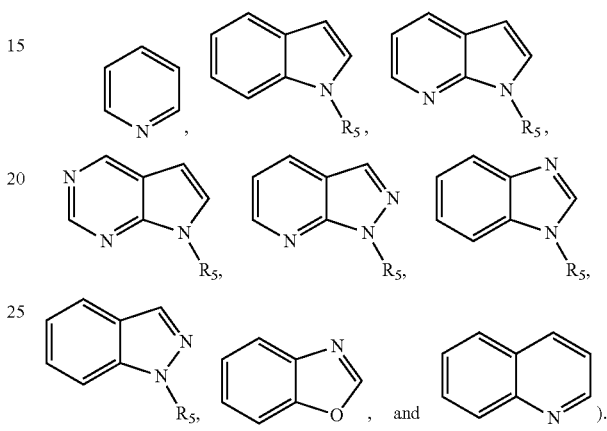

In some embodiments, Z is

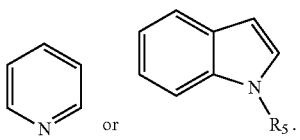

In some preferred embodiments, Z is

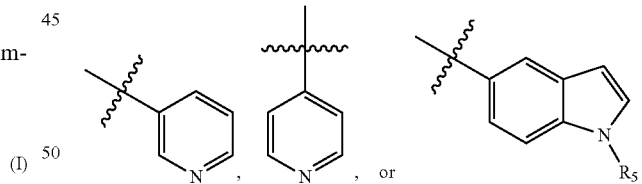

and $R_4$ is $C_{1-6}$ alkyl. Examples of the substituted aromatic compounds in this disclosure can include or exclude the following moieties:

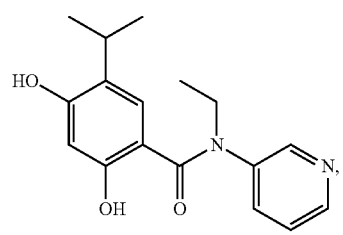 [SMILES: CCN(C(=O)c1cc(C(C)C)c(O)cc1O)c1cccnc1]

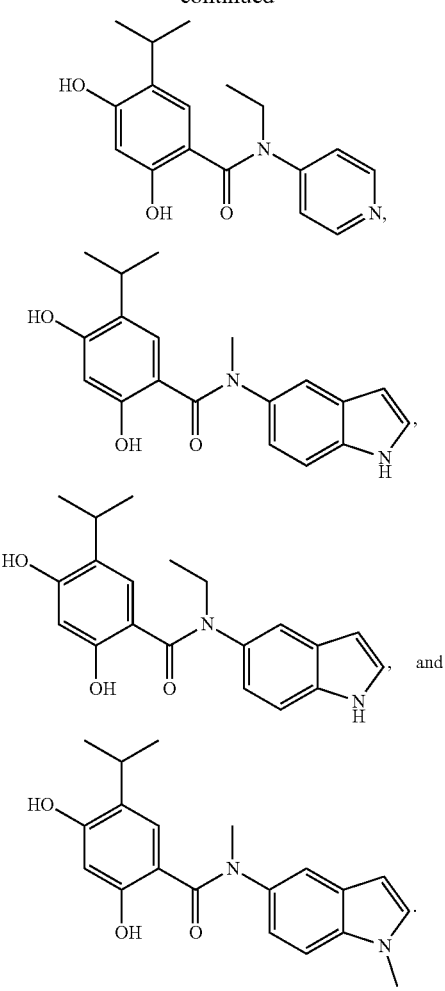

In some embodiments, this disclosure provides for compounds of formula (I) wherein X is CO, Y is N, and Z is

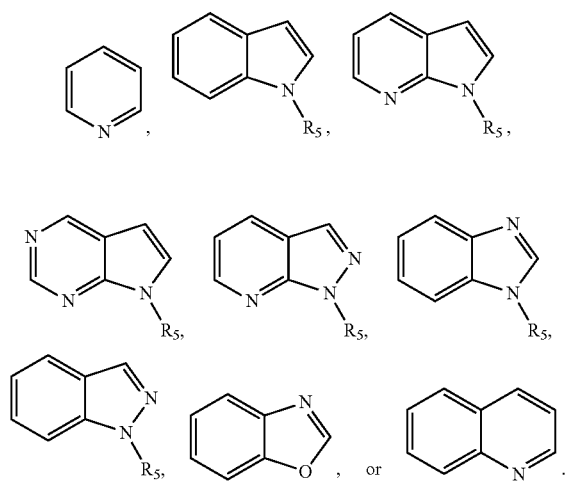

In some embodiments, this disclosure provides for compounds of formula (I) wherein X is CO, $NR_a$, or a bond and Y is CO, $SO_2$, or a bond.

In some embodiments, this disclosure provides for a pharmaceutical composition comprising one or more of the compounds of formula (I) for treating a medical condition associated with HSP90. In some embodiments, the medical condition associated with HSP90 is cancer. In some embodiments, the cancer is selected from breast cancer, non-small cell lung cancer, gastric cancer, lymphoma, or multiple myeloma.

In some embodiments, this disclosure provides for a method for treating a medical condition associated with HSP90, the method including administering to a subject in need thereof an effective amount of a compound of formula (I). The medical condition associated with HSP90 can be breast cancer, non-small cell lung cancer, gastric cancer, lymphoma, or multiple myeloma.

Exemplary compounds of formula (I) used in the above methods include, but are not limited to:

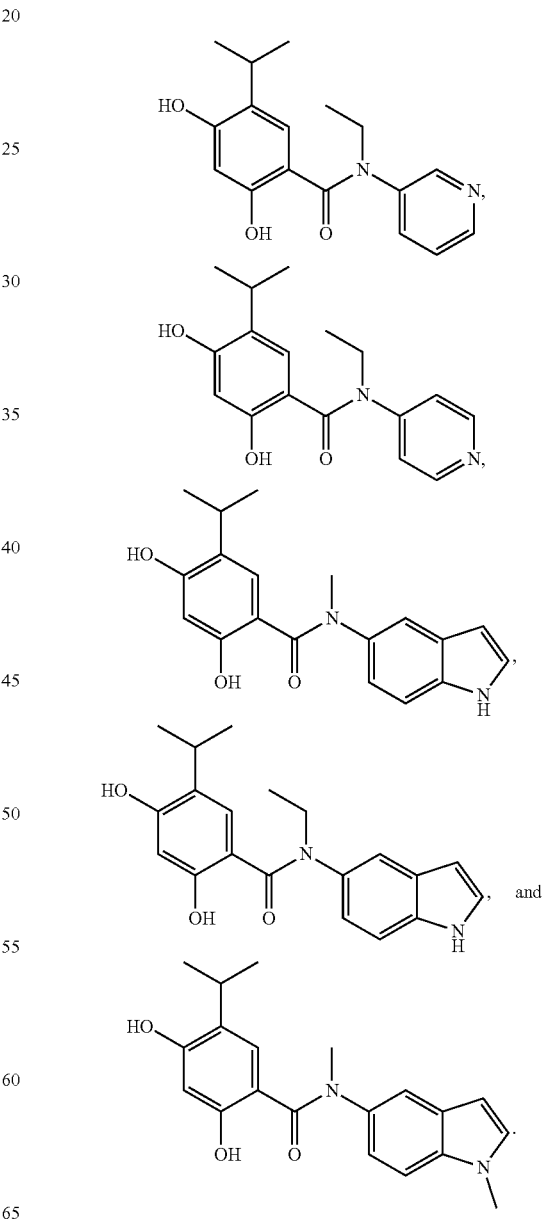

In some embodiments, this disclosure relates to a method of administering the compound

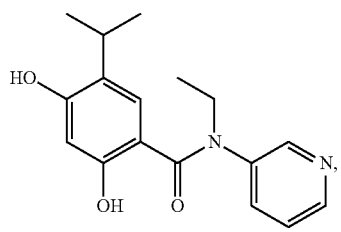

or composition comprising said compound, for treating a medical condition associated with HSP90 (e.g., cancer).

Compounds of formula (I) described above can be prepared according to organic chemistry methods. See, for example, R. Larock, Comprehensive Organic Transformations (2$^{nd}$ Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); and G. J. Yu et al., *J. Med. Chem.* 2008, 51, 6044-6054.

Shown in Scheme A below is a synthetic protocol that can be followed to synthesize substituted aromatic compounds of formula (I). More specifically, a variety of benzoic acids (A) are reacted with amino substituted heterocycles in the presence of coupling reagents such as HBTU, EDC, and DCC to afford corresponding amides (B). Aromatic electrophilic substitution like nitration and formylation are performed by respectively reacting with nitric acid and POCl$_3$/DMF, yielding C and D. Treatment of C with various Grignard reagents followed by oxidation affords benzophenones E. Synthesis of F was fulfilled by the reaction of D with substituted benzoyl chlorides or sulfonyl chlorides. Both E and F are compounds of formula (I).

some embodiments the total impurities, including metabolites of a compound of formula (I), will be not more than 2-12%. In some embodiments the total impurities, including metabolites of a compound of formula (I), will be not more than 3-11%. In other embodiments the total impurities, including metabolites of a compound of formula (I) will be not more than 4-10%.

The compounds of formula (I) thus prepared can be initially screened using in vitro assays, e.g., the radioligand binding assay described in Example 2 below, for their potency in inhibiting binding of SDF-1 to CXCR4. They can be subsequently evaluated using in vivo assays, e.g., a colony-forming assay, for their efficacy in enhancing hematopoietic stem cell mobilization in a mammal. The selected compounds can be further tested to verify their efficacy in treating tissue injury (e.g., acute kidney injury), cancer, inflammatory disease, and autoimmune disease. For example, a compound can be administered to an animal (e.g., a mouse) having ischemic acute kidney injury and its therapeutic effects are then assessed. In some embodiments, appropriate dosage ranges and administration routes can be determined based on the results from initial animal studies.

Doses of a compound of formula (I), may be administered in single or divided applications. The doses may be administered once, or application may be repeated. Typically, application will be repeated weekly, biweekly, or every 3 weeks, every month, or every 2, 3, 4, 5, 6, 7, 8, 9, 10, 11, 12, 13, 14, 15, 16, 17, 18, 19, 20, 21, 22, 23, or every 24 months or more as needed to prevent, slow, or treat any disease, disorder or condition described herein. Doses may also be applied every 12 hours to 7 days apart, or more. For example, doses may be applied 12 hours, or 1, 2, 3, 4, 5, 6, or 7 days apart, or at any time interval falling between any two of these times, or between 12 hours and 7 days. The a compound of formula (I), for example, may be administered for up to four, six, eight, ten, twelve, fourteen, sixteen, eighteen, twenty, twenty-two, twenty-four or twenty-six weeks. For some indications, more frequent dosing, may be employed. In some embodiments, a compound of formula

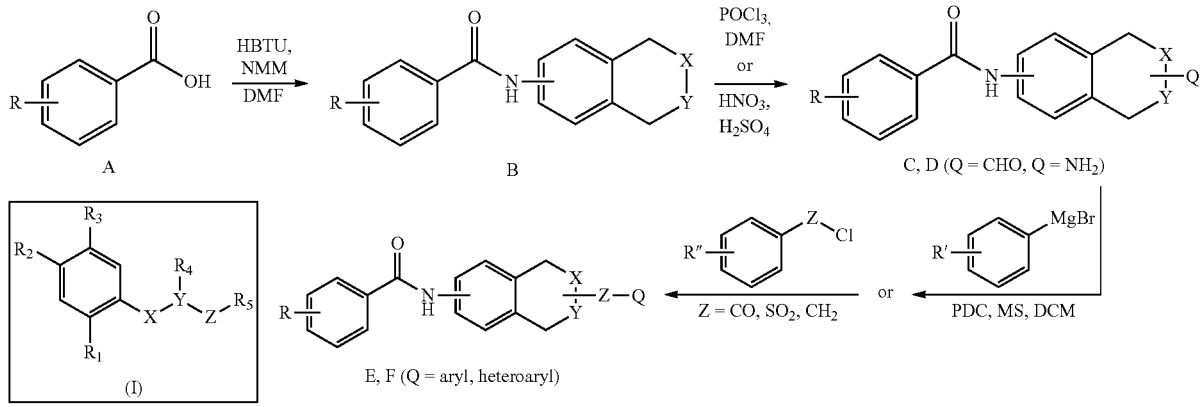

Scheme A. Synthesis of selected HSP90 inhibitors of this disclosure

In some embodiments, the formulations of this invention are substantially pure. By substantially pure is meant that the formulations comprise less than about 10%, 5%, or 1%, and preferably less than about 0.1%, of any impurity. In some embodiments the total impurities, including metabolites of a compound of formula (I), will be not more than 1-15%. In (I) may be administered at a starting dosage level daily for a first period of time and then an increased dosage level daily for a further period of time.

Examples of effective doses that may be used for the treatment of the diseases, disorders or conditions referenced herein are described. Some exemplary doses are in the range of about 0.5 to about 250 mg/kg, including, for example, from 1 to 100 mg/kg, or from 2 to 100 mg/kg and from 5 to 50 mg/kg. Some exemplary daily or other periodic dose amounts range from about 1-250 mg per dose, including, for example, from about 2-100 mg per dose, from about 25-50 mg per dose, from about 20-40 mg per dose, from about 50-75 mg per dose, from about 75-100 mg per dose and from about 100-250 mg per dose, including doses of 20, 50, 100, and 150 mg per dose, or any specific dose falling within one of these ranges of mg of drug per kg body weight.

The following specific examples are therefore to be construed as merely illustrative, not limitative, of the remainder of the disclosure in any way. All patents and publications cited herein are incorporated by reference.

Shown immediately below are the structures of exemplary compounds of formula (I). The methods for preparing these compounds, as well as the analytical data for the compounds thus prepared, are set forth in Example 1 below. The procedures for testing these compounds are described in EXAMPLES 2-4 also below.

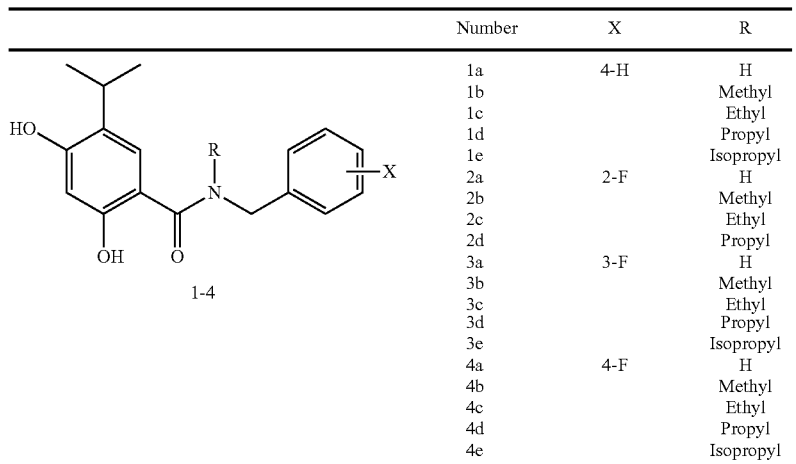

1-4

| Number | X | R |
|---|---|---|
| 1a | 4-H | H |
| 1b | | Methyl |
| 1c | | Ethyl |
| 1d | | Propyl |
| 1e | | Isopropyl |
| 2a | 2-F | H |
| 2b | | Methyl |
| 2c | | Ethyl |
| 2d | | Propyl |
| 3a | 3-F | H |
| 3b | | Methyl |
| 3c | | Ethyl |
| 3d | | Propyl |
| 3e | | Isopropyl |
| 4a | 4-F | H |
| 4b | | Methyl |
| 4c | | Ethyl |
| 4d | | Propyl |
| 4e | | Isopropyl |

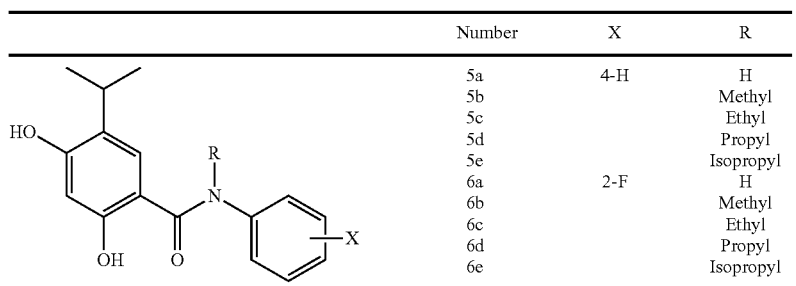

5-17

| Number | X | R |
|---|---|---|
| 5a | 4-H | H |
| 5b | | Methyl |
| 5c | | Ethyl |
| 5d | | Propyl |
| 5e | | Isopropyl |
| 6a | 2-F | H |
| 6b | | Methyl |
| 6c | | Ethyl |
| 6d | | Propyl |
| 6e | | Isopropyl |

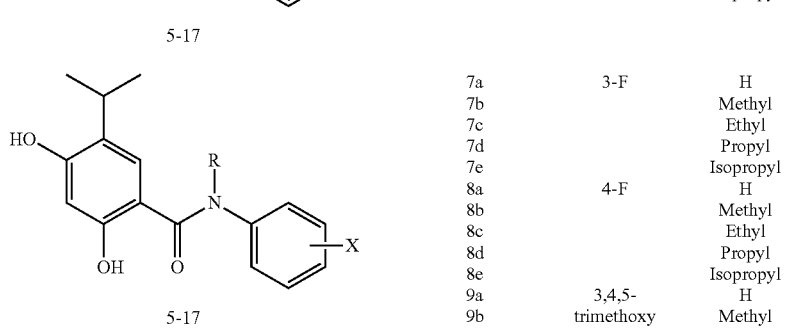

5-17

| | | |
|---|---|---|
| 7a | 3-F | H |
| 7b | | Methyl |
| 7c | | Ethyl |
| 7d | | Propyl |
| 7e | | Isopropyl |
| 8a | 4-F | H |
| 8b | | Methyl |
| 8c | | Ethyl |
| 8d | | Propyl |
| 8e | | Isopropyl |
| 9a | 3,4,5- | H |
| 9b | trimethoxy | Methyl |
| 9c | | Ethyl |
| 9d | | Propyl |
| 9e | | Isopropyl |
| 10a | 4-morpholino | H |
| 10b | | Methyl |
| 10c | | Ethyl |
| 10d | | Propyl |
| 10e | | Isopropyl |
| 11a | 2-morpholino | H |
| 11b | | Methyl |
| 11c | | Ethyl |
| 11d | | Propyl |
| 12a | 2-morpholino- | H |
| 12b | carbonyl | Methyl |
| 12c | | Ethyl |
| 12d | | Propyl |
| 13a | 3-morpholino- | H |
| 13b | carbonyl | Methyl |
| 13c | | Ethyl |

-continued

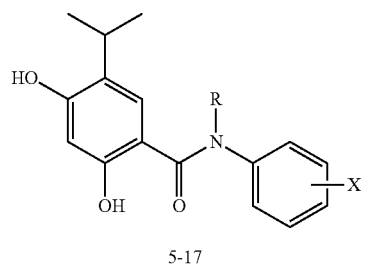

5-17

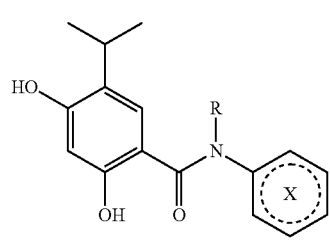

18-19

| Number | | |
|---|---|---|
| 13d | | Propyl |
| 13e | | Isopropyl |
| 14a | 4-morpholino-carbonyl | H |
| 14b | | Methyl |
| 14c | | Ethyl |
| 14d | | Propyl |
| 14e | | Isopropyl |
| 15a | 2-morpholino-methyl | H |
| 15b | | Ethyl |
| 15c | | Propyl |
| 16a | 3-morpholino-methyl | H |
| 16b | | Ethyl |
| 16c | | Propyl |
| 16d | | Isopropyl |
| 17a | 4-morpholino-methyl | H |
| 17b | | Ethyl |
| 17c | | Propyl |
| 18a | 3-aminopyridine | H |
| 18b | | Ethyl |
| 18c | | Propyl |
| 18d | | Isopropyl |
| 19a | 4-aminopyridine | H |
| 19b | | Ethyl |
| 19c | | Propyl |
| 19d | | Isopropyl |

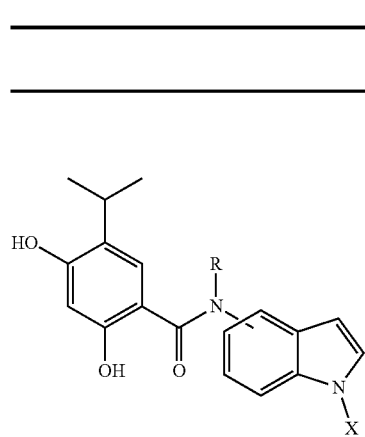

20-22

| Number | X | Position | R |
|---|---|---|---|
| 20a | H | 5- | H |
| 20b | | | Methyl |
| 20c | | | Ethyl |
| 20d | | | Propyl |
| 20e | | | Isopropyl |
| 20f | CH₃ | | H |
| 20g | | | Methyl |
| 20h | | | Ethyl |
| 20i | | | Propyl |

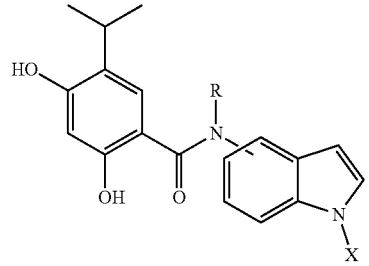

20-22

| 21a | H | 6- | H |
| 21b | CH₃ | | H |
| 21c | | | Methyl |
| 21d | | | Ethyl |
| 21e | | | Propyl |
| 21f | | | Isopropyl |
| 22a | CH₃ | 7- | H |
| 22b | | | Methyl |
| 22c | | | Ethyl |
| 22d | | | Propyl |
| 22e | | | Isopropyl |

-continued

| Number | X | R |
|---|---|---|
| 23a | H | H |
| 23b |  | Methyl |
| 23c |  | Ethyl |
| 23d |  | Propyl |
| 23e |  | Isopropyl |
| 23f | CH₃ | H |
| 23g |  | Ethyl |
| 23h |  | Propyl |

Structure 23

| Number | X | Y | Z | R |
|---|---|---|---|---|
| 24a | H | N | C | H |
| 24b | CH₃ |  |  | H |
| 24c |  |  |  | Methyl |
| 24d |  |  |  | Ethyl |
| 24e |  |  |  | Propyl |
| 24f |  |  |  | Isopropyl |
| 25a | H | C | N | H |
| 25b | CH₃ |  |  | Methyl |
| 26a | H | N | N | H |
| 26b | CH₃ |  |  | H |
| 26c |  |  |  | Methyl |
| 26d |  |  |  | Ethyl |
| 26e |  |  |  | Propyl |
| 26f |  |  |  | Isopropyl |

Structures 24-26

| Number | R |
|---|---|
| 27a | H |
| 27b | Methyl |
| 27c | Ethyl |
| 27d | Propyl |
| 27e | Isopropyl |

Structure 27

| Number | X | Position | R |
|---|---|---|---|
| 28a | H | 3- | H |
| 28b |  |  | Methyl |
| 28c |  |  | Ethyl |
| 28d |  |  | Propyl |
| 29a | H | 5- | H |
| 29b |  |  | Methyl |
| 29c |  |  | Ethyl |
| 30a | H | 6- | H |
| 30b |  |  | Methyl |
| 30c |  |  | Ethyl |
| 30d |  |  | Propyl |
| 31a | H | 8- | H |
| 32b |  |  | Methyl |
| 31c |  |  | Ethyl |
| 32a | CH₃ | 4- | H |
| 32b |  |  | Methyl |
| 32c |  |  | Ethyl |

Structures 28-32

-continued

| Structure | Number | X | R |
|---|---|---|---|
| 33 | 33a | H | Methyl |
|  | 33b |  | Ethyl |
|  | 33c | CH₃ | Methyl |
|  | 33d |  | Ethyl |

| Structure | Number | X |
|---|---|---|
| 34 | 34a | Methyl |
|  | 34b | O-Benzyl |

| Structure | Number | R |
|---|---|---|
| 35 | 35a | Methyl |
|  | 35b | Ethyl |

| Structure | Number | X | Y | R |
|---|---|---|---|---|
| 36-38 | 36a | 3-F | CO | H |
|  | 36b |  |  | Methyl |
|  | 36c |  |  | Ethyl |
|  | 36d |  |  | Propyl |
|  | 36e |  |  | Isopropyl |
|  | 37a | 4-F |  | H |
|  | 37b |  |  | Methyl |
|  | 37c |  |  | Ethyl |
|  | 37d |  |  | Propyl |
|  | 38a | 4-methoxy | SO₂ |  |
|  | 38b | 4-F |  |  |

| Structure | Number | X |
|---|---|---|
| 39 | 39a | 3,4,5-trimethoxy |
|  | 39b | 4-methoxy |
|  | 39c | 4-F |

-continued

| | Number | X |
|---|---|---|
| [structure 40: isopropyl, 2,4-dihydroxyphenyl chalcone with X substituent] | 40a | 3,4-dimethoxy |
| | 40b | 2,5-dimethoxy |

| | Number |
|---|---|
| [structure 41: isopropyl, 2,4-dihydroxyphenyl chalcone with 3,4,5-trimethoxyphenyl] | 41 |

[structure G-9–G-19: 2,4-dihydroxy-5-isopropyl benzamide linked via N(R) to phenyl-(X)-(CH₂)ₙ-C(O)NHOH]

G-9–G-19

| Number | Position | R | X | n |
|---|---|---|---|---|
| G-9 | Para | H | —NH—C(=O)— | 6 |
| G-10 | Para | CH₃ | —NH—C(=O)— | 6 |
| G-11 | Para | C₂H₅ | —NH—C(=O)— | 6 |
| G-12 | Para | C₃H₇ | —NH—C(=O)— | 6 |
| G-13 | Meta | H | —NH—C(=O)— | 6 |
| G-14 | Meta | CH₃ | —NH—C(=O)— | 6 |

| | | | | |
|---|---|---|---|---|
| G-15 | Meta | C₂H₅ | ![amide NHC=O] | 6 |
| G-16 | Ortho | H | ![amide NHC=O] | 6 |
| G-17 | Para | CH₃ | ![amide NHC=O] | 5 |
| G-18 | Para | CH₃ | ![amide NHC=O] | 7 |
| G-19 | Para | CH₃ | ![amide C(=O)NH] | 6 |

Depicted below are synthetic routes that were followed for synthesizing certain compounds of formula (I) listed above and shown in Example 1 below.

Scheme 1

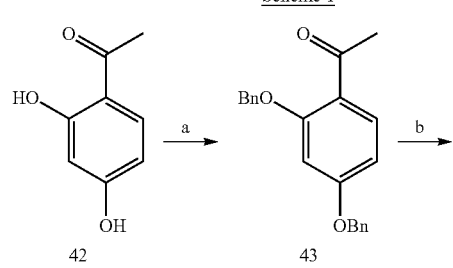

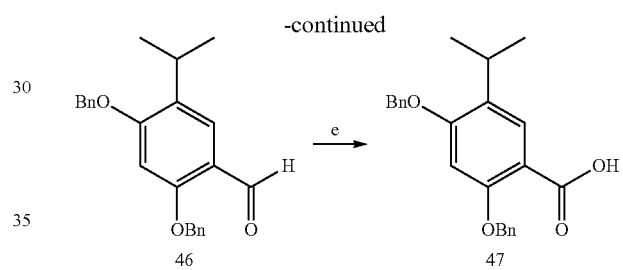

*Reagents and condition
(a) benzyl bromide, K₂CO₃, acetone, reflux, 93%
(b) methylmagnesium bromide, THF, 0° C. to r.t., 77%
(c) triethylsilane, TFA, DCM, -78° C. to r,t., 92%
(d) POCl₃, DMF, 0° C. to 80° C., 92%
(e) sulfamic acid, NaClO₂, H₂O, THF, DMSO, 0° C. to r.t., 65%

Scheme 2

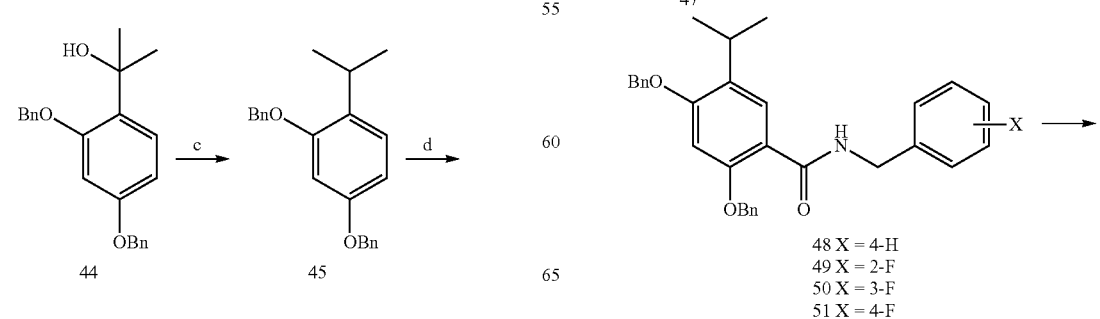

48 X = 4-H
49 X = 2-F
50 X = 3-F
51 X = 4-F

23
-continued

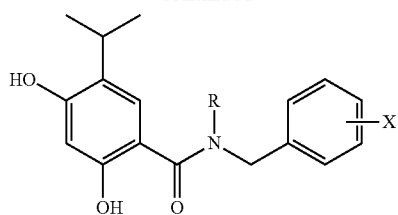

| | X | R |
|---|---|---|
| 1a | H | H |
| 1b | H | methyl |
| 1c | H | ethyl |
| 1d | H | propyl |
| 2a | 2-F | H |
| 2b | 2-F | methyl |
| 2c | 2-F | ethyl |
| 2d | 2-F | propyl |
| 3a | 3-F | H |
| 3b | 3-F | methyl |
| 3c | 3-F | ethyl |
| 3d | 3-F | propyl |
| 4a | 4-F | H |
| 4b | 4-F | methyl |
| 4c | 4-F | ethyl |
| 4d | 4-F | propyl |

*Reagents and condition
(a) benzyamine or substituted bensylamine, EDC.HCl, HOBt, NMM, DMF, r.t., 78-83%
(b) 10% Pd/C, $H_2$, MeOH, r.t. for 1a, 2a, 3a, 4a, 85-94%
(c) alkyl iodide, NaH, DMF, r.t. then 10% Pd/C, $H_2$, MeOH, r.t., for 1b-1d, 2b-2d, 3b-3d, 4b-4d, 60-70%

Scheme 3

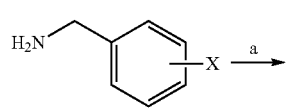

| | X |
|---|---|
| 52 | 4-H |
| 53 | 3-F |
| 54 | 4-F |

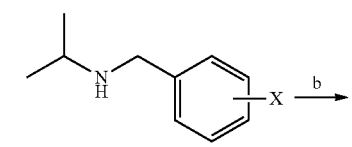

| | X |
|---|---|
| 55 | 4-H |
| 56 | 3-F |
| 57 | 4-F |

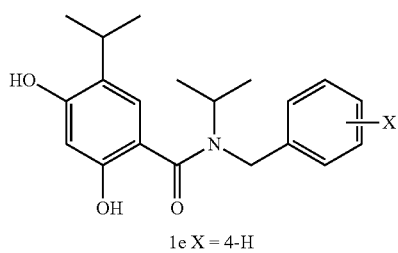

| | X |
|---|---|
| 1e | 4-H |
| 3e | 3-F |
| 4e | 4-F |

*Reagents and condition
(a) acetone, $NaBH_3CN$, MeOH, aceti acid, r.t., 41-44%
(b) 47, EDC.HCl, HOBt, NMM, DMF, r.t. then 10% Pd/C, $H_2$, MeOH, r.t., 67-71%

24

Scheme 4

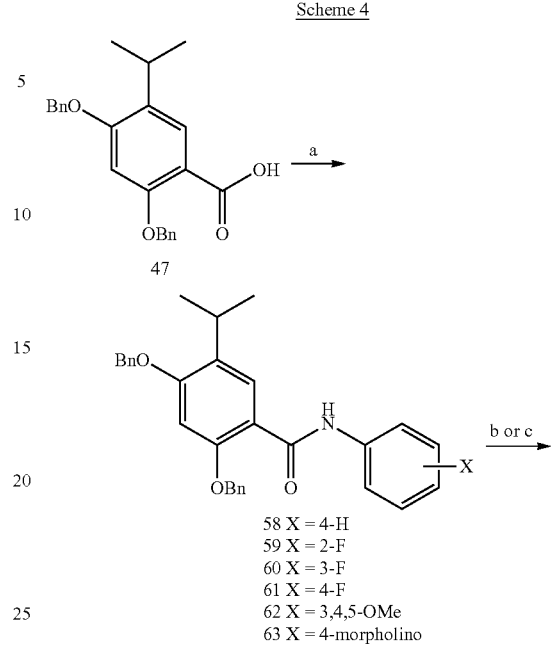

| | X |
|---|---|
| 58 | 4-H |
| 59 | 2-F |
| 60 | 3-F |
| 61 | 4-F |
| 62 | 3,4,5-OMe |
| 63 | 4-morpholino |

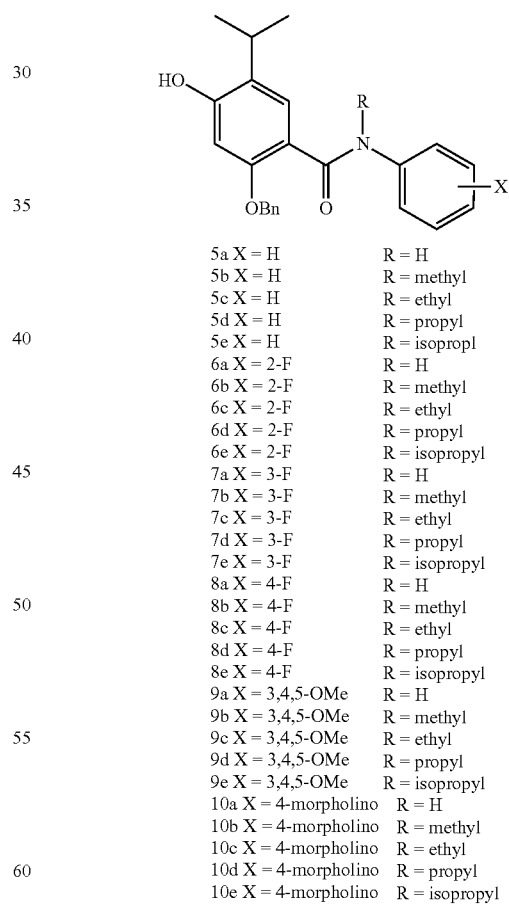

| | X | R |
|---|---|---|
| 5a | H | H |
| 5b | H | methyl |
| 5c | H | ethyl |
| 5d | H | propyl |
| 5e | H | isopropl |
| 6a | 2-F | H |
| 6b | 2-F | methyl |
| 6c | 2-F | ethyl |
| 6d | 2-F | propyl |
| 6e | 2-F | isopropyl |
| 7a | 3-F | H |
| 7b | 3-F | methyl |
| 7c | 3-F | ethyl |
| 7d | 3-F | propyl |
| 7e | 3-F | isopropyl |
| 8a | 4-F | H |
| 8b | 4-F | methyl |
| 8c | 4-F | ethyl |
| 8d | 4-F | propyl |
| 8e | 4-F | isopropyl |
| 9a | 3,4,5-OMe | H |
| 9b | 3,4,5-OMe | methyl |
| 9c | 3,4,5-OMe | ethyl |
| 9d | 3,4,5-OMe | propyl |
| 9e | 3,4,5-OMe | isopropyl |
| 10a | 4-morpholino | H |
| 10b | 4-morpholino | methyl |
| 10c | 4-morpholino | ethyl |
| 10d | 4-morpholino | propyl |
| 10e | 4-morpholino | isopropyl |

*Reagents and condition
(a) aniline or substituted phenylamine, EDC, HCl, HOBt, NMM, DMF, r.t., 71-82%
(b) 10% Pd/C, $H_2$, MeOH, r.t. for 5a, 6a, 7a, 8a, 9a, 10a, 84-89%
(c) alkyl iodide, NaH, DMF, r.t. then 10% Pd/C, $H_2$, MeOH, r.t., for 5b-5e, 6b-6e, 7b-7e, 8b-8e, 9b-9e, 10b-10e, 56-74%

Scheme 5

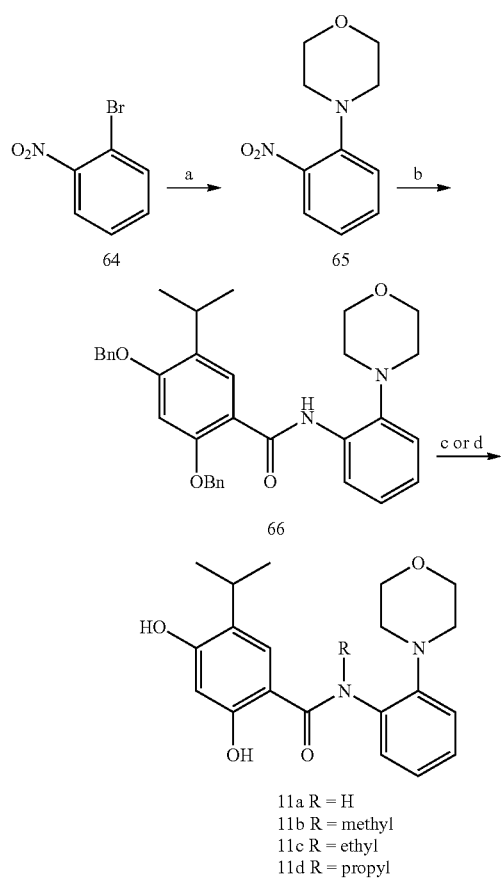

*Reagents and condition
(a) morpholine, reflux, 97%
(b) 10% Pd/C, H₂, MeOH, r.t. then 47, EDC.HCl, HOBt, NMM, DMf, r.t., 63%
(c) 10% Pd/C, H₂, MeOH, r.t. for 11a, 90%
(d) alkyl iodine, NaH, DMF, r.t. then 10% Pd/C, H₂, MeOH, r.t., for 11b-11d, 68%-74%

Scheme 6

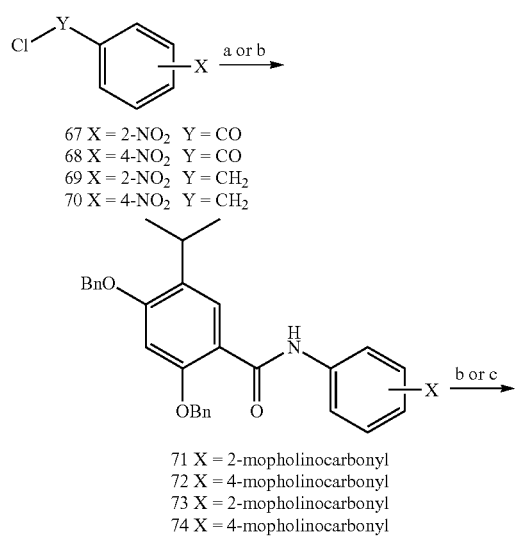

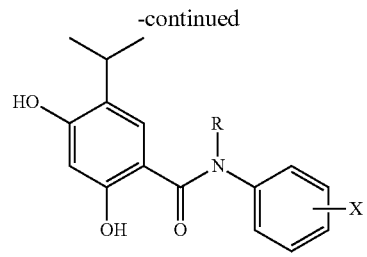

12a X = 2-mopholinocarbonyl   R = H
12b X = 2-mopholinocarbonyl   R = methyl
12c X = 2-mopholinocarbonyl   R = ethyl
12d X = 2-mopholinocarbonyl   R = propyl
14a X = 4-mopholinocarbonyl   R = H
14b X = 4-mopholinocarbonyl   R = methyl
14c X = 4-mopholinocarbonyl   R = ethyl
14d X = 4-mopholinocarbonyl   R = propyl
14e X = 4-mopholinocarbonyl   R = isopropyl
15a X = 2-mopholinomethyl     R = H
15b X = 2-mopholinomethyl     R = ethyl
15c X = 2-mopholinomethyl     R = propyl
17a X = 4-mopholinomethyl     R = H
17b X = 4-mopholinomethyl     R = ethyl
17c X = 4-mopholinomethyl     R = propyl

*Reagents and condition
(a) (i) morpholine, TEA, DCM, r.t.
    (ii) 10% Pd/C, H₂, MeOH, r.t.
    (iii) 47, EDC.HCl, HOBt, NMM, DMF, r.t., for 71-72, 50-65%
(b) (i) morpholine, TEA, DCM, r.t.
    (ii) Fe powder, NH₄Cl, IPA/H₂O, reflux
    (iii) 47, EDC.HCl, HOBt, NMM, DMF, r.t., for 73-74, 52%
(c) 10% Pd/C, H₂, MeOH, r.t. for 12a, 14a, 15a, 17a, 48-93%
(d) alkyl iodide, NaH, DMF, r.t. then 10% Pd/C, H₂, MeOH, r.t. for 12b-12d, 14b-14e, 15b-15c, 17b-17c, 52-74%

Scheme 7

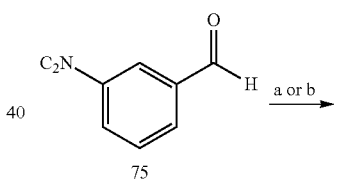

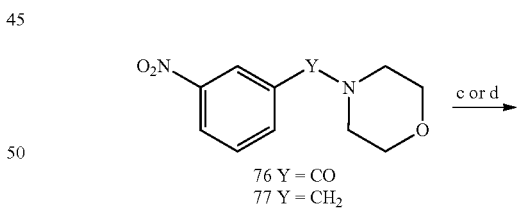

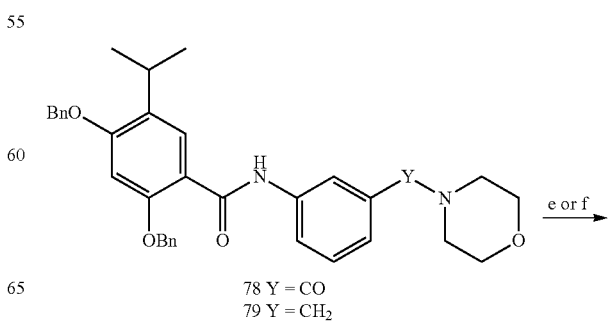

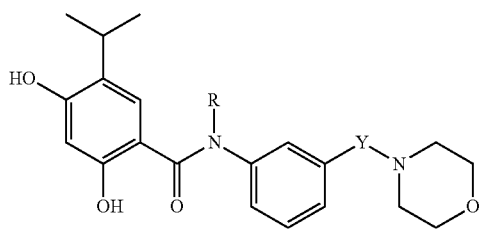

13a Y = CO, R = H
13b Y = CO, R = methyl
13c Y = CO, R = ethyl
13d Y = CO, R = propyl
13e Y = CO, R = isopropyl
16a Y = CH$_2$, R = H
16b Y = CH$_2$, R = ethyl
16c Y = CH$_2$, R = propyl
16d Y = CH$_2$, R = isopropyl

*Reagents and condition
(a) sulfamic acid, NaClO$_2$, H$_2$O/THF/DMSO, r.t. then mopholine, EDC.HCl, HOBt, NMM, DMF, r.t., for 76, 62%
(b) morpholine, NaBH$_3$CN, MeOH, acetic acid, r.t., for 77, 42%
(c) 10% Pd/C, H$_2$, MeOH, r.t. then 47, EDC.HCl, HOBt, NMM, DMF, r.t., for 78, 58%
(d) Fe powder, NH4Cl, IPA/H$_2$O, reflux, then 47, EDC.HCl, HOBt, NMM, DMF, r.t., for 79, 51%
(e) 10% Pd/C, H$_2$, MeOH, r.t., for 13a, 16a, 56%, 93%
(f) alkyl iodide, NaH, DMF, r.t. then 10% Pd/C, H$_2$, MeOH, r.t., for 13b-13e, 16b-16d, 58-71%

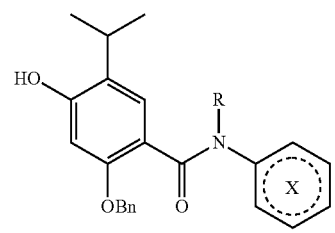

18a X = 3-aminopyridine R = H
18b X = 3-aminopyridine R = ethyl
18c X = 3-aminopyridine R = propyl
18d X = 3-aminopyridine R = isopropyl
19a X = 4-aminopyridine R = H
19b X = 4-aminopyridine R = ethyl
19c X = 4-aminopyridine R = propyl
19d X = 4-aminopyridine R = isopropyl

*Reagents and condition
(a) 3-or 4-aminopyridine, EDC, HOBt, NMM, DMF, r.t., for 80-81, 71-73%
(b) 10% Pd/C. H$_2$, MeOH, r.t. for 18a, 19a, 87-88%
(c) alkyl iodide, NaH, DMF, r.t. then 10% Pd/C, H$_2$, MeOH, r.t., 18b-18d, 19a-19d, 60-70%

Scheme 9

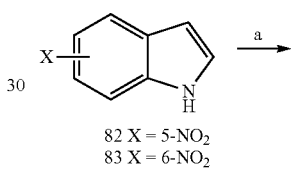

82 X = 5-NO$_2$
83 X = 6-NO$_2$

Scheme 8

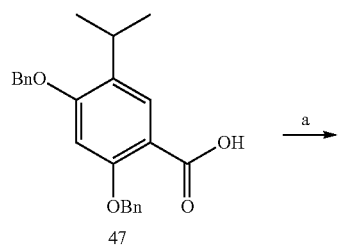

47

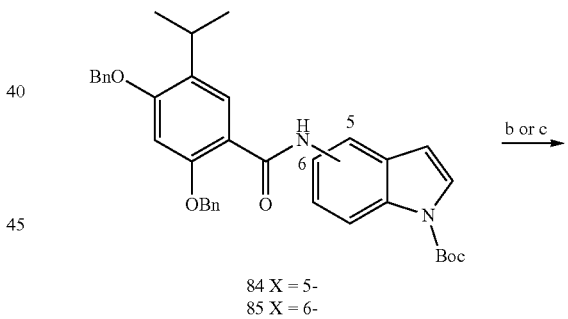

84 X = 5-
85 X = 6-

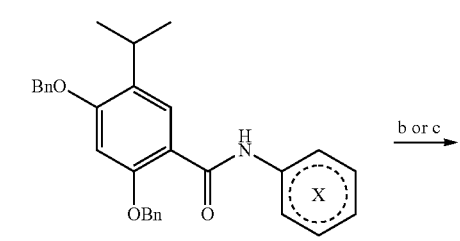

80 X = 3-aminopyridine
81 X = 4-aminopyridine

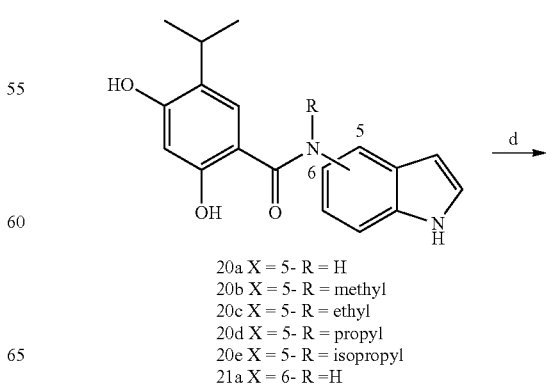

20a X = 5- R = H
20b X = 5- R = methyl
20c X = 5- R = ethyl
20d X = 5- R = propyl
20e X = 5- R = isopropyl
21a X = 6- R = H 29
-continued

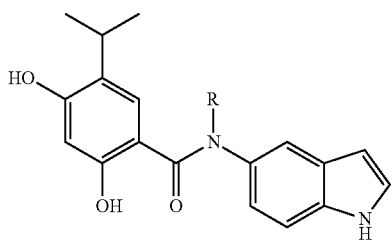

23a R = H
23b R = methyl
23c R = ethyl
23d R = propyl
23e R = isopropyl

*Reagents and condition
(a) (i) Boc anhydride, DMAP, DCM, r.t.
  (ii) Fe powder, NH$_4$Cl, IPA/H$_2$O, reflux
  (iii) 47, EDC, HOBt, NMM, DMF, r.t., 79%
(b) (i) TFA, DCM, r.t.
  (ii) 10% Pd/C, H$_2$, MeOH, r.t. for 20a, 73%
(c) (i) alkyl iodide, NaH, DMF, r.t.
  (ii) TFA, DCM, r.t.
  (iii) 10% Pd/C, H$_2$, MeOH, r.t. for 20b-20e, 21a, 48-57%
(d) NaBH$_3$CN, acetic acid, 0° C. to r.t., 70-79%

30
-continued

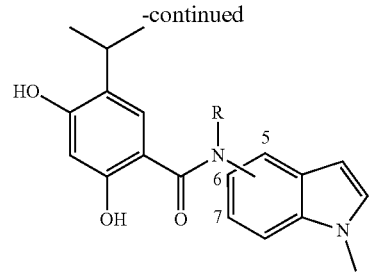

20f X = 5-position R = H
20g X = 5-position R = methyl
20h X = 5-position R = ethyl
20i X = 5-position R = propyl
21b X = 6-position R = H
21c X = 6-position R = methyl
21d X = 6-position R = ethyl
21e X = 6-position R = propyl
21f X = 6-position R = isopropyl
22a X = 7-position R = H
22b X = 7-position R = methyl
22c X = 7-position R = ethyl
22d X = 7-position R = propyl
22e X = 7-position R = isopropyl

*Reagents and condition
(a) MeI, NaH, DMF, r.t. 92%
(b) (i) Fe Powder, NH$_4$Cl, IPA/H$_2$O, reflux
  (ii) 47, EDC, HOBt, NMM, DMF, r.t., 36%
(c) 10% Pd/C, H$_2$, MeOH, r.t. for 20f, 21b, 22a, 81%
(d) alkyl iodide, NaH, DMF, r.t. then 10% PD/C, H$_2$, MeOH, THF, 40psi, r.t., for 20g-20i, 69-75%
(e) alkyl iodide, NaH, DMF, r.t. then 10% PD/C, H$_2$, MeOH, for 21c-21e, 22b-22e, r.t.

Scheme 10

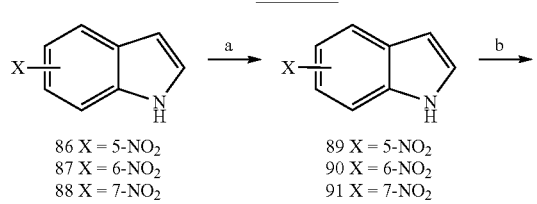

86 X = 5-NO$_2$
87 X = 6-NO$_2$
88 X = 7-NO$_2$

89 X = 5-NO$_2$
90 X = 6-NO$_2$
91 X = 7-NO$_2$

Scheme 11

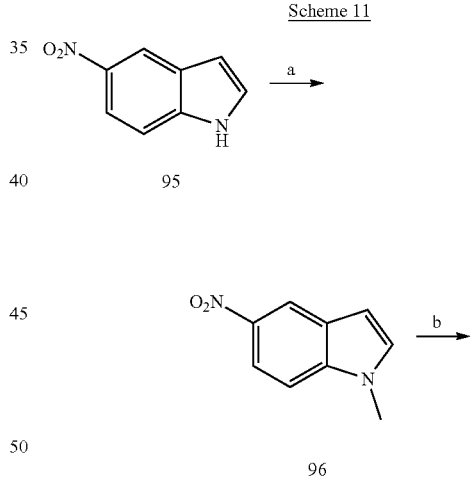

95

96

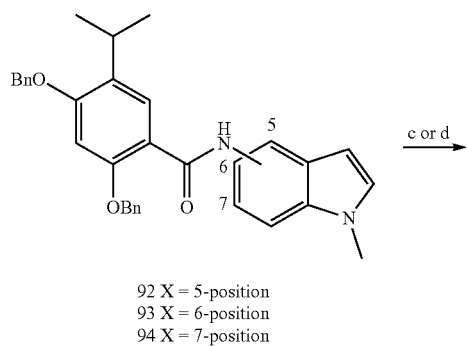

92 X = 5-position
93 X = 6-position
94 X = 7-position

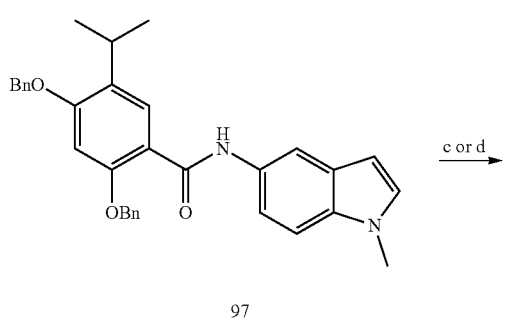

97

31

-continued

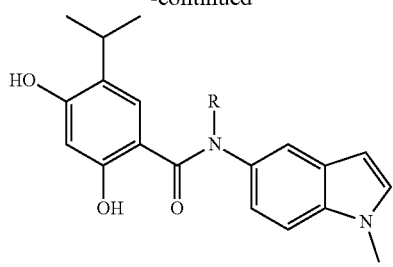

23f R = H
23g R = ethyl
23h R = propyl

*Reagents and condition
(a) MeI, NaH, DMF, r.t. 88%
(b) (i) Fe Powder, NH₄Cl, IPA/H₂O, reflux
    (ii) 47, EDC, HOBt, NMM, DMF, r.t., 46%
(c) 10% Pd/C, H₂, MeOH, r.t. for 23f, 81%
(d) alkyl iodide, NaH, DMF, r.t. then 10% Pd/C, H₂, MeOH, r.t., for 23g-23h, 67-71%

Scheme 12

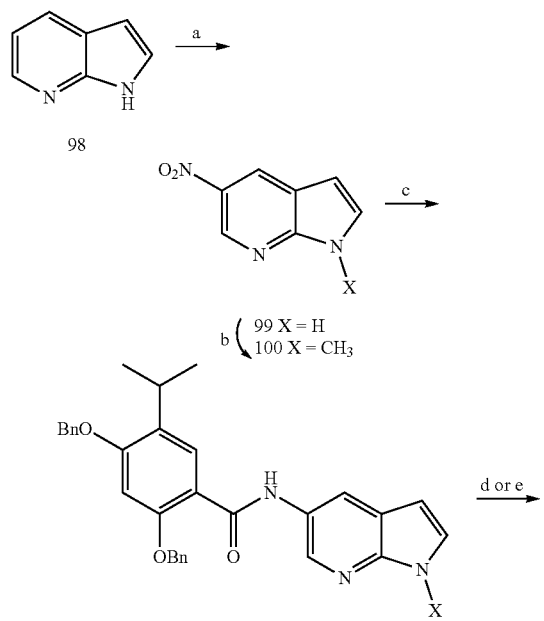

98

99 X = H
100 X = CH₃

101 X = H
102 X = CH₃

24a X = H,    R = H
24b X = CH₃,  R = H
24c X = CH₃,  R = methyl
24d X = CH₃,  R = ethyl
24e X = CH₃,  R = propyl
24f X = CH₃,  R = isopropyl

32

-continued

*Reagents and condition
(a) (i) K₂CO₃, ACN, benzenesulfonyl chloride, reflux,
    (ii) TEANO₂, TFAA, CH₂Cl₂, r.t.
    (iii) 5N NaOH (aq.), MeOH, reflux
(b) NaH, MeI, DMF, r.t.
(c) (i) Fe powder, NH₄Cl, IPA/H₂O, reflux
    (ii) 47, HBTU, DIPEA, DMF, r.t.
(d) 10% Pd/C, MeOH, r.t. for 24a-24b
(e) (i) alkyl iodide, NaH, DMF, r.t.
    (ii) 10% PD/C, MeOH, r.t. for 24c-24f Scheme 13

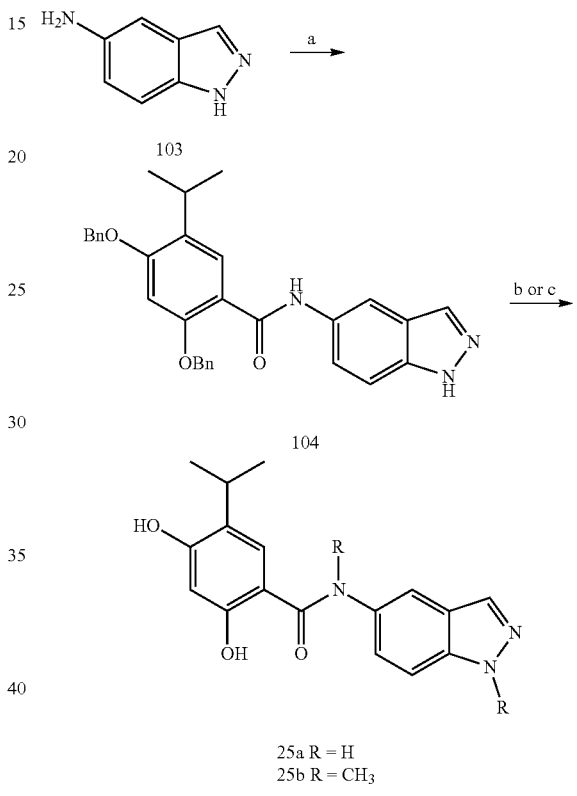

103

104

25a R = H
25b R = CH₃

*Reagents and condiition
(a) 47, HBTU, DIPEA, DMF, r.t.
(b) 10% Pd/C, MeOH, r.t. for 25a
(c) (i) methyl iodide, NaH, DMF, r.t.
    (ii) 10% Pd/C, MeOH, r.t. for 25b Scheme 14

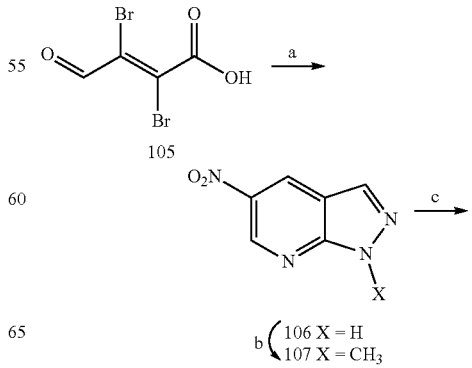

105

106 X = H
107 X = CH₃

33

-continued

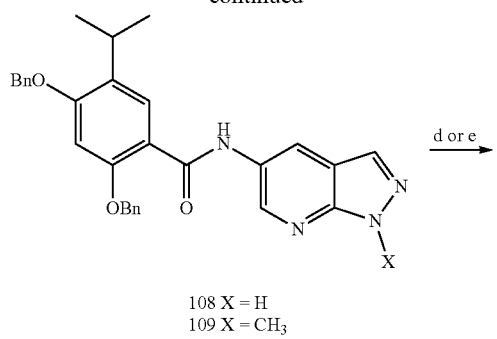

108 X = H
109 X = CH$_3$

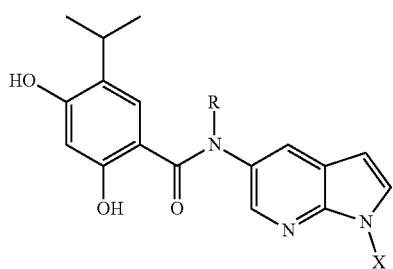

26a X = H,     R = H
26b X = CH$_3$, R = H
26c X = CH$_3$, R = methyl
26d X = CH$_3$, R = ethyl
26e X = CH$_3$, R = propyl
26f X = CH$_3$, R = isopropyl

*Reagents and condition
(a) NaNO$_2$, H$_2$O, EtOH, 55° C. then 3-aminopyrazole, AcOH, 90° C.
(b) NaH, MeI, DMF, r.t.
(c) (i) Fe powder, NH$_4$Cl, IPA/H$_2$O, reflux
    (ii) 47, EDC.HCl, HOBt, NMM, DMF, r.t.
(d) 10% Pd/C, MeOH, r.t. for 26a-26b
(e) (i) alkyl iodidiem NaH, DMF, r.t.
    (ii) 10% Pd/C, MeOH, r.t. for 26c-26f Scheme 15

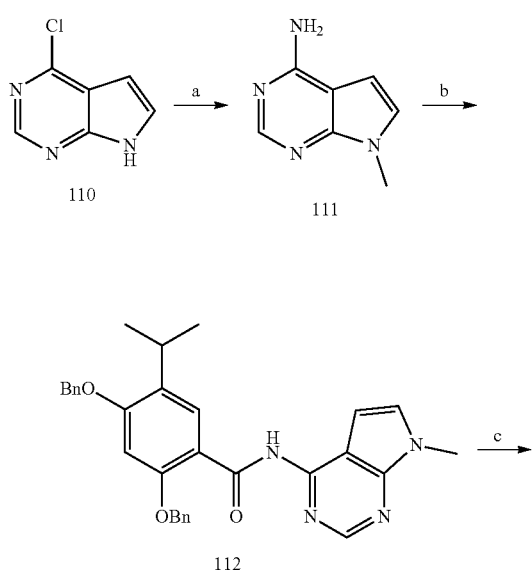

110    111

112

34

-continued

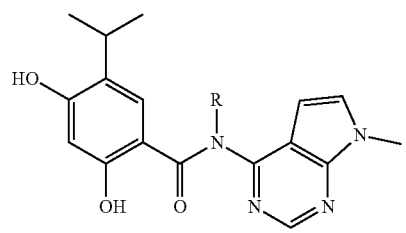

27a X = CH$_3$, R = H
27b X = CH$_3$, R = methyl
27c X = CH$_3$, R = ethyl
27d X = CH$_3$, R = propyl
27e X = CH$_3$, R = isopropyl

*Reagents and condition
(a) NaH, CH$_3$I, DMF, r.t. then NH$_4$OH (aq.), 100° C., sealtube
(b) 47, HBTU, DIPEA, DMF, 50° C., then NaH, alkyl iodide, DMF, r.t.
(c) H$_2$, 10% Pd/C, MeOh, r.t.

Scheme 16

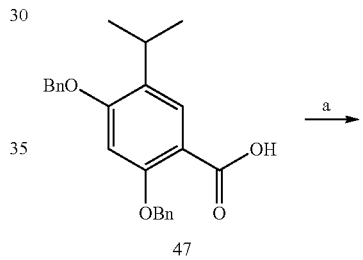

47

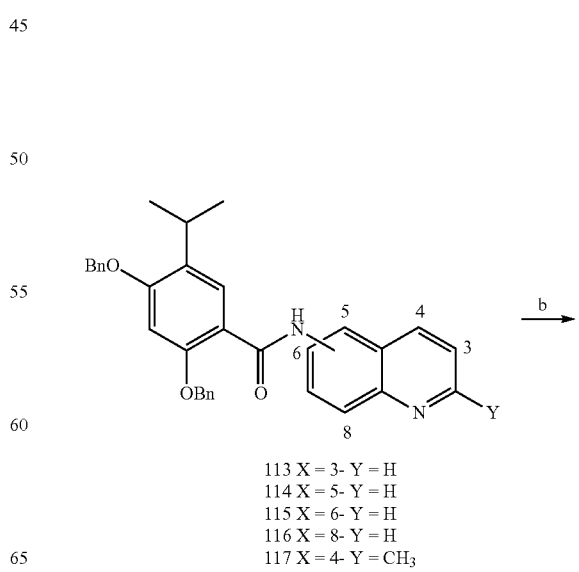

113 X = 3-  Y = H
114 X = 5-  Y = H
115 X = 6-  Y = H
116 X = 8-  Y = H
117 X = 4-  Y = CH$_3$

35
-continued

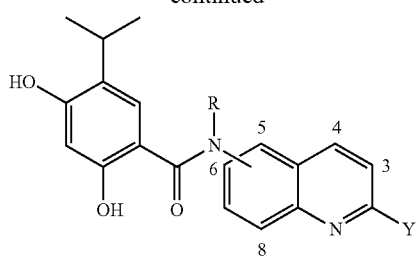

28a X = 3- Y = H R = H
28b X = 3- Y = H R = CH₃
28c X = 3- Y = H R = C₂H₅
28d X = 3- Y = H R = C₃H₇
29a X = 5- Y = H R = H
30a X = 6- Y = H R = H
30c X = 6- Y = H R = C₂H₅
31a X = 8- Y = H R = H
31c X = 8- Y = H R = C₂H₅
32a X = 4- Y = CH₃ R = H

*Reagents and condition
(a) (i) EDC.HCl, HOBt, NMM, DMF, r.t. for 113, 116
(ii) EDC, DMAP, DCM, r.t. for 114, 115
(iii) EDC.HCl, HOBt, NMM, DMF, 50° C. for 117
(b) (i) 10% Pd/C, H₂, alkyl alcohol, r.t. for 28a, 30a, 31a
(ii) 10% Pd/C, HCOOH, MeOH, reflux for 29a, 32a
(iii) alkyl iodide, KOtBu, THF then 10% Pd/C, H₂, EtOH, r.t. for 28b, 30c
(iv) alkyl iodide, KOtBu, THF then 10% Pd/C, HCOOH, alkyl alcohol, reflux for 28c-28d, 31c Scheme 17

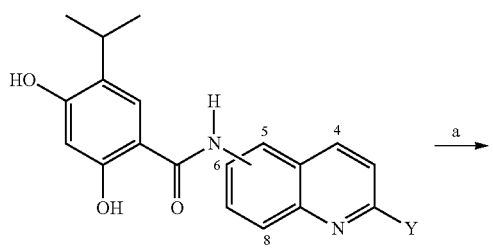

29a X = 5- Y = H R = H
30a X = 6- Y = H R = H
31a X = 8- Y = H R = H
32a X = 4- Y = CH₃ R = H

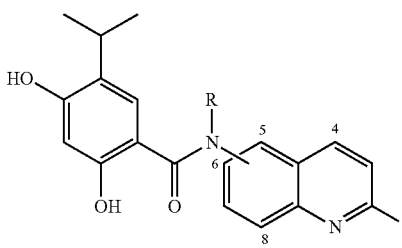

29b X = 5- Y = H R = CH₃
29c X = 5- Y = H R = C₂H₅
30b X = 6- Y = H R = CH₃
30d X = 6- Y = H R = C₃H₇
31b X = 8- Y = H R = CH₃
32b X = 4- Y = CH₃ R = CH₃
32c X = 4- Y = CH₃ R = C₂H₅

*Reagents and condition
(a) (i) TBDMSCl, DIPEA, CH₂Cl₂, r.t. (ii) KOtBu, alkyl iodide, THF, r.t. (iii) TBAF, CH₂Cl₂, r.t.

36

Scheme 18

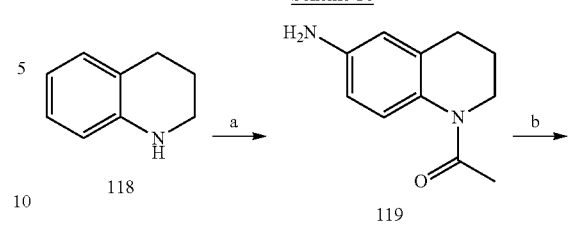

118 → 119

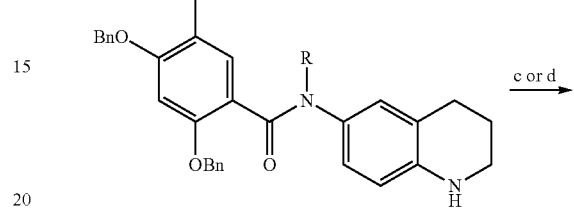

120 R = H
121 R = CH₃

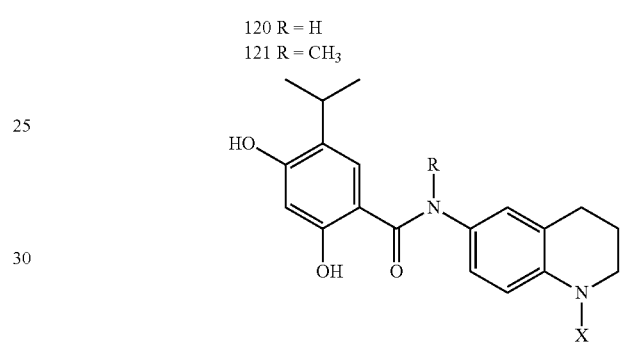

33a X = H R = methyl
33b X = H R = ethyl
33c X = CH₃ R = methyl
33d X = CH₃ R = ethyl

*Reagents and condition
(a) (i) acetyl chloride, CH₂Cl₂, r.t. (ii) Ac₂O, HNO₃, 50° C. (iii) H₂, 10% Pd/C, MeOH, r.t.
(b) (i) 47, EDC, HCl, HOBt, NMM, DMF, r,t. (ii) NaH, alkyl halide, DMF, r.t. (iii) 1N KOH, EtOH, reflux
(c) H₂, 10% Pd/C, MeOH, r.t. for 33a-33b
(d) (i) TEA, CH₃I, CH₂Cl₂ (ii) H₂, 10% Pd/C, MeOH, r.t. for 33c-33d Scheme 19

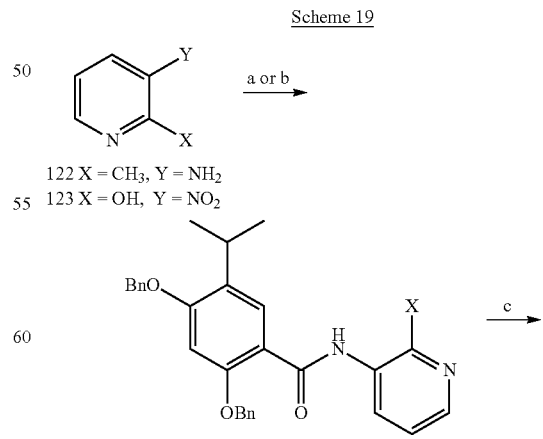

122 X = CH₃, Y = NH₂
123 X = OH, Y = NO₂

124 X = CH₃
125 X = OBn

37
-continued

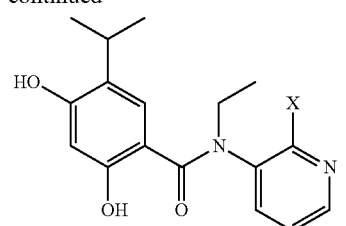

34a X = CH₃
34b X = OBn

*Reagents and condition
(a) 47, HBTU, DIPEA, DMF, 40° C. for 124
(b) (i) acetone, Benzyl bromide, reflux then Fe powder, NH₄Cl, IPA/H₂O, reflux (ii) 47, HBTU, DIPEA, DMF, 40° C. for 125
(c) (i) KOtBu, ethyl iodide, THF, r.t. (ii) 10% Pd/C, MeOH, H₂, r.t.

Scheme 20

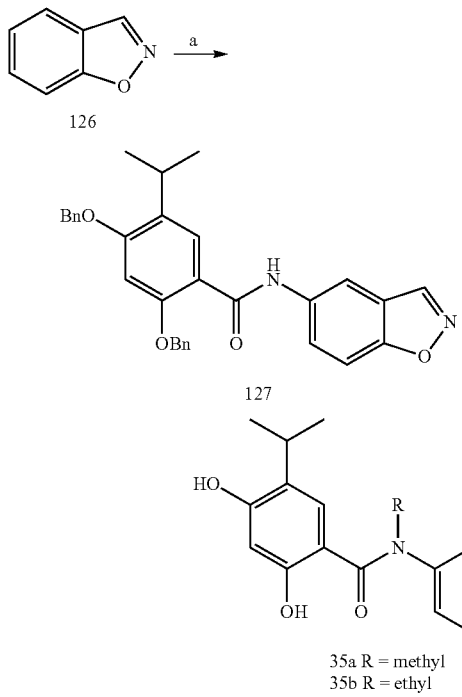

127

35a R = methyl
35b R = ethyl

*Reagents and condition
(a) (i) Fe powder, NH₄Cl, IPA/H₂O, reflux (ii) 47, HBTU, DIPEA, DMF, 40° C.
(b) (i) alkyl iodide, NaH, DMF, r.t. (ii) 10% Pd/C, MeOH, H₂, r.t.

Scheme 21

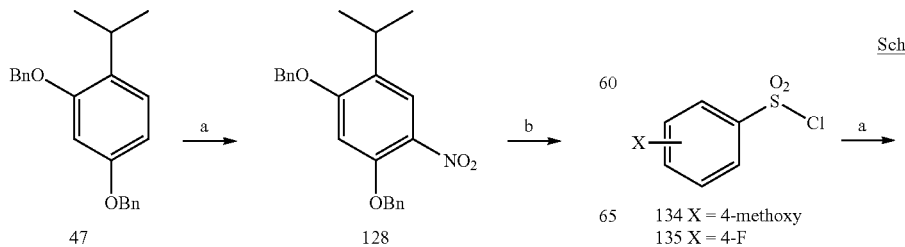

47    128

38
-continued

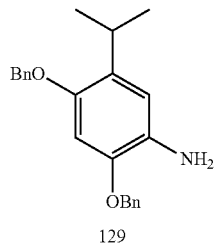

129

*Reagents and condition
(a) HNO₃, H₂SO₄, r.t., 54%
(b) Fe powder, NH₄Cl, IPA/H₂O, reflux, 73%

Scheme 22

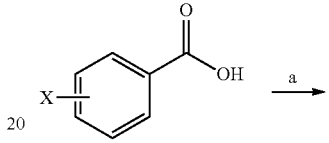

130 X = 3-F
131 X = 4-F

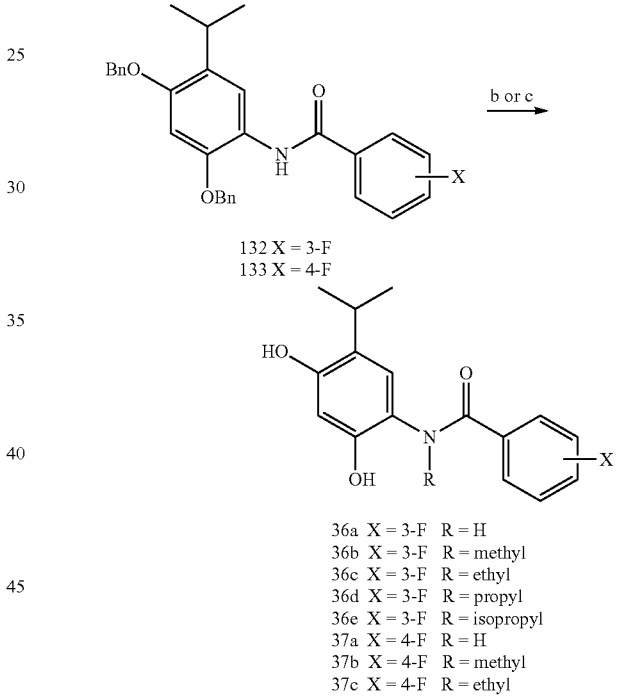

132 X = 3-F
133 X = 4-F

36a X = 3-F  R = H
36b X = 3-F  R = methyl
36c X = 3-F  R = ethyl
36d X = 3-F  R = propyl
36e X = 3-F  R = isopropyl
37a X = 4-F  R = H
37b X = 4-F  R = methyl
37c X = 4-F  R = ethyl
37d X = 4-F  R = propyl

*Reagents and condition
(a) 129, EDC, HOBt, NMM, DMF, r.t., 61-64%
(b) 10% Pd/C, H₂, MeOH, r.t. for 36a, 37a, 81-86%
(c) alkyl iodide, NaH, DMF, r.t. then 10% Pd/C, H₂, MeOH, r.t., for 36b-36e, 37b-37d, 54-63%

Scheme 23

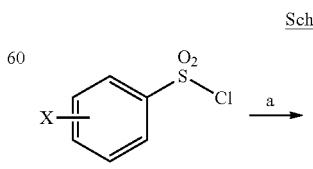

134 X = 4-methoxy
135 X = 4-F

39
-continued

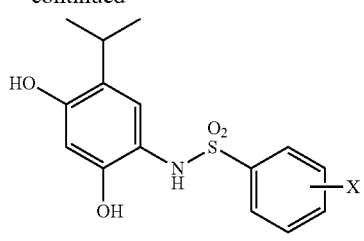

38a X = 4-methoxy
38b X = 4-F

*Reagents and condition
(a) 129, DCM, r.t. then 10% Pd/C, H₂, MeOH, r.t., 64-65%

40
-continued

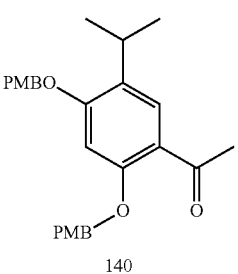

140

*Reagents and condition
(a) 10% Pd/C, H₂, MeOH, r.t., 40 psi then acetic acid, ZnCl₂, reflux, 58%
(b) 4-methoxybenzyl chloride, Cs₂CO₃, CH₃CN, reflux, 66%

Scheme 24

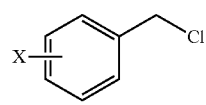

136 X = 3'4'5'-trimethoxy
137 X = 4-methoxy
138 X = 4-F

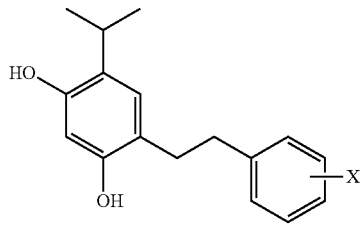

39a X = 3'4'5'-trimethoxy
39b X = 4-methoxy
39c X = 4-F

*Reagents and condition
(a) (i) triphenylphosphine, toluene, reflux (ii) 46, NaH, toluene, r.t. (iii) 10% Pd/C, H₂, MeOH, r.t., 51-56%

Scheme 26

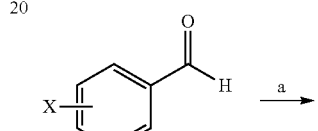

141 X = 3'4'-dimethoxy
142 X = 2'5'-dimethoxy

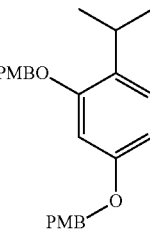

143 X = 3'4'-dimethoxy
144 X = 2'5'-dimethoxy

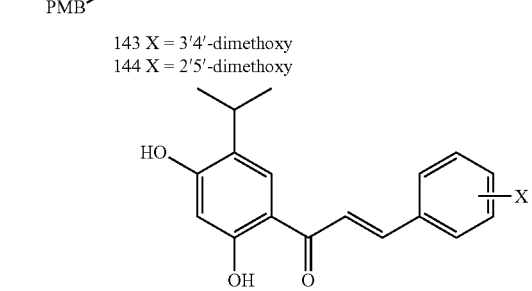

40a X = 3'4'-dimethoxy
40b X = 2'5'-dimethoxy

*Reagents and condition
(a) 140, 1N NaHO(aq), MeOH, DCM, 50° C., 51-52%
(b) TiCl₄, DCM, 0° C., 47-54%

Scheme 25

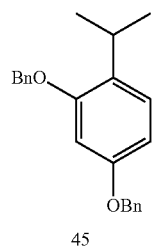 a → 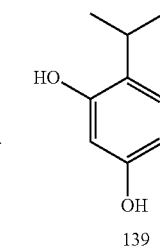 b →

45        139

Scheme 27

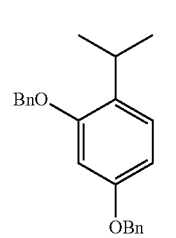 a → 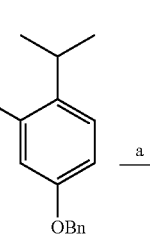 b →

45        145

41
-continued

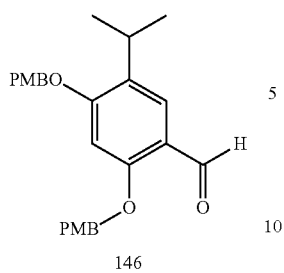
146

*Reagents and condition
(a) 10% Pd/C, H₂, MeOH, r.t., 40 psi then POCl₃, DMF, r.t., 56%
(b) 4-methoxybenzyl chloride, TEA, CH₂Cl₂, r.t., 64%

Scheme 28

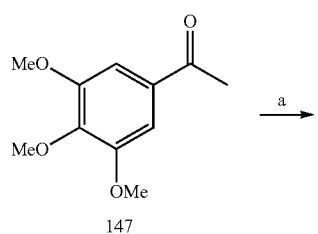
147

↓ a

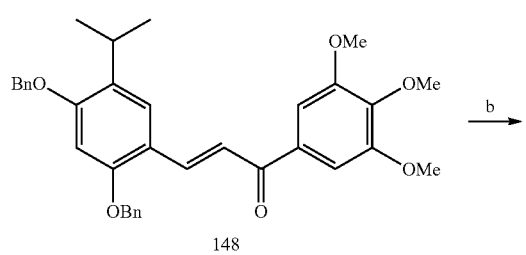
148

↓ b

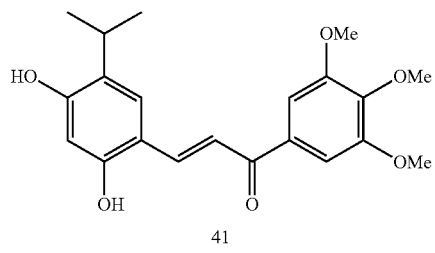 [SMILES: COc1cc(C(=O)/C=C/c2cc(C(C)C)c(O)cc2O)cc(OC)c1OC]
41

*Reagents and condition
(a) 146, 1N NaOH$_{(aq)}$, MeOH, DCM, r.t., 43%
(b) TiCl₄, DCM, 0° C., 48%

Scheme 29

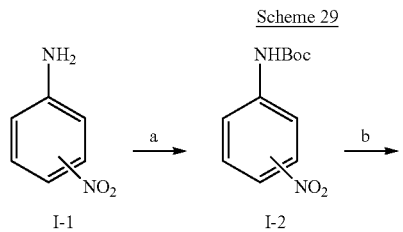
I-1 → I-2 a → b →

42
-continued

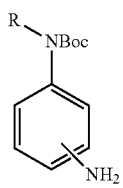

Position | R
I-3a: Para | H
I-3b: Para | CH₃
I-3c: Para | C₂H₅
I-3d: Para | CH₃CH₂CH₃
I-3e: Meta | H
I-3f: Meta | CH₃
I-3g: Meta | C₂H₅
I-3H: Ortho | H Reagents and conditions: (a) DMAP, TEA, DCM, rt; (b) (i) Different alkyl iodides, NaH, DMF, 0° C. to rt; (ii) NH4Cl, Fe, IPA: H₂O (4:1), reflux.

Scheme 30

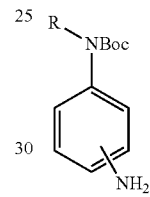
I-3a - I-3h

+

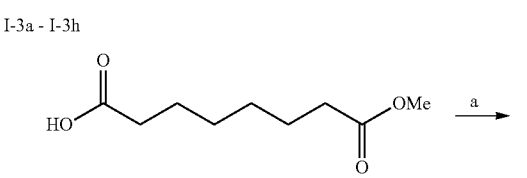
I-4

↓ a

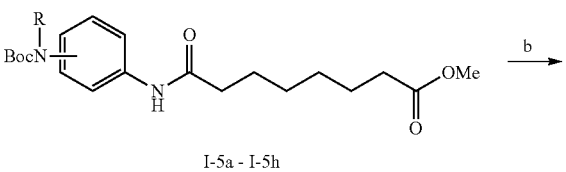
I-5a - I-5h

↓ b

I-6a - I-6h

+

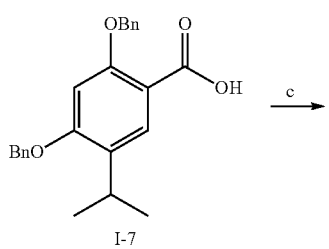
I-7

→ c

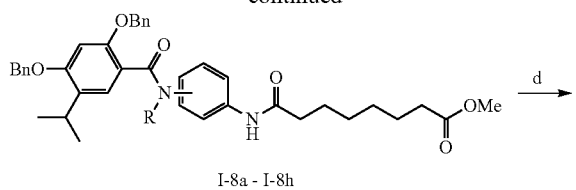

I-8a - I-8h

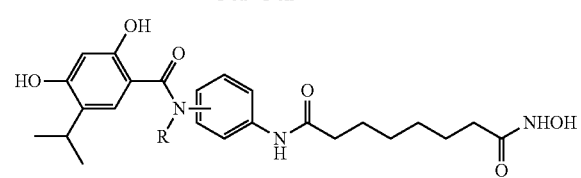

| Position | R |
|---|---|
| G-9: Para | H |
| G-10: Para | CH₃ |
| G-11: Para | C₂H₅ |
| G-12: Para | CH₃CH₂CH₃ |
| G-13: Meta | H |
| G-14: Meta | CH₃ |
| G-15: Meta | C₂H₅ |
| G-16: Ortho | H |

Reagents and conditions: (a) HOBt, DIPEA, DMF: (b) H2O, Dioxane, Reflux; (c) HOBt, DIPEA, DMF; (d) (i) 1M LiOH (aq), Dioxane, 40° C.; (ii) NH2OBn, EDC, HOBt, NMM, DMF, rt; (iii) Pd/C, MeOH, H2 atmosphere.

Scheme 31

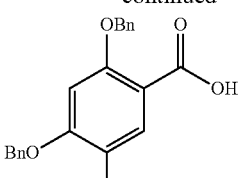

I-7

I-23a: n = 1
I-23b: n = 3

G-17: n = 1
G-18: n = 3

Reagents and conditions: (a) HOBt, DIPEA, DMF; (b) H₂O, Dioxane, Reflux; (c) HOBt, DIPEA, DMF; (d) (i) 1M LiOH (aq), Dioxane, 40° C.; (ii) NH₂OBn, EDC, HOBt, NMM, DMF, rt; (iii) Pd/C, MeOH, H₂ atmosphere.

Scheme 32

I-3b

I-20a: n = 1
I-20b: n = 3

I-21a: n = 1
I-21b: n = 3

I-22a: n = 1
I-22b: n = 3

I-24

I-25

I-26

I-27

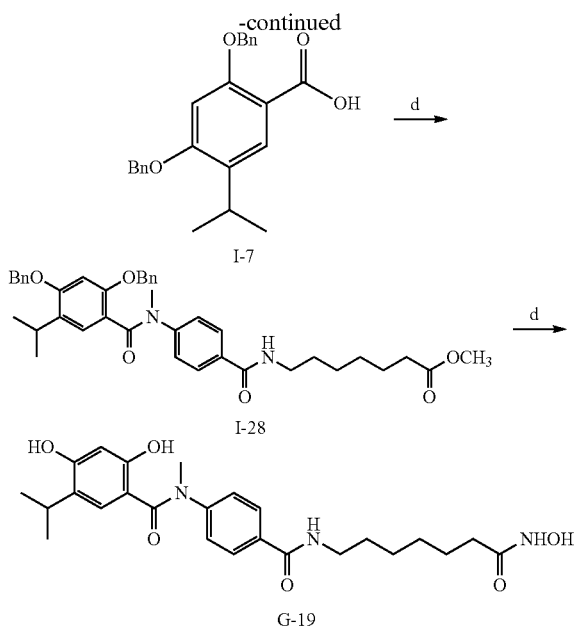

Reagents and conditions: (a) (i) DMAP, TEA, DCM; (ii) Methyl idodide, NaH, DMF, 0° C. to rt; (iii) 1M LiOH (aq), Dioxane, 40° C.; (b) HOBt, DIPEA, DMF; (c) H₂O, Dioxane, Reflux; (d) HOBt, DIPEA, DMF: (d) (i) 1M LiOH (aq), Dioxane, 40° C.; (ii) NH₂OBn, EDC, HOBt, NMM, DMF, rt; (iii) Pd/C, MeOH, H₂ atmosphere.

The compounds of formula (I) thus synthesized were purified by a method such as column chromatography, high-pressure liquid chromatography, or recrystallization.

The intermediates used in the synthesis described above were either commercially available or could be prepared by methods known in the art. The methods could also include additional steps, either before or after the steps described specifically herein, to add or remove suitable protecting groups if necessary to facilitate synthesis of the compounds. In addition, various synthetic steps could be performed in an alternate sequence or order to give the desired compounds.

Below are materials and methods used for preparing and testing the substituted aromatic compounds described above.

Chemical Materials and Analysis

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

Cell Culture

Human cancer cells were purchased from the American Type Culture Collection (Manassas, Va., USA). These cell lines were cultured in RPMI 1640 medium or DMEM supplemented with 10% FBS (v/v) and pencillin (100 U/mL)/streptomycin (100 ug/mL)/amphotericin B (0.25 ug/mL). Cultures were maintained at 37° C. in a humidified atmosphere of 5% CO2/95% air.

Sulforhodamine B (SRB) Assay

Cells were seeded in 96-well plates in medium with 5% fetal bovine serum. After 24 h, cells were fixed with 10% trichloroacetic acid to represent cell population at the time of drug addition (T0). After additional incubation of DMSO or drugs for 48 h, cells were fixed with 10% trichloroacetic acid and sulforhodamine B at 0.4% (w/v) in 1% acetic acid was added to stain cells. Unbound sulforhodamine B was washed out by 1% acetic acid and sulforhodamine B-bound cells were solubilized with 10 mmol/L Trizma base. The absorbance was read at a wavelength of 515 nm. Using the following absorbance measurements, such as time zero (T0), control growth (C), and cell growth in the presence of the drug (Tx), the percentage growth was calculated at each of the compound concentrations levels. Percentage growth inhibition was calculated as 100−[(Tx−70)/(C−70)]×100. Growth inhibition of 50% (GI50) was determined at the drug concentration that results in 50% reduction of total protein increase in control cells during the compound incubation.

HSP90 ATP-Binding Assay and Competition Assays

To assess the inhibition of HSP90 activity within a cellular context, cells were treated with certain substituted aromatic compounds of formula (I) and the inhibition of HSP90 ATP-binding activity in cells was determined by using an ATP pull-down assay. Cells were treated with the compounds for 24 hours and then lysed in TNESV buffer (50 mM Tris, 2 mM EDTA, 100 nM NaCl, 1 mM activated sodium orthovanadate, 25 mM NaF, 1% Triton X-100 [pH 7.5]) for 30 min at 4° C. Lysates were spun for 30 min at 12000 rpm at 4° C. Protein (200 ug) was incubated with conditioned γ-ATP-polyacrylamide resin in incubation buffer (10 mM Tris-HCl, 50 mM KCl, 5 mM MgCl₂, 20 mM Na₂MoO₄, 0.01% Nonidet P-40) overnight at 4° C., rotating. The resin was then washed four times with incubation buffer. Bound proteins were isolated by boiling with SDS buffer. For the competition studies, fluorescence polarization assays were performed under the following conditions: each 96-well plate contained 5 nM fluorescent GM (geldanamycin), 30 nM HSP90 α protein, and tested inhibitor in a final volume of 100 uL. For each assay, background wells (buffer only), tracer controls (free, fluorescent GMonly), and bound GM controls (fluorescent GM in the presence of HSP90) were included on each assay plate. The fraction of tracer bound to HSP90 was correlated to the mP value and plotted against log 10 values of competitor concentrations. The inhibitor concentration at which 50% of bound GM was displaced was obtained by fitting the data.

Western Blot Assay

Western blot analysis was performed to detect cell apoptotic signaling activated by substituted aromatic compounds of formula (I). Cells were harvested by scraping with lysis buffer (1 mM EGTA, 1 mM EDTA, 150 mM NaCl, 1% Triton X-100, 2.5 mM sodium pyrophosphate, 1 mM PMSF, 1 mM Na3VO4, 1 ug/mL leupeptin, 1 ug/mL aprotinin, 5 mM NaF in 20 mM Tris-HCl buffer, pH 7.5). Cell lysates were centrifuged at 13,000 g for 30 min. Total protein was determined and equal amounts of protein were separated by SDS-PAGE and immunoblotted with specific antibodies. Proteins were visualized by enhanced chemiluminescence (Amersham, Buckinghamshire, UK).

Example 1: Synthesis of Compounds of Formula (I)

1-(2,4-bis(benzyloxy)phenyl)ethanone (43)

A mixture of 1-(2,4-dihydroxyphenyl)ethanone (10 g, 65.77 mmol), benzyl bromide (18 ml, 151.33 mmol), potassium carbonate (28 g, 202.60 mmol) and acetone (250 ml) was refluxed for overnight, the precipitant was filtered. The organic layer was collected and concentrated in vacuo to yield an oily product, and the oily product was added n-hexane and stirred for overnight. The residue was filtered by suction filtration to yield white product and without more purification to afford 43 (20.43 g, 93.42%) as a white solid. $^1$H-NMR (500 MHz, CDCl$_3$): δ 2.55 (s, 3H), 5.09 (s, 2H), 5.11 (s, 2H), 6.62 (m, 2H), 7.38 (m, 10H), 7.84 (d, J=9 Hz, 1H).

2-(2,4-bis(benzyloxy)phenyl)propan-2-ol (44)

A mixture of 43 (20 g, 60.17 mmol) and THF (100 ml) was added methylmagnesium bromide (3M, 33 ml) at 0° C. The reaction was allowed back to room temperature and stirred for 4 h. The reaction was quenched with water at 0° C. The residue was filtered by suction filtration to yield white product and without more purification to afford 44 (16.21 g, 77.30%) as a white solid. $^1$H-NMR (500 MHz, CDCl$_3$): δ 1.53 (s, 3H), 1.59 (s, 3H), 3.98 (s, 1H), 5.04 (s, 2H), 5.10 (s, 2H), 6.54 (m, 1H), 6.67 (d, J=2.5 Hz, 1H), 7.24 (d, 1H), 7.38 (m, 10H).

(((4-isopropyl-1,3-phenylene)bis(oxy))bis(methylene))dibenzene (45)

A mixture of 44 (16 g, 45.92 mmol) and CHCl$_2$ (125 ml) was added triethylsilane (9 ml, 56.35 mmol) and TFA (4.5 ml, 58.77 mmol) at −78° C. The reaction was allowed back to room temperature and stirred for 4 h. The reaction was quenched with 1N NaOH (aq.) and extracted with CH$_2$Cl$_2$ (30 ml*3). The organic layer was collected and dried over anhydrous MgSO$_4$ concentrated in vacuo to yield colorless oil product. The residue was purified by silica gel chromatography (ethyl acetate:n-hexane=1:19, Rf=0.35) to afford 45 (14.06 g, 92.08%) as a white solid. $^1$H-NMR (500 MHz, CDCl$_3$): δ 1.25 (d, J=6.5 Hz, 6H), 3.37 (Sep, J=7 Hz, 1H), 5.05 (s, 2H), 5.07 (s, 2H), 6.59 (m, 1H), 6.63 (d, J=2.5 Hz, 1H), 7.16 (d, J=8.5 Hz, 1H), 7.42 (m, 10H).

2,4-bis(benzyloxy)-5-isopropylbenzaldehyde (46)

A mixture of POCl$_3$ (3.3 ml, 35.40 mmol) and DMF (2.7 ml) was stirred at 0° C. for 10 min then added 45 (4 g, 12.03 mmol) dissolved in DMF (3 ml). The reaction was heated at 80° C. and stirred for 1.5 h. The reaction was quenched with 6N NaOH (aq.) and extracted with ethyl acetate (30 ml*3). The organic layer was collected and dried over anhydrous MgSO$_4$ concentrated in vacuo to yield a yellow product. The residue was without more purification to afford 46 (4.01 g, 92.40%) as a yellow solid. $^1$H-NMR (500 MHz, CDCl$_3$): δ 1.21 (d, J=7 Hz, 6H), 3.28 (Sep, J=7 Hz, 1H), 5.10 (s, 2H), 5.12 (s, 2H), 6.50 (s, 1H), 7.37 (m, 10H), 7.74 (s, 1H), 10.39 (s, 1H).

2,4-bis(benzyloxy)-5-isopropylbenzoic acid (47)

A mixture of 46 (3 g, 8.32 mmol), sulfamic acid (6.5 g, 66.94 mmol), DMSO (2 ml), THF (20 ml) and water (20 ml) was added NaClO$_2$ (6 g, 66.34 mmol) dissolved in water (20 ml) at 0° C. The reaction was allowed back to room temperature and stirred for 2 h. The residue was extracted with ethyl acetate (40 ml*3) and purified by silica gel chromatography (ethyl acetate:n-hexane=1:4, Rf=0.25) to afford 47 (2.02 g, 64.61%) as a yellow solid. $^1$H-NMR (500 MHz, CDCl$_3$): δ 1.23 (d, J=7 Hz, 6H), 2.98 (s, 1H), 3.30 (Sep, J=7 Hz, 1H), 5.10 (s, 2H), 5.20 (s, 2H), 6.57 (s, 1H), 7.39 (m, 10H), 8.03 (s, 1H).

N-benzyl-2,4-bis(benzyloxy)-5-isopropylbenzamide (48)

A mixture of 47 (2 g, 5.31 mmol), EDC.HCl (1.5 g, 7.85 mmol), HOBt (0.9 g, 6.67 mmol), NMM (1.4 ml, 12.75 mmol) and DMF (8 ml) was stirred for 10 min then added benzylamine (0.7 ml, 6.53 mmol) at room temperature for overnight, the reaction was quenched with water and extracted with ethyl acetate (30 ml*3). The organic layer was collected and dried over anhydrous MgSO$_4$ concentrated in vacuo to yield colorless oil product. The residue was purified by silica gel chromatography (ethyl acetate:n-hexane=1:3, Rf=0.6) to afford 48 (2.05 g, 83.00%) as a white solid. $^1$H-NMR (500 MHz, CDCl$_3$): δ 1.25 (d, J=6.5 Hz, 6H), 3.33 (Sep, J=7 Hz, 1H), 4.54 (d, J=5.5 Hz, 2H), 5.03 (s, 2H), 5.10 (s, 2H), 6.54 (s, 1H), 7.34 (m, 15H), 8.16 (s, 2H).

2,4-bis(benzyloxy)-N-(2-fluorobenzyl)-5-isopropylbenzamide (49)

A mixture of 47 (2.52 g, 6.69 mmol), EDC.HCl (2 g, 10.47 mmol), HOBt (1.1 g, 8.15 mmol), NMM (2 ml, 18.19 mmol) and DMF (8 ml) was stirred for 10 min then added 2-fluorobenzylamine (1 g, 8 mmol) for overnight, the reaction was quenched with water and extracted with ethyl acetate (30 ml*3). The organic layer was collected and dried over anhydrous MgSO$_4$ concentrated in vacuo to yield colorless oil product. The residue was purified by silica gel chromatography (ethyl acetate:n-hexane=1:4, Rf=0.3) to afford 49 (2.54 g, 78.40%) as a white solid. $^1$H-NMR (500 MHz, CDCl$_3$): δ 1.24 (d, J=7 Hz, 6H), 3.32 (Sep, J=7 Hz, 1H), 4.59 (d, J=6 Hz, 2H), 5.07 (s, 2H), 5.09 (s, 2H), 6.54 (s, 1H), 7.0 (m, 2H), 7.20 (m, 11H), 8.13 (s, 1H), 8.23 (s, 1H).

2,4-bis(benzyloxy)-N-(3-fluorobenzyl)-5-isopropylbenzamide (50)

A mixture of 47 (2.7 g, 7.17 mmol), EDC.HCl (2.1 g, 10.99 mmol), HOBt (1.2 g, 8.89 mmol), NMM (2 ml, 18.19 mmol) and DMF (8 ml) was stirred for 10 min then added 3-fluorobenzylamine (1.07 g, 8.57 mmol) for overnight, the reaction was quenched with water and extracted with ethyl acetate (30 ml*3). The organic layer was collected and dried over anhydrous MgSO$_4$ concentrated in vacuo to yield colorless oil product. The residue was purified by silica gel chromatography (ethyl acetate:n-hexane=1:4, Rf=0.5) to afford 50 (2.89 g, 83.29%) as a white solid. $^1$H-NMR (500 MHz, CDCl$_3$): δ 1.25 (d, J=7.5 Hz, 6H), 3.34 (Sep, J=7 Hz, 1H), 4.51 (d, J=5.5 Hz, 2H), 5.05 (s, 2H), 5.11 (s, 2H), 6.57 (s, 1H), 6.90 (m, 2H), 6.95 (d, J=8 Hz, 1H), 7.18 (m, 1H), 7.31 (m, 10H), 8.17 (s, 1H), 8.20 (t, J=5.5 Hz, 1H).

2,4-bis(benzyloxy)-N-(3-fluorobenzyl)-5-isopropyl-benzamide (51)

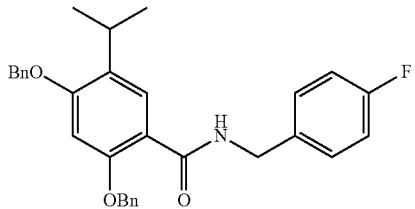 [SMILES: CC(C)c1cc(C(=O)NCc2ccc(F)cc2)c(OCc2ccccc2)cc1OCc1ccccc1]

A mixture of 47 (2.6 g, 6.90 mmol), EDC.HCl (2 g, 10.47 mmol), HOBt (1.2 g, 8.89 mmol), NMM (2 ml, 18.19 mmol) and DMF (8 ml) was stirred for 10 min then added 4-fluorobenzylamine (1 g, 8 mmol) for overnight. The reaction was quenched with water and extracted with ethyl acetate (30 ml*3). The organic layer was collected and dried over anhydrous $MgSO_4$ concentrated in vacuo to yield colorless oil product. The residue was purified by silica gel chromatography (ethyl acetate:n-hexane=1:2, Rf=0.5) to afford 51 (2.76 g, 82.63%) as a white solid. $^1$H-NMR (500 MHz, $CDCl_3$): δ 1.25 (d, J=6.5 Hz, 6H), 3.33 (m, 1H), 4.48 (d, J=5.5 Hz, 2H), 5.02 (s, 2H), 5.10 (s, 2H), 6.55 (s, 1H), 6.89 (m, 2H), 7.10 (m, 2H), 7.34 (m, 11H), 8.14 (s, 1H).

N-benzyl-2,4-dihydroxy-5-isopropylbenzamide (1a)

A mixture of 48 (0.42 g, 0.90 mmol), 10% palladium on activated carbon (0.04 g, 0.04 mmol) and MeOH (8 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.4) to afford 1a (0.23 g, 88.46%) as a white solid. m.p. 142.5-144.8. $^1$H-NMR (500 MHz, MeOD): δ 1.19 (d, J=7 Hz, 6H), 3.17 (Sep, =7 Hz, 1H), 4.52 (s, 2H), 6.31 (s, 1H), 7.19 (t, J=7 Hz, 1H), 7.27 (m, 4H), 7.58 (s, 1H).

N-benzyl-2,4-dihydroxy-5-isopropyl-N-methylbenzamide (1b)

A mixture of 48 (0.38 g, 0.82 mmol), NaH (0.04 g, 1 mmole) and DMF (4 ml) was added methyl iodide (0.1 ml, 1.61 mmol) at room temperature for 2 h. The reaction was quenched with water and extracted with ethyl acetate (30 ml*3). The organic layer was collected and dried over anhydrous $MgSO_4$ concentrated in vacuo and purified by silica gel chromatography (ethyl acetate:n-hexane=1:3, Rf=0.5) to get the oily product, then the oily product was dissolved in MeOH (8 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.4) to afford 1b (0.17 g, 68%) as a white solid. m.p. 133.7-135.4. $^1$H-NMR (500 MHz, MeOD): δ 1.10 (d, J=7 Hz, 6H), 2.93 (s, 3H), 3.13 (Sep, J=7 Hz, 1H), 4.63 (s, 2H), 6.34 (s, 1H), 6.99 (s, 1H), 7.28 (m, 5H).

N-benzyl-N-ethyl-2,4-dihydroxy-5-isopropylbenzamide (1c)

The title compound was prepared using a mixture of 48 (0.35 g, 0.75 mmol), NaH (0.04 g, 1 mmole) and DMF (4 ml) and similar process as mentioned herein afford 1c (0.17 g, 70.83%) as a white solid. m.p. 117.9-119.8. $^1$H-NMR (500 MHz, MeOD): δ 1.09 (m, 9H), 3.13 (Sep, =7 Hz, 1H), 3.36 (m, 2H), 4.65 (s, 2H), 6.34 (s, 1H), 6.94 (s, 1H), 7.27 (m, 5H).

N-benzyl-2,4-dihydroxy-5-isopropyl-N-propylbenzamide (1d)

The title compound was prepared using a mixture of 48 (0.40 g, 0.86 mmol), NaH (0.04 g, 1 mmole) and DMF (4 ml) and similar process as mentioned herein to afford 1d (0.19 g, 67.86%) as a white solid. m.p. 158.6-160.6. $^1$H-NMR (500 MHz, MeOD): δ 0.80 (s, 3H), 1.09 (d, J=7 Hz, 6H), 1.57 (6, J=7 Hz, 2H), 3.14 (Sep, J=7 Hz, 1H), 3.26 (m, 2H), 4.64 (s, 2H), 6.35 (s, 1H), 6.94 (s, 1H), 7.27 (m, 5H).

N-(2-fluorobenzyl)-2,4-dihydroxy-5-isopropylbenzamide (2a)

The title compound was prepared using a mixture of 49 (0.32 g, 0.66 mmol), 10% palladium on activated carbon (0.04 g, 0.04 mmol) and MeOH (8 ml) and similar process as mentioned herein to afford 2a (0.17 g, 85.0%) as a colorless oil. $^1$H-NMR (500 MHz, MeOD): δ 1.19 (d, J=7 Hz, 6H), 3.17 (Sep J=7 Hz, 1H), 4.59 (s, 2H), 6.30 (s, 1H), 7.06 (m, 2H), 7.27 (m, 1H), 7.35 (m, 1H), 7.60 (s, H).

N-(2-fluorobenzyl)-2,4-dihydroxy-5-isopropyl-N-methylbenzamide (2b)

The title compound was prepared using a mixture of 49 (0.38 g, 0.79 mmol), NaH (0.04 g, 1 mmole) and DMF (4 ml) and similar process as mentioned herein to afford 2b (0.16 g, 64.0%) as a white solid. m.p. 92.3-94.3. $^1$H-NMR (500 MHz, MeOD): δ 1.10 (d, J=7 Hz, 6H), 2.97 (s, 3H), 3.13 (Sep, J=7 Hz, 1H), 4.70 (s, 2H), 6.34 (s, 1H), 6.97 (s, 1H), 7.07 (t, J=9 Hz, 1H), 7.15, (t, J=7 Hz, 1H), 7.28 (m, 1H), 7.36 (s, 1H).

N-ethyl-N-(2-fluorobenzyl)-2,4-dihydroxy-5-isopropylbenzamide (2c)

The title compound was prepared using a mixture of 49 (0.30 g, 0.62 mmol), NaH (0.04 g, 1 mmole) and DMF (4 ml) and similar process as mentioned herein to afford 2c (0.14 g, 66.67%) as a white solid. m.p. 113.2-114.6. $^1$H-NMR (500 MHz, MeOD): δ 1.1 (m, 9H), 3.13 (Sep, J=7 Hz, 1H), 3.38 (d, J=7 Hz, 2H), 4.70 (s, 2H), 6.36 (s, 1H), 6.93 (s, 1H), 7.04 (t, J=9 Hz, 1H), 7.12 (t, J=8 Hz, 1H), 7.26 (m, 1H), 7.39 (s, 1H).

N-(2-fluorobenzyl)-2,4-dihydroxy-5-isopropyl-N-propylbenzamide (2d)

The title compound was prepared using a mixture of 49 (0.39 g, 0.81 mmol), NaH (0.04 g, 1 mmole) and DMF (4 ml) and similar process as mentioned herein to afford 2d (0.17 g, 60.71%) as a white solid. m.p. 126.9-127.8. $^1$H-NMR (500 MHz, MeOD): δ 0.81 (s, 3H), 1.10 (d, J=6.5 Hz, 6H), 1.58 (m, 2H), 3.14 (hept, J=7 Hz, 1H), 3.30 (s, 2H), 4.69 (s, 2H), 6.34 (s, 1H), 6.92 (s, 1H), 7.05 (t, J=9 Hz, 1H), 7.13 (t, J=7 Hz, 1H), 7.27 (m, 1H), 7.38 (s, 1H).

N-(3-fluorobenzyl)-2,4-dihydroxy-5-isopropylbenzamide (3a)

The title compound was prepared using 50 and similar process as mentioned herein to afford 3a (0.18 g, 94.74%) as a colorless oil. ¹H-NMR (500 MHz, MeOD): δ 1.20 (d, J=6.5 Hz, 6H), 3.18 (Sep, J=7 Hz, 1H), 4.54 (s, 2H), 6.28 (s, 1H), 6.95 (m, 1H), 7.05 (m, 1H), 7.14 (d, J=7.5 Hz, 1H), 7.31 (m, 1H), 7.56 (s, 1H).

N-(3-fluorobenzyl)-2,4-dihydroxy-5-isopropyl-N-methylbenzamide (3b)

The title compound was prepared using a mixture of 50 (0.39 g, 0.81 mmol), NaH (0.04 g, 1 mmole) and DMF (4 ml) and similar process as mentioned herein to afford 3b (1.8 g, 69.23%) as a pink solid. m.p. 149.8-150.7. ¹H-NMR (500 MHz, MeOD): δ 1.11 (d, J=7 Hz, 6H), 2.95 (s, 3H), 3.13 (t, J=7 Hz, 1H), 4.66 (s, 2H), 6.33 (s, 1H), 6.99 (m, 2H), 7.10 (m, 2H), 7.34 (m, 1H).

N-ethyl-N-(3-fluorobenzyl)-2,4-dihydroxy-5-isopropylbenzamide (3c)

The title compound was prepared using a mixture of 50 (0.33 g, 0.68 mmol), NaH (0.04 g, 1 mmole) and DMF (4 ml) and similar process as mentioned herein to afford 3c (0.16 g, 69.57%) as a white solid. m.p. 118.1-118.9. ¹H-NMR (500 MHz, CDCl₃): δ 0.94 (d, J=6.5 Hz, 6H), 1.27 (t, J=7 Hz, 3H), 2.38 (s, 1H), 3.04 (hept, J=7 Hz, 1H), 3.49 (q, J=7 Hz, 2H), 4.71 (s, 2H), 6.38 (s, 1H), 7.00 (m, 5H), 7.34 (m, 1H), 10.16 (s, 1H).

N-(3-fluorobenzyl)-2,4-dihydroxy-5-isopropyl-N-propylbenzamide (3d)

The title compound was prepared using a mixture of 50 (0.38 g, 0.79 mmol), NaH (0.04 g, 1 mmole) and DMF (4 ml) and similar process as mentioned herein to afford 3d (0.17 g, 62.96%) as a colorless oil. ¹H-NMR (500 MHz, CDCl₃): δ 0.91 (t, J=7.5 Hz, 3H), 0.97 (d, J=7 Hz, 6H), 1.75 (m, 2H), 3.03 (qui, J=7 Hz, 1H), 3.38 (m, 2H), 4.73 (s, 2H), 5.38 (s, 1H), 6.37 (s, 1H), 7.01 (m, 2H), 7.08 (m, 2H), 7.37 (m, 1H), 10.35 (s, 1H).

N-(4-fluorobenzyl)-2,4-dihydroxy-5-isopropylbenzamide (4a)

The title compound was prepared using a mixture of 51 (0.3 g, 0.62 mmol), 10% palladium on activated carbon (0.04 g, 0.04 mmol) and MeOH (7 ml) and similar process as mentioned herein to afford 4a (0.17 g, 89.47%) as a colorless oil. ¹H-NMR (500 MHz, MeOD): δ 1.18 (d, J=7 Hz, 6H), 3.16 (Sep, J=7 Hz, 1H), 4.49 (s, 2H), 6.29 (s, 1H), 6.99 (t, J=9 Hz, 2H), 7.31 (m, 2H), 7.56 (s, 1H).

N-(4-fluorobenzyl)-2,4-dihydroxy-5-isopropyl-N-methylbenzamide (4b)

The title compound was prepared using a mixture of 51 (0.33 g, 0.68 mmol), NaH (0.04 g, 1 mmol) and DMF (4 ml) and similar process as mentioned herein to afford 4b (0.15 g, 68.18%) as a colorless oil. ¹H-NMR (500 MHz, MeOD): δ 1.12 (d, J=7 Hz, 6H), 2.92 (s, 3H), 3.14 (hept, J=7 Hz, 1H), 4.62 (s, 2H), 6.33 (s, 1H), 6.97 (s, 1H), 7.05 (t, J=9 Hz, 2H), 7.31 (m, 2H).

N-ethyl-N-(4-fluorobenzyl)-2,4-dihydroxy-5-isopropylbenzamide (4c)

The title compound was prepared using a mixture of 51 (0.37 g, 0.77 mmol), NaH (0.04 g, 1 mmol) and DMF (4 ml) and similar process as mentioned herein to afford 4c (0.17 g, 65.38%) as a colorless oil. ¹H-NMR (500 MHz, MeOD): δ 1.09 (m, 9H), 3.14 (qui, J=7 Hz, 1H), 3.25 (m, 2H), 4.63 (s, 2H), 6.35 (s, 1H), 6.93 (s, 1H), 7.02 (m, 2H), 7.31 (m, 2H).

N-(4-fluorobenzyl)-2,4-dihydroxy-5-isopropyl-N-propylbenzamide (4d)

The title compound was prepared using a mixture of 51 (0.40 g, 0.83 mmol), NaH (0.04 g, 1 mmol) and DMF (4 ml) and similar process as mentioned herein to afford 4d (0.18 g, 62.07%) as a white solid. m.p. 103.2-103.9. ¹H-NMR (500 MHz, MeOD): δ 0.79 (s, 3H), 1.10 (d, J=7 Hz, 6H), 1.56 (6, J=7 Hz, 2H), 3.14 (Sep, J=7 Hz, 1H), 3.26 (m, 2H), 4.62 (s, 2H), 6.35 (s, 1H), 6.92 (s, 1H), 7.03 (t, J=9 Hz, 2H), 7.30 (s, 2H).

N-benzylpropan-2-amine (55)

The title compound was prepared using a mixture of benzylamine (3 g, 28.00 mmol), acetone (2.3 ml, 31.32 mmol), MeOH (15 ml) and acetic acid (cat.) and similar process as mentioned herein to afford 55 (1.8 g, 43.06%) as a colorless oil. ¹H-NMR (500 MHz, CDCl₃): δ 1.10 (d, J=6.5 Hz, 6H), 2.92 (Sep, J=6.5 Hz, 1H), 3.75 (s, 2H), 7.22 (m, 5H).

N-(3-fluorobenzyl)propan-2-amine (56)

The title compound was prepared using a mixture of 3-fluorobenzylamine (2 g, 11.96 mmol), acetone (1 ml, 13.62 mmol), MeOH (14 ml) and acetic acid (cat.) and similar process as mentioned herein to afford 56 (0.87 g, 43.50%) as a oily product. ¹H-NMR (500 MHz, CDCl₃): δ 1.08 (d, J=6.5 Hz, 6H), 2.83 (Sep, J=6.5 Hz, 1H), 3.76 (s, 2H), 6.90 (m, 1H), 7.04 (m, 2H), 7.24 (m, 1H).

N-(4-fluorobenzyl)propan-2-amine (57)

The titled compound was prepared using a mixture of 4-fluorobenylamine (2 g, 11.96 mmol), acetone (1 ml, 13.62 mmol), MeOH (15 ml) and acetic acid (cat.) and similar process as mentioned herein to afford 57 (0.81 g, 40.50%) as a oily product. ¹H-NMR (500 MHz, CDCl₃): δ 1.08 (d, J=6.5 Hz, 6H), 2.83 (Sep, J=6.5), 3.72 (s, 2H) 6.98 (m, 2H), 7.26 (m, 2H).

N-benzyl-2,4-dihydroxy-N,5-diisopropylbenzamide (1e)

The title compound was prepared using a mixture of 47 (0.6 g, 1.59 mmol), EDC.HCl (0.45 g, 2.36 mmol), HOBt (0.3 g, 2.22 mmol), NMM (0.5 ml, 4.5 mmol) and DMF (3 ml) and similar process as mentioned herein to afford 1e (0.37 g, 71.15%) as a white solid. m.p. 176.1-178.0. ¹H-NMR (500 MHz, MeOD): δ 1.12 (m, 12H), 3.14 (qui, J=7 Hz, 1H), 4.26 (m, 1H), 4.64 (s, 2H), 6.34 (s, 1H), 6.92 (s, 1H), 7.18 (t, J=7 Hz, 1H), 7.27 (m, 2H), 7.34 (d, J=7.5 Hz, 2H).

N-(3-fluorobenzyl)-2,4-dihydroxy-N,5-diisopropylbenzamide (3e)

The title compound was prepared using a mixture of 47 (0.5 g, 1.33 mmol), EDC.HCl (0.4 g, 2.09 mmol), HOBt (0.25 g, 1.85 mmol), NMM (0.5 ml, 4.5 mmol) and DMF (3 ml) and similar process as mentioned herein to afford 3e (0.32 g, 73.91%) as a white solid. m.p. 164.3-165.1. ¹H-NMR (500 MHz, MeOD): δ 1.14 (d, J=7 Hz, 12H), 3.16 (Sep, J=7 Hz, 1H), 4.25 (s, 1H), 4.66 (s, 2H), 6.35 (s, 1H), 6.91 (m, 2H), 7.17 (m, 2H), 7.29 (m, 1H).

N-(4-fluorobenzyl)-2,4-dihydroxy-N,5-diisopropyl-benzamide (4e)

The title compound was prepared using a mixture of 47 (0.5 g, 1.33 mmol), EDC.HCl (0.4 g, 2.09 mmol), HOBt (0.25 g, 1.85 mmol), NMM (0.5 ml, 4.5 mmol) and DMF (3 ml) and similar process as mentioned herein to afford 4e (0.31 g, 67.39%) as a white solid. m.p. 195.9-197.1. ¹H-NMR (500 MHz, MeOD): δ 1.12 (d, J=7 Hz, 12H), 3.14 (Sep, J=7 Hz, 1H), 4.24 (s, 1H), 4.61 (s, 2H), 6.34 (s, 1H), 6.90 (s, 1H), 6.99 (m, 2H), 7.36 (m, 2H).

2,4-bis(benzyloxy)-5-isopropyl-N-phenylbenzamide (58)

The title compound was prepared using a mixture of 47 (2.8 g, 7.44 mmol), EDC.HCl (2.3 g, 12.04 mmol), HOBt (1.5 g, 11.11 mmol), NMM (2 ml, 18.19 mmol) and DMF (7 ml) and similar process as mentioned herein to afford 58 (2.71 g, 80.65%) as a colorless oil product. ¹H-NMR (500 MHz, CDCl₃): δ 1.27 (d, J=6.5 Hz, 6H), 3.35 (qui, J=7 Hz, 1H), 5.15 (s, 2H), 5.16 (s, 2H), 6.62 (s, 1H), 7.15 (t, J=7.5 Hz, 1H), 7.39 (m, 14H), 8.20 (s, 1H), 9.85 (s, 1H).

2,4-bis(benzyloxy)-N-(2-fluorophenyl)-5-isopropyl-benzamide (59)

The title compound was prepared using a mixture of 47 (2.6 g, 6.91 mmol), EDC.HCl (2 g, 10.47 mmol), HOBt (1.3 g, 9.63 mmol), NMM (2 ml, 18.19 nnol) and DMF and similar process as mentioned herein to afford 59 (2.40 g, 74.07%) as a white solid. ¹H-NMR (500 MHz, CDCl₃): δ 1.25 (d, J=7 Hz, 6H), 3.32 (qui, J=7 Hz, 1H), 5.07 (s, 2H), 5.22 (s, 2H), 6.56 (s, 1H), 7.28 (m, 13H), 8.17 (s, 1H), 8.55 (t, J=8 Hz, 1H), 10.19 (s, 1H).

2,4-bis(benzyloxy)-N-(3-fluorophenyl)-5-isopropyl-benzamide (60)

The title compound was prepared using a mixture of 47 (2 g, 5.31 mmol), EDC.HCl (1.5 g, 7.85 mmol), HOBt (1 g, 7.41 mmol), NMM (1.5 ml, 13.64 mmol) and DMF (6 ml) and similar process as mentioned herein to afford 60 (2.03 g, 81.53%) as a white solid. ¹H-NMR (500 MHz, CDCl₃): δ 1.26 (d, =6.5 Hz, 6H), 3.35 (qui, =7 Hz, 1H), 5.14 (s, 2H), 5.17 (s, 2H), 6.62 (s, 1H), 6.68 (m, 1H), 6.78 (m, 1H), 7.08 (m, H), 7.21 (m, 1H), 7.47 (m, 10H), 8.18 (s, 1H), 9.93 (s, 1H).

2,4-bis(benzyloxy)-N-(4-fluorophenyl)-5-isopropyl-benzamide (61)

The title compound was prepared using a mixture of 47 (2 g, 5.31 mmol), EDC.HCl (1.5 g, 7.85 mmol), HOBt (0.9 g, 6.67 mmol), NMM (1.5 ml, 13.64 mmol) and DMF (8 ml) and similar process as mentioned herein to afford 61 (1.89 g, 75.90%) as a white solid. ¹H-NMR (500 MHz, CDCl₃): δ 1.26 (d, =7 Hz, 6H), 3.35 (Sep, J=7 Hz, 1H), 5.14 (s, 2H), 5.16 (s, 2H), 6.62 (s, 1H), 6.88 (t, =8.5 Hz, 2H), 7.20 (m, 2H), 7.44 (m, 10H), 8.18 (s, 1H), 9.84 (s, 1H).

2,4-bis(benzyloxy)-5-isopropyl-N-(3,4,5-trimethoxy-phenyl)benzamide (62)

The title compound was prepared using a mixture of 47 (3 g, 7.97 mmol), EDC.HCl (2.4 g, 12.57 mmol), HOBt (1.4 g, 10.37 mmol), NMM (2.5 ml, 22.74 mmol) and DMF (10 ml) and similar process as mentioned herein to afford 62 (3.09 g, 71.53%) as a white solid. ¹H-NMR (500 MHz, CDCl₃): δ 1.27 (d, J=6.5 Hz, 6H), 3.37 (qui, J=7 Hz, 1H) 3.69 (s, 6H), 3.77 (s, 3H), 5.13 (s, 2H), 5.19 (s, 2H), 6.63 (s, 2H), 6.66 (s, 1H), 7.43 (m, 10H), 8.21 (s, 1H), 9.82 (s, 1H).

2,4-bis(benzyloxy)-5-isopropyl-N-(4-morpholino-phenyl)benzamide (63)

The title compound was prepared using a mixture of 47 (2.2 g, 5.84 mmol), EDC.HCl (1.7 g, 8.9 mmol), HOBt (1 g, 7.41 mmol), NMM (1.5 ml, 13.64 mmol) and DMF (7 ml) and similar process as mentioned herein to afford 63 (2.52 g, 80.51%) as a white solid. ¹H-NMR (500 MHz, CDCl₃): δ 1.26 (d, =7 Hz, 6H), 3.08 (t, J=5 Hz, 4H), 3.35 (qui, J=7 Hz, 1H), 3.84 (t, =5 Hz, 4H), 5.14 (s, 2H), 5.15 (s, 2H), 6.61 (s, 1H), 6.77 (d, =9 Hz, 2H), 7.20 (d, =9 Hz, 2H), 7.45 (m, 10H), 8.20 (s, 1H), 9.74 (s, 1H).

2,4-dihydroxy-5-isopropyl-N-phenylbenzamide (5a)

The title compound was prepared using a mixture of 58 (0.3 g, 0.66 mmol), 10% palladium on activated carbon (0.04 g, 0.04 mmol) and MeOH (7 ml) and similar process as mentioned herein to afford 5a (0.16 g, 88.89%) as a white solid. 197.1-198.9. ¹H-NMR (500 MHz, MeOD): δ 1.24 (d, J=7 Hz, 6H), 3.20 (Sep, J=7 Hz, 1H), 6.34 (s, 1H), 7.13 (m, 1H), 7.33 (m, 2H), 7.60 (m, 2H), 7.75 (s, 1H).

2,4-dihydroxy-5-isopropyl-N-methyl-N-phenylbenz-amide (5b)

The title compound was prepared using a mixture of 58 (0.33 g, 0.73 mmol), NaH (0.04 g, 1 mmole) and DMF (3 ml) and similar process as mentioned herein to afford 5b (0.15 g, 71.42%) as a white solid. m.p. 126.8-128.0. ¹H-NMR (500 MHz, MeOD): δ 0.76 (d, J=7 Hz, 6H), 2.89 (Sep, J=7 Hz, 1H), 3.40 (s, 1H), 6.19 (s, 1H), 6.58 (s, 1H) 7.16 (m, 2H), 7.21 (m, 1H), 7.32 (m, 2H).

N-ethyl-2,4-dihydroxy-5-isopropyl-N-phenylbenz-amide (5c)

1 The title compound was prepared using a mixture of 58 (0.36 g, 0.80 mmol), NaH (0.04 g, 1 mmole) and DMF (3 ml) and similar process as mentioned herein to afford 5c (0.17 g, 70.83%) as a white solid. m.p. 143.2-144.3. ¹H-NMR (500 MHz, MeOD): δ 0.75 (d, J=7 Hz, 6H), 1.17 (t, J=7 Hz, 3H), 2.88 (Sep, J=7 Hz, 1H), 3.90 (q, J=7 Hz, 2H), 6.19 (s, 1H), 6.57 (s, 1H), 7.14 (m, 2H), 7.22 (m, 1H), 7.32 (m, 2H).

2,4-dihydroxy-5-isopropyl-N-phenyl-N-propylbenz-amide (5d)

The title compound was prepared using a mixture of 58 (0.34 g, 0.75 mmol), NaH (0.04 g, 1 mmole) and DMF (3 ml) and similar process as mentioned herein to afford 5d (0.15 g, 62.50%) as a white solid. m.p. 119.8-120.6. ¹H-NMR (500 MHz, MeOD): δ 0.76 (d, J=6.5 Hz, 6H), 0.91

(t, J=7.5 Hz, 3H), 1.62 (m, 2H), 2.88 (hept, J=7 Hz, 1H), 3.82 (m, 2H), 6.19 (s, 1H), 6.57 (s, 1H), 7.15 (m, 2H), 7.22 (m, 1H), 7.31 (m, 2H).

2,4-dihydroxy-N,5-diisopropyl-N-phenylbenzamide (5e)

The title compound was prepared using a mixture of 58 (0.34 g, 0.75 mmol), NaH (0.04 g, 1 mmole) and DMF (3 ml) and similar process as mentioned herein to afford 5e (0.14 g, 58.33%) as a white solid. m.p. 135.8-137.1. ¹H-NMR (500 MHz, MeOD): δ 0.82 (d, J=7 Hz, 6H), 1.17 (d, J=7 Hz, 6H), 2.90 (Sep, J=7 Hz, 1H), 4.95 (Sep, J=7 Hz, 1H), 6.16 (s, 1H), 6.59 (s, 1H), 7.13 (m, 2H), 7.25 (m, 1H), 7.31 (m, 2H).

N-(2-fluorophenyl)-2,4-dihydroxy-5-isopropylbenzamide (6a)

The title compound was prepared using a mixture of 59 (0.34 g, 0.72 mmol), 10% Palladium on activated carbon (0.04 g, 0.04 mmol) and MeOH (7 ml) and similar process as mentioned herein to afford 66a (0.18 g, 85.71%) as a yellow solid. m.p. 67.3-68.2 ¹H-NMR (500 MHz, MeOD): δ 1.22 (d, J=7 Hz, 6H), 3.20 (Sex, J=7 Hz, 1H), 6.39 (s, 1H), 7.13 (m, 3H), 7.81 (s, 1H), 8.14 (m, 1H).

N-(2-fluorophenyl)-2,4-dihydroxy-5-isopropyl-N-methylbenzamide (6b)

The title compound was prepared using a mixture of 59 (0.31 g, 0.66 mmol), NaH (0.04 g, 1 mmole) and DMF (3 ml) and similar process as mentioned herein to afford 6b (0.14 g, 70.0%) as a white solid. m.p. 146.7-147.6. ¹H-NMR (500 MHz, MeOD): δ 0.81 (d, J=7 Hz, 6H), 2.92 (Sep, J=7 Hz, 1H), 3.34 (s, 3H), 6.19 (s, 1H), 6.66 (s, 1H), 7.11 (m, 2H), 7.25 (m, 2H).

N-ethyl-N-(2-fluorophenyl)-2,4-dihydroxy-5-isopropylbenzamide (6c)

The title compound was prepared using a mixture of 59 (0.35 g, 0.75), NaH (0.04 g, 1 mmole) and DMF (3 ml) and similar process as mentioned herein to afford 6c (0.16 g, 66.67%) as a white solid. m.p. 153.1-154.2. ¹H-NMR (500 MHz, MeOD): δ 0.80 (d, J=7 Hz, 6H), 1.16 (t, J=7 Hz, 3H), 2.91 (Sep, J=7 Hz, 1H), 3.85 (q, J=7 Hz, 2H), 6.17 (s, 1H), 6.66 (s, 1H), 7.13 (m, 2H), 7.28 (m, 2H).

N-(2-fluorophenyl)-2,4-dihydroxy-5-isopropyl-N-propylbenzamide (6d)

The title compound was prepared using a mixture of 59 (0.32 g, 0.68 mmol), NaH (0.04 g, 1 mmole) and DMF (3 ml) was added 1-iodopropane (0.1 ml, 1.03 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.4) to get the oily product, then the oily product was dissolved in MeOH (6 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.2) to afford 6d (0.14 g, 60.87%) as a white solid. m.p. 132.1-132.4. ¹H-NMR (500 MHz, MeOD): δ 0.82 (d, J=7 Hz, 6H), 0.92 (t, J=7 Hz, 3H), 1.60 (Sex, J=7.5 Hz, 2H), 2.91 (Sep, J=7, 1H), 3.76 (m, 2H), 6.17 (s, 1H), 6.66 (s, 1H), 7.09 (m, 1H), 7.16 (m, 1H), 7.28 (m, 2H).

N-(2-fluorophenyl)-2,4-dihydroxy-N,5-diisopropylbenzamide (6e)

The title compound was prepared using a mixture of 59 (0.38 g, 0.81 mmol), NaH (0.04 g, 1 mmole) and DMF (3 ml) and similar process as mentioned herein to afford 6e (0.15 g, 55.56%) as a pink solid. m.p. 125.1-126.7. ¹H-NMR (500 MHz, CDCl₃): δ 0.78 (d, J=6.5 Hz, 6H), 1.21 (s, 6H), 2.84 (Sep, J=7 Hz, 1H), 4.97 (qui, J=7 Hz, 1H), 5.98 (s, 1H), 6.28 (s, 1H), 6.61 (s, 1H). 7.05 (m, 1H), 7.14 (m, 1H), 7.21 (m, 1H), 7.27 (m, 1H).

N-(3-fluorophenyl)-2,4-dihydroxy-5-isopropylbenzamide (7a)

The title compound was prepared using a mixture of 60 (0.34 g, 0.72 mmol), 10% palladium on activated carbon (0.04 g, 0.04 mmol) and MeOH (7 ml) and similar process as mentioned herein to afford 7a (0.18 g, 85.71%) as a colorless oil. ¹H-NMR (500 MHz, CDCl₃): δ 1.21 (d, J=7 Hz, 6H), 3.14 (Sep, J=7 Hz, 1H), 6.37 (s, 1H), 6.82 (m, 1H), 7.02 (s, 1H), 7.21 (m, 1H), 7.28 (m, 1H), 7.43 (m, 1H), 8.28 (s, 1H), 11.96 (s, 1H).

N-(3-fluorophenyl)-2,4-dihydroxy-5-isopropyl-N-methylbenzamide (7b)

The title compound was prepared using a mixture of 60 (0.34 g, 0.72 mmol), NaH (0.04 g, 1 mmole) and DMF (3 ml) and similar process as mentioned herein to afford 7b (0.16 g, 72.72%) as a white solid. m.p. 113.4-114.7. ¹H-NMR (500 MHz, MeOD): δ 0.82 (d, J=7 Hz, 6H), 2.94 (Sep, J=7 Hz, 1H), 3.34 (s, 3H), 6.21 (s, 1H), 6.64 (s, 1H), 6.96 (m, 3H), 7.30 (m, 1H).

N-ethyl-N-(3-fluorophenyl)-2,4-dihydroxy-5-isopropylbenzamide (7c)

The title compound was prepared using a mixture of 60 (0.36 g, 0.76 mmol), NaH (0.04 g, 1 mmole) and DMF (3 ml) and similar process as mentioned herein to afford 7c (0.17 g, 70.83%) as a colorless oil. ¹H-NMR (500 MHz, MeOD): δ 0.81 (d, J=7 Hz, 6H), 1.17 (t, J=7 Hz, 3H), 2.93 (Sep, J=7 Hz, 1H), 3.91 (q, J=7 Hz, 2H), 6.20 (s, 1H), 6.62 (s, 1H), 6.97 (m, 3H), 7.31 (m, 1H).

N-(3-fluorophenyl)-2,4-dihydroxy-5-isopropyl-N-propylbenzamide (7d)

The title compound was prepared using a mixture of 60 (0.39 g, 0.83 mmol), NaH (0.04 g, 1 mmole) and DMF (3 ml) and similar process as mentioned herein to afford 7d (0.17 g, 60.71%) as a colorless oil. ¹H-NMR (500 MHz, MeOD): δ 0.83 (d, J=7 Hz, 6H), 0.92 (t, J=7 Hz, 3H), 1.62 (m, 2H), 2.93 (qui, J=7 Hz, 1H), 3.83 (m, 2H), 6.19 (s, 1H), 6.62 (s, 1H), 6.95 (m, 3H), 17.30 (m, 1H).

N-(3-fluorophenyl)-2,4-dihydroxy-N,5-diisopropylbenzamide (7e)

The title compound was prepared using a mixture of 60 (0.39 g, 0.83 mmol), NaH (0.04 g, 1 mmole) and DMF (3 ml) and similar process as mentioned herein to afford 7e (0.17 g, 60.70%) as a white solid. m.p. 138.7-139.5. $^1$H-NMR (500 MHz, MeOD): δ 0.88 (d, J=6.5 Hz, 6H), 1.19 (d, J=7 Hz, 6H), 2.95 (Sep, J=7 Hz, 1H), 4.93 (Sep, J=7 Hz, 1H), 6.17 (s, 1H), 6.64 (s, 1H), 6.94 (m, 2H), 7.01 (m, 1H), 7.30 (m, 1H).

N-(4-fluorophenyl)-2,4-dihydroxy-5-isopropylbenzamide (8a)

The title compound was prepared using a mixture of 61 (0.31 g, 0.66 mmol), 10% palladium on activated carbon (0.04 g, 0.04 mmol) and MeOH (6 ml) and similar process as mentioned herein to afford 8a (0.17 g, 89.47%) as a white solid. m.p. 165.3-166.4. $^1$H-NMR (500 MHz, MeOD): δ 1.23 (d, J=7 Hz, 6H), 3.19 (Sep, J=7 Hz, 1H), 6.33 (s, 1H), 7.07 (m, 2H), 7.60 (m, 2H), 7.73 (s, 1H).

N-(4-fluorophenyl)-2,4-dihydroxy-5-isopropyl-N-methylbenzamide (8b)

The title compound was prepared using a mixture of 61 (0.35 g, 0.75 mmol), NaH (0.04 g, 1 mmole) and DMF (3 ml) and similar process as mentioned herein to afford 8b (0.17 g, 73.91%) as a white solid. m.p. 120.1-121.3. $^1$H-NMR (500 MHz, MeOD): δ 0.82 (d, J=7 Hz, 6H), 2.94 (Sep, J=7 Hz, 1H), 3.37 (s, 3H), 6.20 (s, 1H), 6.60 (s, 1H), 7.04 (m, 2H), 7.17 (m, 2H).

N-ethyl-N-(4-fluorophenyl)-2,4-dihydroxy-5-isopropylbenzamide (8c)

The title compound was prepared using a mixture of 61 (0.34 g, 0.72 mmol), NaH (0.04 g, 1 mmole) and DMF (3 ml) and similar process as mentioned herein to afford 5c (0.17 g, 73.91%) as a white solid. m.p. 121.6-122.3. $^1$H-NMR (500 MHz, MeOD): δ 0.81 (d, J=7 Hz, 6H), 1.16 (t, J=7 Hz, 3H), 2.93 (Sep, J=7 Hz, 1H), 3.87 (q, J=7 Hz, 2H), 6.20 (s, 1H), 6.58 (s, 1H), 7.04 (m, 1H), 7.16 (m, 1H).

N-(4-fluorophenyl)-2,4-dihydroxy-5-isopropyl-N-propylbenzamide (8d)

The title compound was prepared using a mixture of 61 (0.30 g, 0.64 mmol), NaH (0.04 g, 1 mmole) and DMF (3 ml) and similar process as mentioned herein to afford 8d (0.14 g, 66.67%) as a white solid. m.p. 137.6-138.6. $^1$H-NMR (500 MHz, MeOD): δ 0.84 (d, J=7 Hz, 6H), 0.92 (t, J=7.5 Hz, 3H), 1.61 (Sex, J=7.5 Hz, 2H), 2.93 (Sep, J=7 Hz, 1H), 3.80 (m, 2H), 6.17 (s, 1H), 6.58 (s, 1H), 7.05 (m, 2H), 7.17 (m, 2H).

N-(4-fluorophenyl)-2,4-dihydroxy-N,5-diisopropylbenzamide (8e)

The title compound was prepared using a mixture of 61 (0.33 g, 0.70 mmol), NaH (0.04 g, 1 mmole) and DMF (3 ml) and similar process as mentioned herein to afford 8e (0.14 g, 60.87%) as a colorless oil. $^1$H-NMR (500 MHz, CDCl$_3$): δ 0.78 (d, J=7 Hz, 6H), 1.17 (d, J=6.5 Hz, 6H), 2.86 (Sep, =7 Hz, 1H), 5.05 (Sep, =6.5 Hz, 1H), 6.29 (d, J=9.5 Hz, 2H), 6.48 (s, 1H), 7.06 (m, 4H), 11.41 (s, 1H).

2,4-dihydroxy-5-isopropyl-N-(3,4,5-trimethoxyphenyl)benzamide (9a)

The title compound was prepared using a mixture of 62 (0.37 g, 0.68 mmol), 10% palladium on activated carbon (0.04 g, 0.04 mmol) and MeOH (10 ml) and similar process as mentioned herein to afford 9a (0.21 g, 84.0%) as a white solid. m.p. 113.9-115.8. $^1$H-NMR (500 MHz, MeOD): δ 1.24 (d, J=7 Hz, 6H), 3.20 (Sep, J=7 Hz, 1H), 3.74 (s, 3H), 3.83 (s, 6H), 6.34 (s, 1H), 7.02 (s, 2H), 7.73 (s, 1H).

2,4-dihydroxy-5-isopropyl-N-methyl-N-(3,4,5-trimethoxyphenyl)benzamide (9b)

The title compound was prepared using a mixture of 62 (0.38 g, 0.70 mmol), NaH (0.04 g, 1 mmole) and DMF (3 ml) and similar process as mentioned herein to afford 9b (0.17 g, 65.38%) as a white solid. m.p. 163.0-164.8. $^1$H-NMR (500 MHz, MeOD): δ 0.85 (d, J=7 Hz, 6H), 2.96 (Sep, J=7 Hz, 1H), 3.41 (s, 3H), 3.72 (s, 9H), 6.20 (s, 1H), 6.51 (s, 2H), 6.70 (s, 1H).

N-ethyl-2,4-dihydroxy-5-isopropyl-N-(3,4,5-trimethoxyphenyl)benzamide (9c)

The title compound was prepared using a mixture of 62 (0.34 g, 0.63 mmol), NaH (0.04 g, 1 mmole) and DMF (3 ml) and similar process as mentioned herein to afford 9c (0.16 g, 64.0%) as a white solid. m.p. 130.2-131.9. $^1$H-NMR (500 MHz, MeOD): δ 0.84 (d, J=7 Hz, 6H), 1.20 (t, J=7 Hz, 3H), 2.95 (Sep, J=7 Hz, 1H), 3.72 (d, J=3 Hz, 9H), 3.91 (q, J=7 Hz, 2H), 6.19 (s, 2H), 6.68 (s, 1H).

2,4-dihydroxy-5-isopropyl-N-propyl-N-(3,4,5-trimethoxyphenyl)benzamide (9d)

The title compound was prepared using a mixture of 62 (0.37 g, 0.68 mmol), NaH (0.04 g, 1 mmole) and DMF (3 ml) and similar process as mentioned herein to afford 9d (0.17 g, 62.96%) as a white solid. m.p. 168.9-171.2. $^1$H-NMR (500 MHz, MeOD): δ 0.84 (d, J=7 Hz, 6H), 0.94 (t, J=7.5 Hz, 3H), 1.65 (m, 2H), 2.95 (Sep, J=7 Hz, 1H), 3.71 (d, J=4 Hz, 9H), 3.82 (m, 2H), 6.19 (s, 1H), 6.47 (s, 2H), 6.67 (s, 1H).

2,4-dihydroxy-N,5-diisopropyl-N-(3,4,5-trimethoxyphenyl)benzamide (9e)

The title compound was prepared using a mixture of 62 (0.39 g, 0.72 mmol), NaH (0.04 g, 1 mmole) and DMF (3 ml) and similar process as mentioned herein to afford 9e (0.17 g, 58.62%) as a white solid. m.p. 140.5-142.6. $^1$H-NMR (500 MHz, MeOD): δ 0.89 (d, J=7 Hz, 6H), 1.23 (d, J=6.5 Hz, 6H), 2.96 (Sep, J=7 Hz, 1H), 3.72 (s, 3H), 3.74 (s, 6H), 4.95 (qui, J=7 Hz, 1H), 6.17 (s, 1H), 6.45 (s, 2H), 6.70 (s, 1H).

2,4-dihydroxy-5-isopropyl-N-(4-morpholinophenyl)benzamide (10a)

The title compound was prepared using a mixture of 63 (0.31 g, 0.58 mmol), 10% palladium on activated carbon (0.04 g, 0.04 mmol) and MeOH (6 ml) and similar process as mentioned herein to afford 10a (0.18 g, 85.71%) as a white solid. m.p. 202.1-203.6. $^1$H-NMR (500 MHz, MeOD): δ 1.22 (d, J=6.5 Hz, 6H), 3.10 (t, J=5 Hz, 4H), 3.18 (Sep, J=7 Hz, 1H), 3.82 (t, J=5 Hz, 4H), 6.32 (s, 1H) 6.93 (m, 2H), 7.46 (m, 2H), 7.71 (s, 1H).

2,4-dihydroxy-5-isopropyl-N-methyl-N-(4-morpholinophenyl)benzamide (10b)

The title compound was prepared using a mixture of 63 (0.31 g, 0.58 mmol), NaH (0.04 g, 1 mmole) and DMF (3 ml) and similar process as mentioned herein to afford 10b (0.15 g, 71.43%) as a white solid. m.p. 171.1-172.8. $^1$H-NMR (500 MHz, CDCl$_3$): δ 0.73 (d, J=7 Hz, 6H), 2.87 (Sep, J=7 Hz, 1H), 3.11 (t, J=5 Hz, 4H), 3.40 (s, 3H), 3.85 (t, J=5 Hz, 4H), 6.27 (s, 1H), 6.54 (s, 1H), 6.83 (m, 3H), 7.04 (m, 2H), 11.63 (s, 1H).

N-ethyl-2,4-dihydroxy-5-isopropyl-N-(4-morpholinophenyl)benzamide (10c)

The title compound was prepared using a mixture of 63 (0.34 g, 0.63 mmol), NaH (0.04 g, 1 mmole) and DMF (3 ml) and similar process as mentioned herein to afford 10c (0.17 g, 70.83%) as a white solid. m.p. 145.4-146.5. $^1$H-NMR (500 MHz, CDCl$_3$): δ 0.74 (d, J=7 Hz, 6H), 1.20 (t, J=7 Hz, 3H), 2.85 (Sep, J=7 Hz, 1H), 3.12 (t, J=5 Hz, 4H), 3.87 (m, 6H), 6.12 (s, 1H), 6.26 (s, 1H), 6.54 (s, 1H), 6.85 (d, J=8.5 Hz, 2H), 7.01 (m, 2H), 11.75 (s, 1H).

2,4-dihydroxy-5-isopropyl-N-(4-morpholinophenyl)-N-propylbenzamide (10d)

The title compound was prepared using a mixture of 63 (0.36 g, 0.67 mmol), NaH (0.04 g, 1 mmole) and DMF (3 ml) and similar process as mentioned herein to afford 10d (0.18 g, 66.67%) as a white solid. m.p. 191.2-193.1. $^1$H-NMR (500 MHz, MeOD): δ 0.75 (d, J=7 Hz, 6H), 0.9 (t, J=7.5 Hz, 3H), 1.61 (Sex, J=7.5 Hz, 2H), 2.88 (Sep, J=7.5 Hz, 1H), 3.10 (t, J=5 Hz, 4H), 3.78 (m, 6H), 6.19 (s, 1H), 6.54 (s, 1H), 6.88 (d, J=9 Hz, 2H), 7.01 (d, J=9 Hz, 2H).

2,4-dihydroxy-N,5-diisopropyl-N-(4-morpholinophenyl)benzamide (10e)

The title compound was prepared using a mixture of 63 (0.39 g, 0.73 mmol), NaH (0.04 g, 1 mmole) and DMF (3 ml) and similar process as mentioned herein to afford 10e (0.18 g, 62.07%) as a white solid. m.p. 144.1-145.6. $^1$H-NMR (500 MHz, CDCl$_3$): δ 0.75 (d, J=7 Hz, 6H), 1.16 (d, J=7 Hz, 6H), 2.86 (Sep, J=7 Hz, 1H), 3.13 (t, J=5 Hz, 4H), 3.85 (t, J=5 Hz, 4H), 5.05 (Sep, J=7 Hz, 1H), 6.24 (s, 1H), 6.53 (s, 1H), 6.84 (d, J=9 Hz, 2H), 6.98 (d, J=9 Hz, 2H), 11.78 (s, 1H).

4-(2-nitrophenyl)morpholine (65)

The title compound was prepared using a mixture of 1-Bromo-2-nitroaniline (2 g, 9.90 mmol) and morpholine (1.3 g, 14.92 mmol) and similar process as mentioned herein to afford 65 (1.99 g, 96.60%) as a red oily product. $^1$H-NMR (500 MHz, CDCl$_3$): δ 3.03 (t, J=4.5 Hz, 4H), 3.81 (t, J=4.5 Hz, 4H), 7.05 (m, 1H), 7.13 (d, J=8 Hz, 1H), 7.48 (m, 1H), 7.74 (m, 1H).

2,4-bis(benzyloxy)-5-isopropyl-N-(2-morpholinophenyl)benzamide (66)

The title compound was prepared using a mixture of 65 (1.99 g, 9.56 mmol), 10% Palladium on activated carbon (0.4 g, 0.38 mmol) and MeOH (15 ml) and similar process as mentioned herein to afford 66 (2.70 g, 63.08%) as a white solid. $^1$H-NMR (500 MHz, CDCl$_3$): δ 1.26 (d, J=7 Hz, 6H), 2.70 (t, J=4.5 Hz, 4H), 3.33 (qui, J=7 Hz, 1H), 3.50 (t, J=4.5 Hz, 4H), 5.06 (s, 2H), 5.26 (s, 2H), 6.58 (s, 1H), 7.25 (m, 12H), 8.15 (s, 1H), 8.50 (d, J=8 Hz, 1H), 10.36 (s, 1H).

2,4-dihydroxy-5-isopropyl-N-(2-morpholinophenyl)benzamide (11a)

The title compound was prepared using a mixture of 66 (0.31, 0.58 mmol), 10% palladium on activated carbon (0.04 g, 0.04 mmol) and MeOH (8 ml) and similar process as mentioned herein to afford 11a (0.19 g, 90.19%) as a white solid. m.p. 264.8-266.9. $^1$H-NMR (500 MHz, MeOD): δ 1.23 (d, J=7 Hz, 6H), 2.88 (t, J=4.5 Hz, 4H), 3.2 (qui, J=7 Hz, 1H), 3.89 (t, J=4.5 Hz, 4H), 6.44 (s, 1H), 7.10 (m, 2H), 7.23 (d, J=7 Hz, 1H), 7.80 (s, 1H), 8.38 (d, J=7.5 Hz, 1H).

2,4-dihydroxy-5-isopropyl-N-methyl-N-(2-morpholinophenyl)benzamide (11b)

The title compound was prepared using a mixture of 66 (0.33 g, 0.61 mmol), NaH (0.04 g, 1 mmole) and DMF (3 ml) and similar process as mentioned herein to afford 11b (0.17 g, 73.91%) as a white solid. m.p. 166.4-168.3. $^1$H-NMR (500 MHz, MeOD): δ 0.61 (d, J=6.5 Hz, 3H), 0.75 (d, J=6.5 Hz, 3H), 2.26 (s, 2H), 2.76 (m, 2H), 2.84 (qui, J=7 Hz, 1H), 3.38 (s, 3H), 3.61 (d, J=2.5 Hz, 4H), 6.22 (s, 1H), 6.59 (s, 1H), 7.01 (m, 1H), 7.21 (m, 2H), 7.38 (m, 1H).

N-ethyl-2,4-dihydroxy-5-isopropyl-N-(2-morpholinophenyl)benzamide (11c)

The title compound was prepared using a mixture of 66 (0.35 g, 0.65 mmol), NaH (0.04 g, 1 mmole) and DMF (3 ml) and similar process as mentioned herein to afford 11c (0.18 g, 72.0%) as a white solid. m.p. 72.4-73.2. $^1$H-NMR (500 MHz, MeOD): δ 0.70 (m, 6H), 1.29 (t, J=7 Hz, 3H), 2.38 (s, 2H), 2.78 (s, 2H), 2.85 (qui, J=7 Hz, 1H), 3.47 (q, J=6 Hz, 1H), 3.64 (t, J=4 Hz, 4H), 4.29 (d, J=6 Hz, 1H), 6.22 (s, 1H), 6.60 (s, 1H), 7.05 (d, J=8 Hz, 1H), 7.16 (m, 1H), 7.23 (m, 1H), 7.32 (d, J=8 Hz, 1H).

2,4-dihydroxy-5-isopropyl-N-(2-morpholinophenyl)-N-propylbenzamide (11d)

The title compound was prepared using a mixture of 66 (0.38 g, 0.71 mmol), NaH (0.04 g, 1 mmole) and DMF (3 ml) and similar process as mentioned herein to afford 11d (0.19 g, 67.86%) as a white solid. m.p. 70.7-71.6. $^1$H-NMR (500 MHz, MeOD): δ 0.71 (m, 6H), 0.97 (t, J=7.5 Hz, 3H), 1.78 (q, J=7.5 Hz, 2H), 2.33 (s, 2H), 2.80 (s, 2H), 2.85 (qui, J=7 Hz, 1H), 3.30 (m, 1H), 3.66 (m, 4H), 4.25 (m, 1H), 6.20 (s, 1H), 6.62 (s, 1H), 7.08 (m, 1H), 7.24 (m, 2H), 7.38 (m, 1H).

2,4-bis(benzyloxy)-5-isopropyl-N-(2-(morpholine-4-carbonyl)phenyl)benzamide (71)

The title compound was prepared using a mixture of 2-nitrobenzoyl chloride (3 g, 16.17 mmol), TEA (7 ml, 49.81 mmol) and DCM (30 ml) and similar process as mentioned herein to afford 71 (2.94 g, 65.33%) as a white solid. $^1$H-NMR (500 MHz, CDCl$_3$): δ 1.26 (d, J=7 Hz, 6H), 3.35 (Sep, J=7 Hz, 1H), 3.68 (m, 8H), 5.13 (s, 2H), 5.18 (s, 2H), 6.62 (s, 1H), 7.04 (m, 1H), 7.16 (m, 1H), 7.23 (m, 1H), 7.45 (m, 11H), 8.17 (s, 1H), 9.96 (s, 1H).

2,4-bis(benzyloxy)-5-isopropyl-N-(4-(morpholine-4-carbonyl)phenyl)benzamide (72)

The title compound was prepared using a mixture of 4-nitrobenzoyl chloride (3 g, 16.17 mmol), TEA (7 ml, 49.81 mmol) and DCM (30 ml) and similar process as mentioned herein to afford 72 (2.26 g, 50.22%) as a white solid. ¹H-NMR (500 MHz, CDCl₃): δ 1.26 (d, J=7 Hz, 6H), 3.35 (Sep, J=7 Hz, 1H), 3.66 (s, 8H), 5.13 (s, 2H), 5.17 (s, 2H), 6.64 (s, 1H), 7.41 (m, 14H), 8.18 (s, 1H), 10.20 (s, 1H).

2,4-bis(benzyloxy)-5-isopropyl-N-(2-(morpholinomethyl)phenyl)benzamide (73)

The title compound was prepared using a mixture of 1-(chloromethyl)-2-nitrobenzene (3.00 g, 17.48 mmol), TEA (7 ml, 49.81 mmol) and DCM (25 ml) and similar process as mentioned herein to afford 73 (2.27 g, 51.82%) as a white solid. ¹H-NMR (500 MHz, CDCl₃): δ 1.26 (d, J=7 Hz, 6H), 2.23 (s, 4H), 3.30 (s, 2H), 3.34 (qui, J=7 Hz, 1H), 3.42 (s, 4H), 5.08 (s, 2H), 5.11 (s, 2H), 6.57 (s, 1H), 7.29 (m, 13H), 7.86 (s, 1H), 8.36 (d, J=7.5 Hz, 1H), 10.59 (s, 1H).

2,4-bis(benzyloxy)-5-isopropyl-N-(4-(morpholinomethyl)phenyl)benzamide (74)

The title compound was prepared using a mixture of 1-(chloromethyl)-4-nitrobenzene (3.00 g, 17.48 mmol), TEA (7 ml, 49.81 mmol) and DCM (25 ml) and similar process as mentioned herein to afford 74 (2.27 g, 51.82%) as a white solid. ¹H-NMR (500 MHz, CDCl₃): δ 1.26 (d, J=7 Hz, 6H), 2.41 (s, 4H), 3.35 (qui, J=7 Hz, 1H), 3.41 (s, 2H), 3.69 (s, 4H), 5.14 (s, 2H), 5.16 (s, 2H), 6.62 (s, 1H), 7.41 (m, 14H), 8.19 (s, 1H), 9.87 (s, 1H).

2,4-dihydroxy-5-isopropyl-N-(2-(morpholine-4-carbonyl)phenyl)benzamide (12a)

The title compound was prepared using a mixture of 71 (0.35 g, 0.62 mmol), 10% palladium on activated carbon (0.04 g, 0.04 mmol) and MeOH (8 ml) and similar process as mentioned herein to afford 12a (0.22 g, 91.67%) as a white solid. m.p. 191.7-193.0. ¹H-NMR (500 MHz, CDCl₃): δ 1.27 (d, J=6.5 Hz, 6H), 3.15 (Sep, J=7 Hz, 1H), 3.70 (s, 8H), 6.35 (s, 1H), 7.13 (m, 1H), 7.26 (m, 1H), 7.40 (s, 1H), 7.46 (m, 1H), 8.27 (d, J=8 Hz, 1H), 10.16 (s, 1H), 12.18 (s, 1H).

2,4-dihydroxy-5-isopropyl-N-methyl-N-(2-(morpholine-4-carbonyl)phenyl)benzamide (12b)

The title compound was prepared using a mixture of 71 (0.33 g, 0.58 mol), NaH (0.04 g, 1 mmole) and DMF (3 ml) and similar process as mentioned herein to afford 12b (0.17 g, 73.91%) as a white solid. m.p. 247.5-24.9. ¹H-NMR (500 MHz, DMSO): δ 0.57 (m, 6H), 3.30 (m, 12H), 6.26 (s, 1H), 7.10 (m, 5H), 9.80 (m, 1H).

N-ethyl-2,4-dihydroxy-5-isopropyl-N-(2-(morpholine-4-carbonyl)phenyl)benzamide (12c)

The title compound was prepared using a mixture of 71 (0.37 g, 0.66 mmol), NaH (0.04 g, 1 mmole) and DMF (3 ml) and similar process as mentioned herein to afford 12c (0.19 g, 70.37%) as a white solid. m.p. 211.3-213.0. ¹H-NMR (500 MHz, DMSO): δ 0.75 (m, 6H), 1.32 (s, 3H), 1.62 (m, 1H), 3.45 (m, 9H), 4.30 (m, 1H), 6.32 (m, 1H), 6.69 (m, 2H), 7.30 (m, 3H).

2,4-dihydroxy-5-isopropyl-N-(2-(morpholine-4-carbonyl)phenyl)-N-propylbenzamide (12d)

The title compound was prepared using a mixture of 71 (0.38 g, 0.67 mmol), NaH (0.04 g, 1 mmole) and DMF (3 ml) and similar process as mentioned herein to afford 12d (0.2 g, 68.97%) as a white solid. m.p. 190.1-192.3. ¹H-NMR (500 MHz, DMSO): δ 0.88 (m, 9H), 1.75 (m, 4H), 3.41 (m, 8H), 4.32 (m, 1H), 6.30 (s, 1H), 6.69 (s, 1H), 7.30 (m, 3H).

2,4-dihydroxy-5-isopropyl-N-(4-(morpholine-4-carbonyl)phenyl)benzamide (14a)

The title compound was prepared using a mixture of 72 (0.41 g, 0.73 mmol), 10% palladium on activated carbon (0.04 g, 0.04 mmol) and MeOH (8 ml) and similar process as mentioned herein to afford 14a (0.26 g, 92.86%) as a white solid. m.p. 284.5-288.1. ¹H-NMR (500 MHz, MeOD): δ 1.23 (d, =7 Hz, 6H), 3.19 (Sep, J=7 Hz, 1H), 3.70 (m, 8H), 6.35 (s, 1H), 7.43 (t, =7 Hz, 2H), 7.74 (m, 3H).

2,4-dihydroxy-5-isopropyl-N-methyl-N-(4-(morpholine-4-carbonyl)phenyl)benzamide (14b)

The title compound was prepared using a mixture of 72 (0.33 g, 0.58 mmol), NaH (0.04 g, 1 mmole) and DMF (3 ml) and similar process as mentioned herein to afford 14b (0.15 g, 65.22%) as a white solid. m.p. 187.9-189.3. ¹H-NMR (500 MHz, MeOD): δ 0.85 (d, J=7 Hz, 6H), 2.93 (Sep, =7 Hz, 1H), 3.42 (s, 3H), 3.68 (m, 8H), 6.18 (s, 1H), 6.69 (s, 1H), 7.26 (d, =8 Hz, 2H), 7.39 (d, J=8 Hz, 2H).

N-ethyl-2,4-dihydroxy-5-isopropyl-N-(4-(morpholine-4-carbonyl)phenyl)benzamide (14c)

The title compound was prepared using a mixture of 72 (0.35 g, 0.62 mmol), NaH (0.04 g, 1 mmole) and DMF (3 ml) and similar process as mentioned herein to afford 14c (0.18 g, 69.23%) as a white solid. m.p. 216.2-217.8. ¹H-NMR (500 MHz, MeOD): δ 0.80 (d, J=7 Hz, 6H), 1.18 (t, J=7 Hz, 3H), 2.90 (Sep, J=7 Hz, 1H), 3.48 (m, 8H), 3.93 (q, J=7 Hz, 2H), 6.19 (s, 1H), 6.63 (s, 1H), 7.22 (d, =8.5 Hz, 2H), 7.39 (m, 2H).

2,4-dihydroxy-5-isopropyl-N-(4-(morpholine-4-carbonyl)phenyl)-N-propylbenzamide (14d)

The title compound was prepared using a mixture of 72 (0.37 g, 0.66 mmol), NaH (0.04 g, 1 mmole) and DMF (3 ml) and similar process as mentioned herein to afford 14d (0.19 g, 67.86%) as a white solid. m.p. 206.3-207.7. ¹H-NMR (500 MHz, MeOD): δ 0.78 (d, J=6.5 Hz, 6H), 0.91 (t, J=7.5 Hz, 3H), 1.62 (Sex, J=7.5 Hz, 2H), 2.90 (Sep, J=7 Hz, 1H), 3.55 (m, 8H), 3.82 (t, J=7.5 Hz, 2H), 6.20 (s, 1H), 6.60 (s, 1H), 7.21 (d, J=8.5 Hz, 2H), 7.37 (d, J=8.5 Hz, 2H).

2,4-dihydroxy-N,5-diisopropyl-N-(4-(morpholine-4-carbonyl)phenyl)benzamide (14e)

The title compound was prepared using a mixture of 72 (0.39 g, 0.69 mmol), NaH (0.04 g, 1 mmole) and DMF (3 ml) and similar process as mentioned herein to afford 14e (0.19 g, 65.51%) as a white solid. m.p. 176.8-177.8. ¹H-NMR (500 MHz, MeOD): δ 0.92 (d, J=7 Hz, 6H), 1.21 (d, J=7 Hz, 6H), 2.94 (Sep, J=7 Hz, 1H), 3.65 (m, 8H), 4.93 (Sep, J=7 Hz, 1H), 6.11 (s, 1H), 6.67 (s, 1H), 7.25 (m, 2H), 7.36 (m, 2H).

2,4-dihydroxy-5-isopropyl-N-(2-(morpholinomethyl)phenyl)benzamide (15a)

The title compound was prepared using a mixture of 73 (0.31 g, 0.56 mmol), 10% palladium on activated carbon (0.04 g, 0.04 mmol) and MeOH (8 ml) and similar process as mentioned herein to afford 15a (0.11 g, 52.38%) as a white solid. m.p. 191.0-192.3. $^1$H-NMR (500 MHz, MeOD): δ 1.30 (d, J=7 Hz, 6H), 2.52 (s, 4H), 3.10 (Sex, J=7 Hz, 1H), 3.65 (s, 2H), 3.79 (t, J=4.5 Hz, 4H), 6.36 (s, 1H), 7.08 (m, 1H), 7.17 (d, J=6.5 Hz, 1H), 7.31 (s, 1H), 7.36 (m, 1H), 8.10 (d, J=8 Hz, 1H).

N-ethyl-2,4-dihydroxy-5-isopropyl-N-(2-(morpholinomethyl)phenyl)benzamide (15b)

The title compound was prepared using a mixture of 73 (0.35, 0.64 mmol), NaH (0.04 g, 1 mmole) and DMF (3 ml) and similar process as mentioned herein to afford 15b (0.15 g, 57.69%) as a colorless oil. $^1$H-NMR (500 MHz, MeOD): δ 0.64 (s, 3H), 0.76 (s, 3H), 1.25 (s, 3H), 2.26 (d, J=5.5 Hz, 4H), 2.85 (s, 1H), 3.05 (m, 1H), 3.61 (m, 6H), 4.14 (s, 1H), 6.20 (s, 1H), 6.50 (s, 1H), 7.31 (m, 1H), 7.39 (d, J=4 Hz, 2H), 7.51 (d, J=7 Hz, 1H).

2,4-dihydroxy-5-isopropyl-N-(2-(morpholinomethyl)phenyl)-N-propylbenzamide (15c)

The title compound was prepared using a mixture of 73 (0.36 g, 0.65 mmol), NaH (0.04 g, 1 mmole) and DMF (3 ml) and similar process as mentioned herein to afford 15c (0.13 g, 48.15%) as a yellow solid. m.p. 137.2-139.4. $^1$H-NMR (500 MHz, MeOD): δ 0.64 (d, J=4 Hz, 3H), 0.77 (d, J=4 Hz, 3H), 0.95 (s, 3H), 1.72 (s, 2H), 2.25 (s, 4H), 2.84 (s, 1H), 3.04 (m, 1H), 3.47 (m, 6H), 4.09 (q, J=7 Hz, 2H), 6.19 (s, 1H), 6.51 (s, 1H), 7.31 (m, 1H), 7.38 (m, 2H), 7.49 (d, J=7 Hz, 1H).

2,4-dihydroxy-5-isopropyl-N-(4-(morpholinomethyl)phenyl)benzamide (17a)

The title compound was prepared using a mixture of 74 (0.31 g, 0.56 mmol), 10% palladium on activated carbon (0.04 g, 0.04 mmol) and MeOH (6 ml) and similar process as mentioned herein to afford 17a (0.1 g, 47.62%) as a pink solid. m.p. 111.2-113.1. $^1$H-NMR (500 MHz, MeOD): δ 1.23 (d, J=7 Hz, 6H), 2.45 (m, 4H), 3.19 (Sex, J=7 Hz, 1H), 3.47 (s, 2H), 3.66 (t, J=4.5 Hz, 4H), 6.33 (s, 1H), 7.29 (d, J=8.5 Hz, 2H), 7.57 (d, J=8.5 Hz, 2H), 7.74 (s, 1H).

N-ethyl-2,4-dihydroxy-5-isopropyl-N-(4-(morpholinomethyl)phenyl)benzamide (17b)

The title compound was prepared using a mixture of 74 (0.38 g, 0.69 mmol), NaH (0.04 g, 1 mmole) and DMF (3 ml) and similar process as mentioned herein to afford 17b (0.14 g, 51.85%) as a white solid. m.p. 153.0-154.7. $^1$H-NMR (500 MHz, MeOD): δ 0.77 (d, J=7 Hz, 6H), 1.17 (t, J=7 Hz, 3H), 2.42 (t, J=4.5 Hz, 4H), 2.87 (sep, J=7 Hz, 1H), 3.45 (s, 2H), 3.65 (t, J=4.5 Hz, 4H), 3.89 (q, J=7 Hz, 2H), 6.18 (s, 1H), 6.60 (s, 1H), 7.11 (d, J=8.5 Hz, 2H), 7.30 (d, J=8.5 Hz, 2H).

2,4-dihydroxy-5-isopropyl-N-(4-(morpholinomethyl)phenyl)-N-propylbenzamide (17c)

The title compound was prepared using a mixture of 74 (0.34 g, 0.62 mmol), NaH (0.04 g, 1 mmole) and DMF (3 ml) and similar process as mentioned herein to afford 17c (0.14 g, 53.84%) as a white solid. m.p. 144.3-145.0. $^1$H-NMR (500 MHz, MeOD): δ 0.78 (d, J=6.5 Hz, 6H), 0.91 (t, J=7.5 Hz, 3H), 1.61 (Sex, J=7.5 Hz, 2H), 2.42 (m, 4H), 2.87 (Sep, J=7 Hz, 1H), 3.45 (s, 2H), 3.65 (t, J=4.5 Hz, 4H), 3.81 (m, 2H), 6.17 (s, 1H), 6.60 (s, 1H), 7.11 (d, J=8.5 Hz, 2H), 7.29 (d, J=8.5 Hz, 2H).

Morpholino(3-nitrophenyl)methanone (76)

The title compound was prepared using a mixture of 3-nitrobenzaldehyde (3.00 g, 19.85 mmol), sulfamic acid (10.15 g, 104.53 mmol), DMSO (2 ml), THF (20 ml) and water (20 ml) and similar process as mentioned herein to afford 76 (2.89 g, 61.62%) as a yellow solid. $^1$H-NMR (500 MHz, CDCl$_3$): δ 3.61 (m, 8H), 7.59 (t, J=8 Hz, 1H), 7.70 (d, J=8 Hz, 1H), 8.22 (m, 2H).

4-(3-nitrobenzyl)morpholine (77)

The title compound was prepared using a mixture of 3-nitrobenzaldehyde (3.00 g, 19.85 mmol), morpholine (2.5 ml, 28.90 mmol), MeOH (15 ml) and acetic acid (cat.) and similar process as mentioned herein to afford 77 (1.83 g, 41.50%) as a oily product. $^1$H-NMR (500 MHz, CDCl$_3$): δ 2.45 (t, J=4.5 Hz, 4H), 3.58 (s, 2H), 3.71 (t, J=4.5 Hz, 4H), 7.48 (t J=7.5 Hz, 1H), 7.67 (d, J=7.5 Hz, 1H), 8.11 (m, 1H), 8.21 (s, 1H).

2,4-bis(benzyloxy)-5-isopropyl-N-(3-(morpholine-4-carbonyl)phenyl)benzamide (78)

The title compound was prepared using a mixture of 76 (2.5 g, 10.58 mmol), 10% palladium on activated carbon (0.25 g, 0.23 mmol) and MeOH (15 ml) and similar process as mentioned herein to afford 78 (3.52 g, 57.70%) as a white solid. $^1$H-NMR (500 MHz, CDCl$_3$): δ 1.26 (d, J=7 Hz, 6H), 3.35 (Sep, J=7 Hz, 1H), 3.68 (m, 8H), 5.13 (s, 2H), 5.18 (s, 2H), 6.62 (s, 1H), 7.04 (m, 1H), 7.16 (m, 1H), 7.23 (m, 1H), 7.45 (m, 11H), 8.17 (s, 1H), 9.96 (s, 1H).

2,4-bis(benzyloxy)-5-isopropyl-N-(3-(morpholinomethyl)phenyl)benzamide (79)

The title compound was prepared using a mixture of 77 (1.80 g, 8.10 mmol), Fe powder (2.26 g, 40.47 mmol), NH$_4$Cl (1.70 g, 31.78 mmol), IPA (64 ml) and H$_2$O (16 ml) and similar process as mentioned herein to afford 79 (1.5 g, 51.36%) as a white solid. $^1$H-NMR (500 MHz, CDCl$_3$): δ 1.27 (d, J=7 Hz, 6H), 2.41 (s, 4H), 3.35 (qui, J=7 Hz, 3H), 3.69 (t, J=4.5 Hz, 4H), 5.15 (s, 2H), 5.16 (s, 2H), 6.63 (s, 1H), 7.40 (m, 14H), 8.21 (s, 1H), 9.89 (s, 1H).

2,4-dihydroxy-5-isopropyl-N-(3-(morpholine-4-carbonyl)phenyl)benzamide (13a)

The title compound was prepared using a mixture of 78 (0.40 g, 0.71 mmol), 10% palladium on activated carbon (0.04 g, 0.04 mmol) and MeOH (8 ml) and similar process as mentioned herein to afford 13a (0.25 g, 92.59%) as a white solid. m.p. 246.0-247.4. $^1$H-NMR (500 MHz, MeOD): δ 1.24 (d, J=7 Hz, 6H), 3.19 (Sep, J=7 Hz, 1H), 3.65 (m, 8H), 6.34 (s, 1H), 7.17 (d, J=7.5 Hz, 1H), 7.43 (t, J=8 Hz, 1H), 7.68 (m, 1H) 7.55 (s, 1H), 7.79 (d, J=1.5 Hz, 1H).

2,4-dihydroxy-5-isopropyl-N-methyl-N-(3-(morpholine-4-carbonyl)phenyl)benzamide (13b)

The title compound was prepared using a mixture of 78 (0.35 g, 0.62 mmol), NaH (0.04 g, 1 mmole) and DMF (3 ml) and similar process as mentioned herein to afford 13b (0.17 g, 68.0%) as a white solid. m.p. 216.3-217.6. $^1$H-NMR (500 MHz, MeOD): δ 0.84 (d, J=7 Hz, 6H), 2.96 (Sex, J=7 Hz, 3H), 3.35 (s, 2H), 3.44 (s, 3H), 3.64 (s, 4H), 6.19 (s, 1H), 6.65 (s, 1H), 6.96 (s, 1H), 7.28 (m, 1H), 7.52 (m, 2H).

2,4-dihydroxy-5-isopropyl-N-(3-(morpholine-4-carbonyl)phenyl)-N-propylbenzamide (13c)

The title compound was prepared using a mixture of 78 (0.33 g, 0.58 mmol), NaH (0.04 g, 1 mmole) and DMF (3 ml) and similar process as mentioned herein to afford 13c (0.17 g, 70.83%) as a white solid. $^1$H-NMR (500 MHz, MeOD): δ 0.83 (d, J=7 Hz, 6H), 1.19 (t, J=7 Hz, 3H), 2.89 (Sex, J=7 Hz, 3H), 3.35 (s, 2H), 3.64 (s, 4H), 3.96 (q, J=7 Hz, 2H), 6.19 (s, 1H), 6.64 (s, 1H), 6.92 (s, 1H), 7.30 (m, 1H), 7.53 (m, 2H).

2,4-dihydroxy-5-isopropyl-N-(3-(morpholine-4-carbonyl)phenyl)-N-propylbenzamide (13d)

The title compound was prepared using a mixture of 78 (0.36 g, 0.63 mmol), NaH (0.04 g, 1 mmole) and DMF (3 ml) and similar process as mentioned herein to afford 13d (0.19 g, 70.37%) as a white solid. m.p. 219.1-220.8. $^1$H-NMR (500 MHz, MeOD): δ 0.78 (d, J=7 Hz, 6H), 0.92 (t, J=7.5 Hz, 3H), 1.62 (Sep, J=7.5 Hz, 2H), 2.87 (m, 3H), 3.33 (s, 2H), 3.64 (s, 4H), 3.85 (t, J=7.5 Hz, 2H), 6.21 (s, 1H), 6.58 (s, 1H), 6.87 (d, J=2 Hz, 1H), 7.29 (m, 1H), 7.51 (m, 2H).

2,4-dihydroxy-N,5-diisopropyl-N-(3-(morpholine-4-carbonyl)phenyl)benzamide (13e)

The title compound was prepared using a mixture of 78 (0.36 g, 0.63 mmol), NaH (0.04 g, 1 mmole) and DMF (3 ml) and similar process as mentioned herein to afford 13e (0.18 g, 66.67%) as a white solid. m.p. 224.8-227.0. $^1$H-NMR (500 MHz, MeOD): δ 0.80 (d, =5.5 Hz, 6H), 1.22 (m, 6H), 2.76 (s, 2H), 2.87 (Sep, J=7 Hz, 1H), 3.32 (s, 2H), 3.65 (s, 4H), 4.96 (Sep, J=7 Hz, 1H), 6.17 (s, 1H), 6.53 (s, 1H), 6.82 (s, 1H), 7.32 (m, 1H), 7.48 (m, 2H).

2,4-dihydroxy-5-isopropyl-N-(3-(morpholinomethyl)phenyl)benzamide (16a)

The title compound was prepared using a mixture of 79 (0.5 g, 0.91 mmol), 10% palladium on activated carbon (0.04 g, 0.04 mmol) and MeOH (8 ml) and similar process as mentioned herein to afford 16a (0.19 g, 55.88%) as a white solid. m.p. 90.0-90.7. $^1$H-NMR (500 MHz, CDCl$_3$): δ 1.24 (d, J=7 Hz, 6H), 2.48 (s, 4H), 3.20 (qui, J=7 Hz, 1H), 3.53 (s, 2H), 3.69 (t, J=4.5 Hz, 4H), 6.34 (s, 1H), 7.11 (d, J=7.5 Hz, 1H), 7.31 (t, J=7.5 Hz, 1H), 7.55 (m, 1H), 7.60 (s 1H), 7.45 (s, 1H).

N-ethyl-2,4-dihydroxy-5-isopropyl-N-(3-(morpholinomethyl)phenyl)benzamide (16b)

The title compound was prepared using a mixture of 79 (0.40 g, 0.73 mmol), NaH (0.04 g, 1 mmole) and DMF (3 ml) and similar process as mentioned herein to afford 16b (0.18 g, 62.07%) as a white solid. m.p. 201.5-203.2. $^1$H-NMR (500 MHz, MeOD): δ 0.79 (d, J=7 Hz, 6H), 1.20 (t, J=7 Hz, 3H), 2.19 (t, J=4.5 Hz, 4H), 2.87 (Sep, J=7 Hz, 1H), 3.41 (s, 2H), 3.57 (t, J=4.5 Hz, 4H), 3.95 (q, J=7 Hz, 2H), 6.20 (s, 1H), 6.59 (s, 1H), 6.94 (s, 1H), 7.18 (d, J=7.5 Hz, 1H), 7.27 (d, J=9 Hz, 1H), 7.38 (t, J=7.5 Hz, 1H).

2,4-dihydroxy-5-isopropyl-N-(3-(morpholinomethyl)phenyl)-N-propylbenzamide (16c)

The title compound was prepared using a mixture of 79 (0.35 g, 0.64 mmol), NaH (0.04 g, 1 mmole) and DMF (3 ml) and similar process as mentioned herein to afford 16c (0.15 g, 57.69%) as a white solid. m.p. 224.8-227.0. $^1$H-NMR (500 MHz, CDCl$_3$): δ 0.62 (d, J=7 Hz, 6H), 0.86 (t, J=7.5 Hz, 3H), 1.58 (Sex, J=7.5 Hz, 2H), 2.13 (d, J=4.5 Hz, 4H), 2.76 (Sep, J=7 Hz, 1H), 3.32 (s, 2H), 3.51 (t, J=4.5 Hz, 4H), 3.75 (t, J=7.5 Hz, 2H), 6.16 (s, 1H), 6.41 (s, 1H), 6.86 (s, 1H), 7.06 (d, J=7.5 Hz, 1H), 7.27 (t, J=8 Hz, 1H).

2,4-bis(benzyloxy)-5-isopropyl-N-(pyridin-3-yl)benzamide (80)

The title compound was prepared using a mixture of 47 (2 g, 5.31 mmol), EDC.HCl (1.5 g, 7.85 mmol), HOBt (0.9 g, 6.67 mmol), NMM (1.4 ml, 12.75 mmol) and DMF (8 ml) and similar process as mentioned herein to afford 80 (1.76 g, 73.33%) as a white solid. $^1$H-NMR (500 MHz, CDCl$_3$): δ 1.27 (d, J=7 Hz, 6H), 3.36 (Sep, J=7 Hz, 1H), 5.15 (s, 2H), 5.18 (s, 2H), 6.64 (s, 1H), 7.18 (m, 1H), 7.45 (m, 10H), 7.95 (m, 1H), 8.16 (m, 1H), 8.20 (s, 1H), 8.28 (m, 1H), 9.93 (s, 1H).

2,4-bis(benzyloxy)-5-isopropyl-N-(pyridin-4-yl)benzamide (81)

The title compound was prepared using a mixture of 47 (2 g, 5.31 mmol), EDC.HCl (1.5 g, 7.85 mmol), HOBt (0.9 g, 6.67 mmol), NMM (1.4 ml, 12.75 mmol) and DMF (8 ml) and similar process as mentioned herein to afford 81 (1.7 g, 70.83%) as a white solid. $^1$H-NMR (500 MHz, CDCl$_3$): δ 1.27 (d, J=7 Hz, 6H), 3.35 (qui, J=7 Hz, 1H), 5.14 (s, 2H), 5.18 (s, 2H), 6.64 (s, 1H), 7.07 (m, 2H), 7.41 (m, 10H), 8.16 (s, 1H), 8.34 (m, 2H), 10.01 (s, 1H).

2,4-dihydroxy-5-isopropyl-N-(pyridin-3-yl)benzamide (18a)

The title compound was prepared using a mixture of 80 (0.42 g, 0.93 mmol), 10% palladium on activated carbon (0.04 g, 0.04 mmol) and MeOH (8 ml) and similar process as mentioned herein to afford 18a (0.22 g, 88.0%) as a white solid. m.p. 269.1-270.3. $^1$H-NMR (500 MHz, MeOD): δ 1.24 (d, J=7 Hz, 6H), 3.20 (Sep, J=7 Hz, 1H), 6.35 (s, 1H), 7.43 (m, 1H), 7.75 (s, 1H), 8.19 (m, 1H), 8.27 (m, 1H), 8.82 (d, J=2.5 Hz, 1H).

N-ethyl-2,4-dihydroxy-5-isopropyl-N-(pyridin-3-yl)benzamide (18b)

The title compound was prepared using a mixture of 80 (0.35 g, 0.77 mmol), NaH (0.04 g, 1 mmole) and DMF (4 ml) and similar process as mentioned herein to afford 18b (0.16 g, 69.57%) as a yellow solid. m.p. 179.6-181.5. $^1$H-NMR (500 MHz, MeOD): δ 0.90 (d, J=7 Hz, 6H), 1.20 (t, J=7 Hz 3H), 2.96 (Sep, J=7 Hz, 1H), 3.95 (q, J=7 Hz, 2H), 6.15 (s, 1H), 6.66 (s, 1H), 7.39 (m, 1H), 7.69 (m, 1H), 8.28 (d, J=2 Hz, 1H), 8.34 (m, 1H).

2,4-dihydroxy-5-isopropyl-N-propyl-N-(pyridin-3-yl)benzamide (18c)

The title compound was prepared using a mixture of 80 (0.40 g, 0.88 mmol), NaH (0.04 g, 1 mmole) and DMF (4 ml) and similar process as mentioned herein to afford 18c (0.19 g, 67.85%) as a white solid. m.p. 196.3-198.2. $^1$H-NMR (500 MHz, MeOD): δ 0.92 (m, 9H), 1.63 (6, J=7.5 Hz, 2H), 2.97 (Sep, J=7 Hz, 1H), 3.87 (t, J=7.5 Hz, 2H), 6.14 (s, 1H), 6.66 (s, 1H), 7.38 (m, 1H), 7.70 (m, 1H), 8.29 (m, 2H).

2,4-dihydroxy-N,5-diisopropyl-N-(pyridin-3-yl)benzamide (18d)

The title compound was prepared using a mixture of 80 (0.34 g, 0.75 mmol), NaH (0.04 g, 1 mmole) and DMF (3 ml) and similar process as mentioned herein to afford 18d (0.15 g, 60.25%) as a yellow solid. m.p. 172.4-174.3. $^1$H-NMR (500 MHz, MeOD): δ 0.96 (d, J=6.5 Hz, 6H), 1.19 (d, J=7 Hz, 6H), 2.98 (Sep, J=7 Hz, 1H), 4.96 (Sep, J=7 Hz, 1H), 6.11 (s, 1H), 6.66 (s, 1H), 7.37 (m, 1H), 7.68 (m, 1H), 8.29 (d, J=2.5 Hz, 1H), 8.37 (m, 1H).

2,4-dihydroxy-5-isopropyl-N-(pyridin-4-yl)benzamide (19a)

The title compound was prepared using a mixture of 81 (0.38 g, 0.84 mmol), 10% palladium on activated carbon (0.04 g, 0.04 mmol) and MeOH (8 ml) and similar process as mentioned herein to afford 19a (0.20 g, 86.95%) as a yellow solid. m.p. 235.9-238.3. $^1$H-NMR (500 MHz, MeOD): δ 1.23 (d, J=7 Hz, 6H), 3.19 (Sep, J=7 Hz, 1H), 6.36 (s, 1H), 7.77 (m, 3H), 8.40 (d, J=6.5 Hz, 2H).

N-ethyl-2,4-dihydroxy-5-isopropyl-N-(pyridin-4-yl)benzamide (19b)

The title compound was prepared using a mixture of 81 (0.33 g, 0.73 mmol), NaH (0.04 g, 1 mmole) and DMF (4 ml) and similar process as mentioned herein to afford 19b (0.14 g, 63.64%) as a white solid. m.p. 185.2-186.1. $^1$H-NMR (500 MHz, MeOD): δ 0.86 (d, J=7 Hz, 6H), 1.21 (t, J=7 Hz, 3H), 2.97 (Sep, J=7 Hz, 1H) 4.01 (q, J=7 Hz, 2H), 6.20 (s, 1H), 6.68 (s, 1H), 7.17 (m, 2H), 8.40 (m, 2H).

2,4-dihydroxy-5-isopropyl-N-propyl-N-(pyridin-4-yl)benzamide (19c)

The title compound was prepared using a mixture of 81 (0.32 g, 0.71 mmol), NaH (0.04 g, 1 mmole) and DMF (4 ml) and similar process as mentioned herein to afford 19c (0.14 g, 63.64%) as a white solid. m.p. 196.3-198.2. $^1$H-NMR (500 MHz, MeOD): δ 0.86 (d, J=7 Hz, 6H), 0.94 (t, J=7.5 Hz, 3H), 1.65 (Sex, J=7.5 Hz, 2H), 2.97 (Sep, J=7 Hz, 1H), 3.92 (t, J=7.5 Hz, 2H), 6.20 (s, 1H), 6.68 (s, 1H), 7.17 (m, 2H), 8.39 (m, 2H).

2,4-dihydroxy-N,5-diisopropyl-N-(pyridin-4-yl)benzamide (19d)

The title compound was prepared using a mixture of 81 (0.34 g, 0.75 mmol), NaH (0.04 g, 1 mmole) and DMF (3 ml) and similar process as mentioned herein to afford 19d (0.15 g, 60.25%) as a white solid. m.p. 165.4-166.6. $^1$H-NMR (500 MHz, MeOD): δ 0.89 (d, J=7 Hz, 6H), 1.27 (d, J=6.5 Hz, 6H), 2.96 (Sep, J=7 Hz, 1H), 4.89 (Sep, J=7 Hz, 1H), 6.15 (s, 1H), 6.63 (s, 1H), 7.21 (d, J=6 Hz, 2H), 8.44 (m, 2H).

tert-butyl 5-(2,4-bis(benzyloxy)-5-isopropylbenzamido)-1H-indole-1-carboxylate (84)

The title compound was prepared using a mixture of 5-nitroindole (2 g, 12.33 mmol) was dissolved in DCM (15 ml) and similar process as mentioned herein to afford 84 (2.46 g, 78.59%) as a white solid. $^1$H-NMR (500 MHz, CDCl$_3$): δ 1.28 (d, J=7 Hz, 6H), 1.16 (s, 9H), 3.36 (qui, J=7 Hz, 1H), 5.15 (s, 4H), 6.45 (s, 1H), 6.46 (s, 1H), 6.80 (s, 1H), 7.44 (m, 11H), 7.91 (s, 2H), 8.24 (s, 1H), 9.95 (s, 1H).

tert-butyl 6-(2,4-bis(benzyloxy)-5-isopropylbenzamido)-1H-indole-1-carboxylate (85)

The title compound was prepared using a mixture of 6-nitroindole (0.2 g, 1.23 mmol) dissolved in DCM (10 ml), DMAP (0.23 g, 1.85 mmol) and Boc anhydride (0.4 g, 1.85 mmol) and similar process as mentioned herein to afford 85 (0.26 g, 82.45%) as a white solid. $^1$H-NMR (300 MHz, CDCl$_3$): δ 1.28 (d, J=6.9 Hz, 6H), 1.68 (s, 9H), 3.35 (m, 1H), 5.15 (s, 2H), 5.18 (s, 2H), 6.47 (d, J=3.6 Hz, 1H), 6.62 (s, 1H), 6.86 (d, J=8.1 Hz, 1H), 7.33 (d, J=8.1 Hz, 1H), 7.36-7.52 (m, 11H), 8.23 (s, 1H), 8.66 (s, 1H), 9.92 (s, 1H).

2,4-dihydroxy-N-(1H-indol-5-yl)-5-isopropylbenzamide (20a)

The title compound was prepared using a mixture of 84 (0.5 g, 0.85 mmol) dissolved in DCM (5 ml) and TFA (1 ml) and similar process as mentioned herein to afford 20a (0.19 g, 73.07%) as a green solid. m.p. 221.1-223.7. $^1$H-NMR (500 MHz, MeOD): δ 1.22 (d, J=6.5 Hz, 6H), 3.19 (Sep, J=7 Hz, 1H), 6.35 (s, 1H), 6.41 (d, J=7 Hz, 1H), 7.15 (d, J=2 Hz, 1H), 7.20 (m, 1H), 7.32 (d, J=8.5 Hz, 1H), 7.24 (m, 2H).

2,4-dihydroxy-N-(1H-indol-5-yl)-5-isopropyl-N-methylbenzamide (20b)

The title compound was prepared using a mixture of 84 (0.8 g, 1.35 mmol), NaH (0.07 g, 1.75 mmole) and DMF (5 ml) and similar process as mentioned herein to afford 20b (0.25 g, 56.82%) as a white solid. m.p. 217.7-219.5. $^1$H-NMR (500 MHz, MeOD): δ 0.49 (d, J=7 Hz, 6H), 2.74 (qui, J=7 Hz, 1H), 3.46 (s, 3H), 6.16 (s, 1H), 6.41 (d, J=3 Hz, 1H), 6.48 (s, 1H), 6.94 (m, 1H), 7.26 (d, J=3 Hz, 1H), 7.33 (s, 1H), 7.37 (d, J=8.5 Hz, 1H).

N-ethyl-2,4-dihydroxy-N-(1H-indol-5-yl)-5-isopropylbenzamide (20c)

The title compound was prepared using a mixture of 84 (0.75 g, 1.27 mmol), NaH (0.07 g, 1.75 mmole) and DMF (6 ml) and similar process as mentioned herein to afford 20c (0.22 g, 51.16%) as a white solid. m.p. 234.4-236.7. $^1$H-NMR (500 MHz, MeOD): δ 0.46 (d, J=6.5 Hz, 6H), 1.21 (t, J=7 Hz, 3H), 2.72 (Sex, J=7 Hz, 1H), 3.94 (q, J=7 Hz, 2H), 6.17 (s. 1H), 6.39 (d, J=3 Hz, 1H), 6.45 (s, 1H), 6.91 (m, 1H), 7.24 (d, J=3 Hz, 1H), 7.30 (d, J=2 Hz, 1H), 7.37 (d, J=8.5 Hz, 1H).

2,4-dihydroxy-N-(1H-indol-5-yl)-5-isopropyl-N-propylbenzamide (20d)

The title compound was prepared using a mixture of 84 (0.78 g, 1.32 mmol), NaH (0.07 g, 1.75 mmole) and DMF (6 ml) and similar process as mentioned herein to afford 20d (0.24 g, 51.06%) as a white solid. m.p. 206.0-207.8. $^1$H-NMR (500 MHz, MeOD): δ 0.48 (d, J=6.5 Hz, 6H), 0.93 (t, J=7.5 Hz, 3H), 1.66 (Sex, J=7.5 Hz, 2H), 2.73 (Sex, J=6.5 HZ, 1H), 3.86 (t, J=7.5 Hz, 2H), 6.16 (s, 1H), 6.40 (d, J=3

Hz, 1H), 6.46 (s, 1H), 6.91 (s, 1H), 7.25 (d, J=3.5 Hz, 1H), 7.31 (d, J=1.5 Hz, 1H), 7.34 (d, J=8.5 Hz, 1H).

2,4-dihydroxy-N-(1H-indol-5-yl)-N,5-diisopropylbenzamide (20e)

The title compound was prepared using a mixture of 84 (0.81 g, 1.37 mmol), NaH (0.07 g, 1.75 mmole) and DMF (7 ml) and similar process as mentioned herein to afford 20e (0.23 g, 47.91%) as a white solid. m.p. 226.1-227.9. $^1$H-NMR (500 MHz, MeOD): δ 0.56 (d, J=5.5 Hz, 6H), 1.19 (d, J=7 Hz, 6H), 2.76 (qui, J=7 Hz, 1H), 5.04 (t, J=5.5 Hz, 1H), 6.13 (s, 1H), 6.42 (d, J=3 Hz, 1H), 6.49 (s, 1H), 6.86 (m, 1H), 7.24 (d, J=3 Hz, 1H), 7.31 (d, J=1.5 Hz, 1H), 7.33 (d, J=9 Hz, 1H).

2,4-dihydroxy-N-(1H-indol-6-yl)-5-isopropylbenzamide (21a)

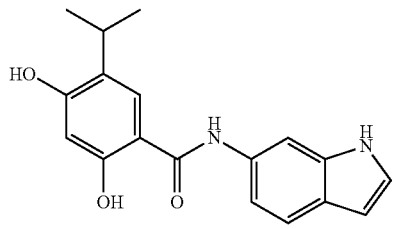 [SMILES: CC(C)c1cc(C(=O)Nc2ccc3cc[nH]c3c2)c(O)cc1O]

2,4-dihydroxy-N-(indolin-5-yl)-5-isopropylbenzamide (23a)

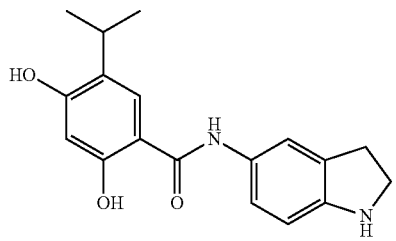 [SMILES: CC(C)c1cc(C(=O)Nc2ccc3c(c2)CCN3)c(O)cc1O]

The title compound was prepared using a mixture of 20a (0.25 g, 0.81 mmol) dissolved in acetic acid (5 ml) and NaBH$_3$CN (0.2 g, 3.18 mmol) and similar process as mentioned herein to afford 23a (0.19 g, 76.0%) as a green solid. m.p. 104.9-107.5. $^1$H-NMR (500 MHz, MeOD): δ 1.23 (d, J=7 Hz, 6H), 3.00 (t, J=8.5 Hz, 2H), 3.19 (hept, J=7 Hz, 1H), 3.48 (t, J=8.5 Hz, 2H), 6.31 (s, 1H), 6.66 (d, =8.5 Hz, 1H), 7.12 (m, 1H), 7.32 (s, 1H), 7.70 (s, 1H).

2,4-dihydroxy-N-(indolin-5-yl)-5-isopropyl-N-methylbenzamide (23b)

The title compound was prepared using a mixture of 20b (0.27 g, 0.83 mmol) dissolved in acetic acid (6 ml) and NaBH$_3$CN (0.2 g, 3.18 mmol) and similar process as mentioned hereinto afford 23b (0.2 g, 74.07%) as a pink solid. m.p. 176.7-178.3. $^1$H-NMR (500 MHz, MeOD): δ 0.82 (d, =7 Hz, 6H), 2.92 (m, 3H), 3.34 (s, 3H), 3.46 (t, J=8.5 Hz, 2H), 6.17 (s, 1H), 6.56 (d, J=8 Hz, 1H), 6.68 (s, 1H), 6.76 (m, 1H), 6.90 (s, 1H).

N-ethyl-2,4-dihydroxy-N-(indolin-5-yl)-5-isopropylbenzamide (23c)

The title compound was prepared using a mixture of 20c (0.2 g, 0.59 mmol) dissolved in acetic acid (5 ml) and NaBH$_3$CN (0.2 g, 3.18 mmol) and similar process as mentioned hereinto afford 23c (0.14 g, 70.0%) as a white solid. 213.3-215.6. $^1$H-NMR (500 MHz, MeOD): δ 0.82 (d, J=6.5 Hz, 6H), 1.17 (t, J=7 Hz, 3H), 2.91 (m, 3H), 3.47 (t, J=8 Hz, 2H), 3.83 (q, J=7 Hz, 2H), 6.17 (s, 1H), 6.56 (d, J=8 Hz, 1H), 6.67 (s, 1H), 6.72 (m, 1H), 6.87 (d, J=1.5 Hz, 1H).

2,4-dihydroxy-N-(indolin-5-yl)-5-isopropyl-N-propylbenzamide (23d)

The title compound was prepared using a mixture of 20d (0.24 g, 0.68 mmol) dissolved in acetic acid (5 ml) and NaBH$_3$CN (0.2 g, 3.18 mmol) and similar process as mentioned herein to afford 23d (0.17 g, 70.83%) as a brown solid. m.p. 150.1-152.2. $^1$H-NMR (500 MHz, MeOD): δ 0.82 (d, J=7 Hz, 6H), 0.92 (t, J=7.5 Hz, 3H), 1.62 (Sex, J=7.5 Hz, 2H), 2.91 (m, 3H), 3.46 (t, J=8.5 Hz, 2H), 3.74 (m, 2H), 6.16 (s, 1H), 6.56 (t, J=8.5 Hz, 1H), 6.66 (s, 1H), 6.72 (m, 1H), 6.88 (d, J=1.5 Hz, 1H).

2,4-dihydroxy-N-(indolin-5-yl)-N,5-diisopropylbenzamide (23e)

The title compound was prepared using a mixture of 20e (0.2 g, 0.57 mmol) dissolved in acetic acid (4 ml) and NaBH$_3$CN (0.2 g, 3.18 mmol) and similar process as mentioned herein to afford 23e (0.14 g, 70.0%) as a pink solid. m.p. 226.3-228.1. $^1$H-NMR (500 MHz, MeOD): δ 0.87 (d, J=7 Hz, 6H), 1.15 (d, J=7 Hz, 6H), 2.94 (m, 3H), 3.47 (t, J=8.5 Hz, 2H), 4.94 (t, J=6.5 Hz, 1H), 6.13 (s, 1H), 6.54 (d, J=8 Hz, 1H), 6.68 (m, 2H), 6.86 (s, 1H).

1-methyl-5-nitro-1H-indole (89)

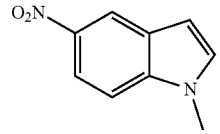

A mixture of 5-nitroindole (2 g, 12.33 mmol), NaH (0.6 g, 15 mmole) and DMF (10 ml) was added methyl iodide (1.5 ml, 24.09 mmol) at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:4, Rf=0.2) to afford 89 (2 g, 91.71%) as a yellow solid. $^1$H-NMR (500 MHz, CDCl$_3$): δ 3.86 (s 3H), 6.67 (d, J=3 Hz, 1H), 7.20 (d, J=3 Hz, 1H), 7.33 (d, J=9 Hz, 1H), 8.13 (m, 1H), 8.58 (d, =2 Hz, 1H).

1-methyl-6-nitro-1H-indole (90)

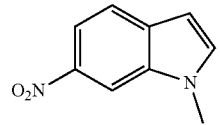

1-methyl-7-nitro-1H-indole (91)

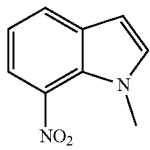

2,4-bis(benzyloxy)-5-isopropyl-N-(1-methyl-1H-indol-5-yl)benzamide (92)

The title compound was prepared using a mixture of 89 (1.50 g, 8.51 mmol) dissolved in IPA (68 ml) and H₂O (17 ml) and similar process as mentioned herein to afford 92 (0.96 g, 35.82%) as a white solid. $^1$H-NMR (500 MHz, CDCl₃): δ 1.28 (d, J=7 Hz, 6H), 3.36 (qui, J=7 Hz, 1H), 3.73 (s, 3H), 5.15 (s, 2H), 5.16 (s, 2H), 6.36 (d, J=3 Hz, 1H), 6.62 (s, 1H), 7.02 (m, 2H), 7.11 (d, J=8.5 Hz, 1H), 7.35 (t, J=7 Hz, 1H), 7.46 (m, 10H), 7.70 (d, J=1.5 Hz, 1H), 8.24 (s, 1H), 9.86 (d, 1H).

2,4-bis(benzyloxy)-5-isopropyl-N-(1-methyl-1H-indol-6-yl)benzamide (93)

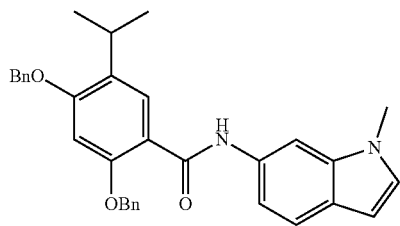 [SMILES: CC(C)c1cc(C(=O)Nc2ccc3ccn(C)c3c2)c(OCc2ccccc2)cc1OCc1ccccc1]

2,4-bis(benzyloxy)-5-isopropyl-N-(1-methyl-1H-indol-7-yl)benzamide (93)

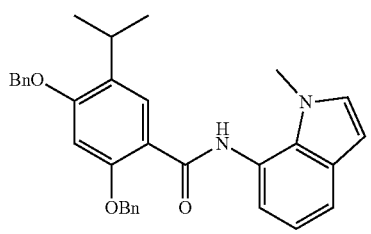 [SMILES: CC(C)c1cc(C(=O)Nc2cccc3ccn(C)c23)c(OCc2ccccc2)cc1OCc1ccccc1]

2,4-dihydroxy-5-isopropyl-N-(1-methyl-1H-indol-5-yl)benzamide (20f)

A mixture of 92 (0.40 g, 0.79 mmol), 10% palladium on activated carbon (0.04 g, 0.04 mmol) and MeOH (8 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:1, Rf=0.3) to afford 20f (0.21 g, 80.77%) as a pink solid. m.p. 221.2-223.8. $^1$H-NMR (500 MHz, MeOD): δ 1.25 (d, J=7 Hz, 6H), 3.21 (Sep, J=7 Hz, 1H), 3.75 (s, 1H), 6.35 (s, 1H), 6.39 (d, J=3 Hz, 1H), 7.11 (d, J=3 Hz, 1H), 7.27 (m, 1H), 7.31 (d, J=8.5 Hz, 1H), 7.74 (d, J=1.5 Hz, 1H), 7.77 (s, 1H).

2,4-dihydroxy-5-isopropyl-N-methyl-N-(1-methyl-1H-indol-5-yl)benzamide (20 g)

The title compound was prepared using a mixture of 92 (0.36 g, 0.71 mmol), NaH (0.04 g, 1 mmole) and DMF (4 ml) and similar process as mentioned herein to afford 20 g (0.18 g, 75.0%) as a white solid. m.p. 157.2-158.4. $^1$H-NMR (500 MHz, MeOD): δ 0.49 (d, J=6.5 Hz, 6H), 2.74 (qui, J=7 Hz, 1H), 3.46 (s, 3H), 3.78 (s, 3H), 6.15 (s, 1H), 6.39 (d, J=8 Hz, 1H), 6.45 (s, 1H), 7.00 (m, 1H), 7.18 (d, J=3 Hz, 1H), 7.35 (d, J=5 Hz, 1H), 7.37 (s, 1H).

N-ethyl-2,4-dihydroxy-5-isopropyl-N-(1-methyl-1H-indol-5-yl)benzamide (20 h)

The title compound was prepared using a mixture of 92 (0.35 g, 0.69 mmol), NaH (0.04 g, 1 mmole) and DMF (4 ml) and similar process as mentioned herein to afford 20 h (0.17 g, 70.83%) as a white solid. m.p. 167.6-169.8. $^1$H-NMR (500 MHz, MeOD): δ 0.47 (d, J=6.5 Hz, 6H), 1.19 (t, J=7 Hz, 3H), 2.73 (Sex, J=7 Hz, 1H), 3.74 (s, 3H), 3.93 (q, J=7 Hz, 2H), 6.17 (s, 1H), 6.37 (d, J=3 Hz, 1H), 6.44 (s, 1H), 6.95 (m, 1H), 7.15 (d, J=3 Hz, 1H), 7.31 (m 2H).

2,4-dihydroxy-5-isopropyl-N-(1-methyl-1H-indol-5-yl)-N-propylbenzamide (20i)

The title compound was prepared using a mixture of 92 (0.40 g, 0.79 mmol), NaH (0.04 g, 1 mmole) and DMF (4 ml) and similar process as mentioned herein to afford 20i (0.2 g, 68.96%) as a white solid. m.p. 179.9-182.4. $^1$H-NMR (500 MHz, MeOD): δ 0.49 (d, J=6.5 Hz, 6H), 0.93 (t, J=7 Hz, 3H), 1.66 (Sex, J=7.5 Hz, 2H), 2.73 (Sex, J=7 Hz, 1H), 3.77 (s, 1H), 3.87 (t, J=7.5 Hz, 2H), 6.15 (s, 1H), 6.38 (d, J=2.5 Hz, 1H), 6.43 (s, 1H), 6.97 (m, 1H), 7.17 (d, J=3 Hz, 1H), 7.33 (m, 2H).

2,4-dihydroxy-5-isopropyl-N-(1-methyl-1H-indol-6-yl)benzamide (21b)

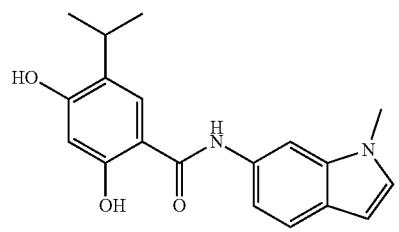 [SMILES: CC(C)c1cc(C(=O)Nc2ccc3ccn(C)c3c2)c(O)cc1O]

2,4-dihydroxy-5-isopropyl-N-methyl-N-(1-methyl-1H-indol-6-yl)benzamide (21c)

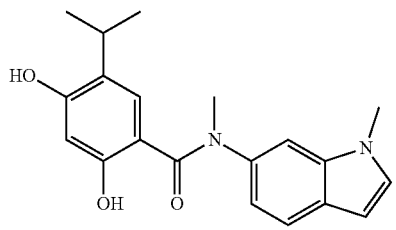 [SMILES: CC(C)c1cc(C(=O)N(C)c2ccc3ccn(C)c3c2)c(O)cc1O]

2,4-dihydroxy-5-isopropyl-N-(1-methyl-1H-indol-7-yl)benzamide (22a)

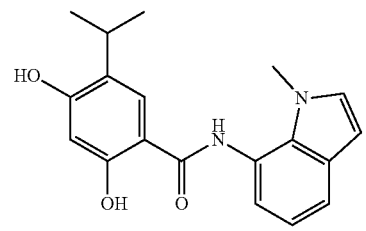

N-ethyl-2,4-dihydroxy-5-isopropyl-N-(1-methyl-1H-indol-6-yl)benzamide (21d)

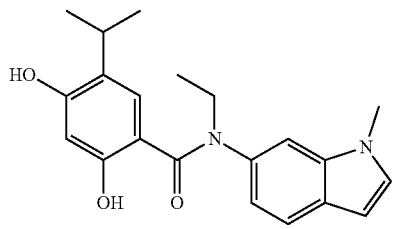 [SMILES: CCN(C(=O)c1cc(C(C)C)c(O)cc1O)c1ccc2ccn(C)c2c1]

2,4-dihydroxy-5-isopropyl-N-methyl-N-(1-methyl-1H-indol-7-yl)benzamide (22b)

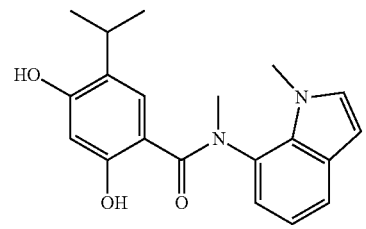

2,4-dihydroxy-5-isopropyl-N-(1-methyl-1H-indol-6-yl)-N-propylbenzamide (21e)

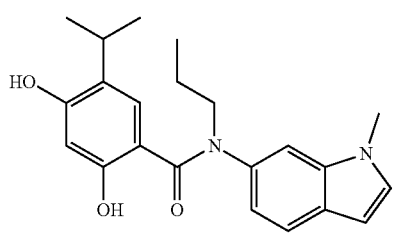 [SMILES: CCCN(C(=O)c1cc(C(C)C)c(O)cc1O)c1ccc2ccn(C)c2c1]

N-ethyl-2,4-dihydroxy-5-isopropyl-N-(1-methyl-1H-indol-7-yl)benzamide (22c)

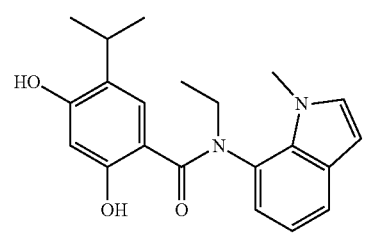

2,4-dihydroxy-N,5-diisopropyl-N-(1-methyl-1H-indol-6-yl)benzamide (21f)

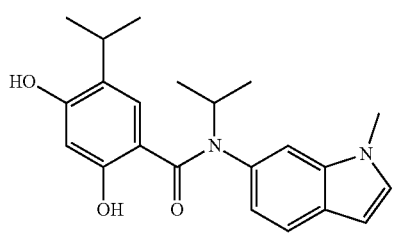 [SMILES: CC(C)c1cc(C(=O)N(c2ccc3ccn(C)c3c2)C(C)C)c(O)cc1O]

2,4-dihydroxy-5-isopropyl-N-(1-methyl-1H-indol-7-yl)-N-propylbenzamide (22d)

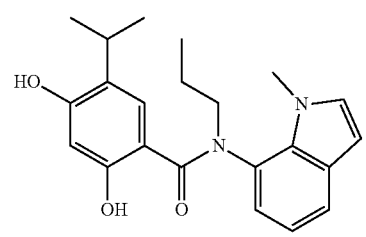 [SMILES: CCCN(C(=O)c1cc(C(C)C)c(O)cc1O)c1cccc2ccn(C)c12]

2,4-dihydroxy-N,5-diisopropyl-N-(1-methyl-1H-indol-7-yl)benzamide (22e)

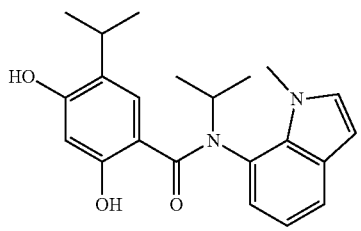 [SMILES: CC(C)c1cc(C(=O)N(c2cccc3ccn(C)c23)C(C)C)c(O)cc1O]

1-methyl-5-nitroindoline (96)

A mixture of 5-nitroindoline (2 g, 12.33 mmol), NaH (0.6 g, 15 mmole) and DMF (10 ml) was added methyl iodide (1.5 ml, 24.09 mmol) at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.5) to afford 96 (1.93 g, 87.72%) as a orange solid. $^1$H-NMR (500 MHz, CDCl$_3$): δ 2.90 (s, 3H), 3.05 (t, J=8.5 Hz, 2H), 3.62 (t, J=8.5 Hz, 2H), 6.25 (d, J=9 Hz, 1H), 7.86 (s, 1H), 8.05 (m, 1H).

2,4-bis(benzyloxy)-5-isopropyl-N-(1-methylindolin-5-yl)benzamide (97)

A mixture of 96 (1.50 g, 8.51 mmol) was dissolved in IPA (68 ml) and H$_2$O (17 ml) and added iron powder (2.5 g, 45.45 mmol) and NH$_4$Cl (2 g, 37.04 mmol). The reaction was stirred and reflux for 1 h. The iron powder was removed by methyl alcohol wash through celite packing. The organic layer was concentrated in vacuo and without more purification. To the mixture of 46 (2 g, 5.31 mmol), EDC.HCl (1.5 g, 7.85 mmol), HOBt (0.9 g, 6.67 mmol), NMM (1.4 ml, 12.75 mmol) and DMF (8 ml) was stirred for 10 min then added crude product at room temperature for overnight, the reaction was quenched with water and extracted with ethyl acetate (30 ml*3). The organic layer was collected and dried over anhydrous MgSO$_4$ concentrated in vacuo to yield colorless oil product. The residue was purified by silica gel chromatography (ethyl acetate:n-hexane=1:2, Rf=0.6) to afford 97 (1.24 g, 45.93%) as a yellow solid. $^1$H-NMR (500 MHz, CDCl$_3$): δ 1.26 (d, J=7 Hz, 6H), 2.71 (s, 3H), 2.86 (t, J=7 Hz, 2H), 3.24 (s, 2H), 3.34 (Sep, J=7 Hz, 1H), 5.13 (s, 2H), 5.14 (s, 2H), 6.32 (d, J=8 Hz, 1H), 6.60 (s, 1H), 6.89 (d, J=7.5 Hz, 1H), 7.16 (s, 1H), 7.44 (m, 10H), 8.20 (s, 1H), 9.68 (s, 1H).

2,4-dihydroxy-5-isopropyl-N-(1-methylindolin-5-yl)benzamide (23f)

A mixture of 97 (0.32 g, 0.63 mmol), 10% palladium on activated carbon (0.04 g, 0.04 mmol) and MeOH (8 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 23f (0.17 g, 80.95%) as a yellow oil. $^1$H-NMR (500 MHz, CDCl$_3$): δ 1.25 (d, J=7 Hz, 6H), 2.75 (s, 3H), 2.96 (d, J=5 Hz, 2H), 3.16 (qui, J=7 Hz, 1H), 3.31 (s, 2H), 6.34 (s, 1H), 6.45 (d, J=8 Hz, 1H), 7.10 (d, J=8 Hz, 1H), 7.21 (s, 1H), 7.26 (m, 1H), 7.67 (s, 1H).

N-ethyl-2,4-dihydroxy-5-isopropyl-N-(1-methylindolin-5-yl)benzamide (23 g)

The title compound was prepared using a mixture of 97 (0.35 g, 0.69 mmol), NaH (0.04 g, 1 mmole) and DMF (4 ml) and similar process as mentioned herein to afford 23 g (0.17 g, 70.83%) as a white solid. m.p. 136.5-138.3. $^1$H-NMR (500 MHz, MeOD): δ 0.78 (d, J=6.5 Hz, 6H), 1.16 (t, J=7 Hz, 3H), 2.70 (s, 3H), 2.85 (t, J=8 Hz, 2H), 2.91 (qui, J=7 Hz, 1H), 3.25 (t, J=8 Hz, 2H), 3.82 (q, J=7 Hz, 2H), 6.18 (s, 1H), 6.42 (d, J=8.5 Hz, 1H), 6.63 (s, 1H), 6.77 (m, 1H), 6.84 (s, 1H).

2,4-dihydroxy-5-isopropyl-N-(1-methylindolin-5-yl)-N-propylbenzamide (23 h)

The title compound was prepared using a mixture of 97 (0.33 g, 0.65 mmol), NaH (0.04 g, 1 mmole) and DMF (4 ml) and similar process as mentioned herein to afford 23 h (0.16 g, 66.67%) as a white solid. m.p. 132.0-133.9. $^1$H-NMR (500 MHz, MeOD): δ 0.79 (d, J=7 Hz, 6H), 0.91 (t, J=7.5 Hz, 3H), 1.62 (Sex, J=7.5 Hz, 2H), 2.71 (s, 3H), 2.85 (t, J=8 Hz, 2H), 2.91 (qui, J=7 Hz, 1H), 3.26 (t, J=8 Hz, 2H), 3.74 (m, 2H), 6.17 (s, 1H), 6.42 (d, J=8.5 Hz, 1H), 6.62 (s, 1H), 6.78 (m, 1H), 6.85 (s, 1H).

5-nitro-1H-pyrrolo[2,3-b]pyridine (99)

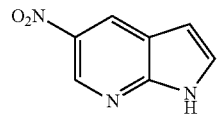

1-methyl-5-nitro-1H-pyrrolo[2,3-b]pyridine (100)

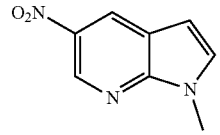

2,4-bis(benzyloxy)-5-isopropyl-N-(1H-pyrrolo[2,3-b]pyridin-5-yl)benzamide (101)

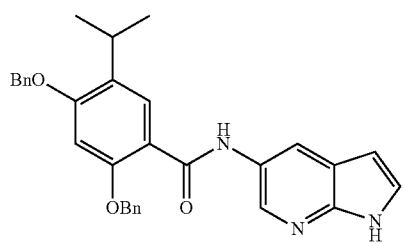 [SMILES: CC(C)c1cc(C(=O)Nc2cnc3[nH]ccc3c2)c(OCc2ccccc2)cc1OCc1ccccc1]

77

2,4-bis(benzyloxy)-5-isopropyl-N-(1-methyl-1H-pyrrolo[2,3-b]pyridin-5-yl)benzamide (102)

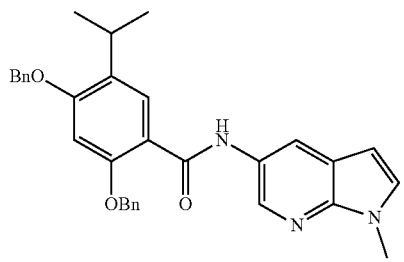 [SMILES: CC(C)c1cc(C(=O)Nc2cnc3c(ccn3C)c2)c(OCc2ccccc2)cc1OCc1ccccc1]

2,4-dihydroxy-5-isopropyl-N-(1H-pyrrolo[2,3-b]pyridin-5-yl)benzamide (24a)

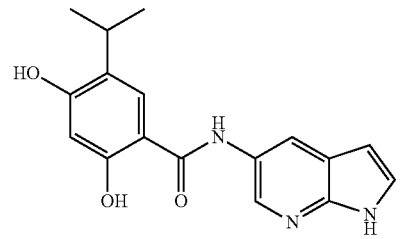 [SMILES: CC(C)c1cc(C(=O)Nc2cnc3[nH]ccc3c2)c(O)cc1O]

2,4-dihydroxy-5-isopropyl-N-(1-methyl-1H-pyrrolo[2,3-b]pyridin-5-yl)benzamide (24b)

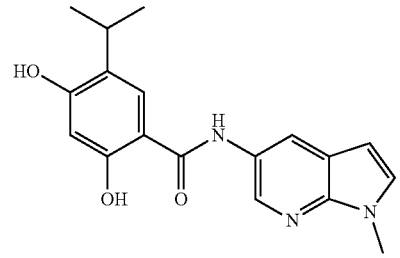 [SMILES: CC(C)c1cc(C(=O)Nc2cnc3c(ccn3C)c2)c(O)cc1O]

2,4-dihydroxy-5-isopropyl-N-methyl-N-(1-methyl-1H-pyrrolo[2,3-b]pyridin-5-yl)benzamide (24c)

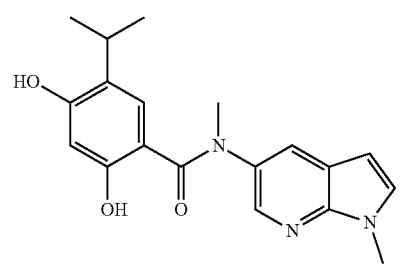 [SMILES: CC(C)c1cc(C(=O)N(C)c2cnc3c(ccn3C)c2)c(O)cc1O]

78

N-ethyl-2,4-dihydroxy-5-isopropyl-N-(1-methyl-1H-pyrrolo[2,3-b]pyridin-5-yl)benzamide (24d)

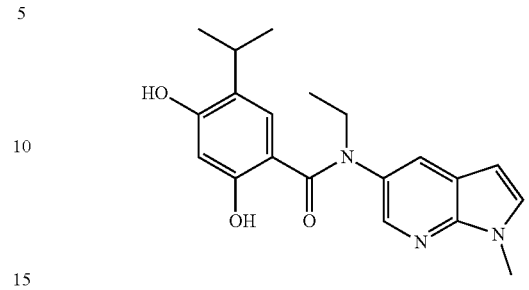

2,4-dihydroxy-5-isopropyl-N-(1-methyl-1H-pyrrolo[2,3-b]pyridin-5-yl)-N-propylbenzamide (24e)

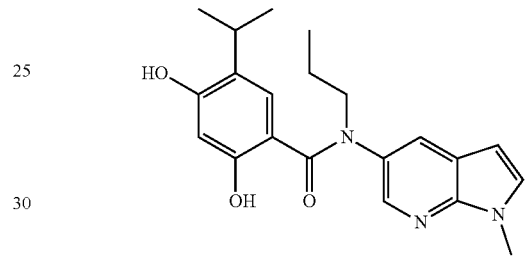

2,4-dihydroxy-N, 5-diisopropyl-N-(1-methyl-1H-pyrrolo[2,3-b]pyridin-5-yl)benzamide (24f)

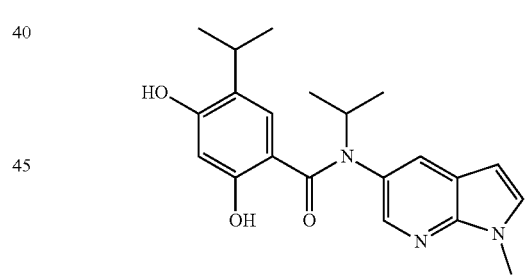

2,4-bis(benzyloxy)-N-(1H-indazol-5-yl)-5-isopropylbenzamide (104)

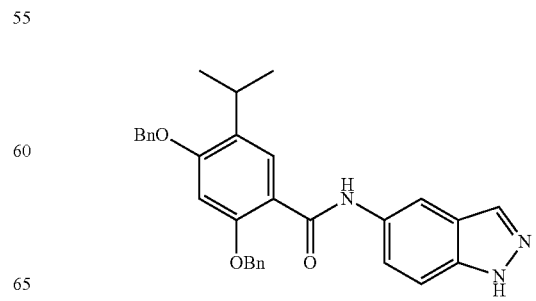

79

2,4-dihydroxy-N-(1H-indazol-5-yl)-5-isopropylbenzamide (25a)

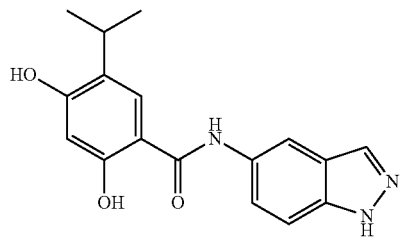 [SMILES: CC(C)c1cc(C(=O)Nc2ccc3[nH]ncc3c2)c(O)cc1O]

2,4-dihydroxy-5-isopropyl-N-methyl-N-(1-methyl-1H-indazol-5-yl)benzamide (25b)

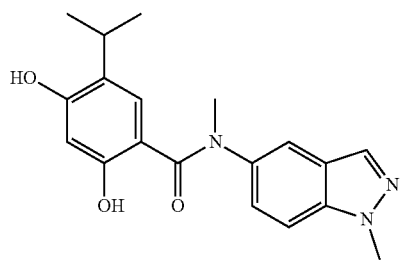 [SMILES: CC(C)c1cc(C(=O)N(C)c2ccc3c(cnn3C)c2)c(O)cc1O]

5-nitro-1H-pyrazolo[3,4-b]pyridine (106)

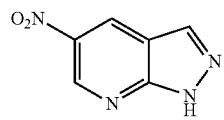 [SMILES: O=[N+]([O-])c1cnc2[nH]ncc2c1]

1-methyl-5-nitro-1H-pyrazolo[3,4-b]pyridine (107)

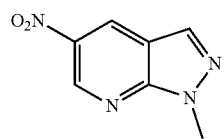

80

2,4-bis(benzyloxy)-5-isopropyl-N-(1H-pyrazolo[3,4-b]pyridin-5-yl)benzamide (108)

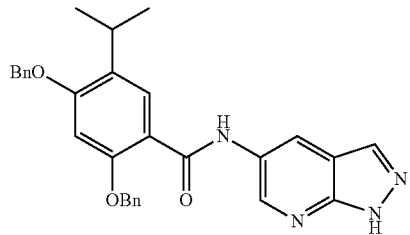 [SMILES: CC(C)c1cc(C(=O)Nc2cnc3[nH]ncc3c2)c(OCc2ccccc2)cc1OCc1ccccc1]

2,4-bis(benzyloxy)-5-isopropyl-N-(1-methyl-1H-pyrazolo[3,4-b]pyridin-5-yl)benzamide (109)

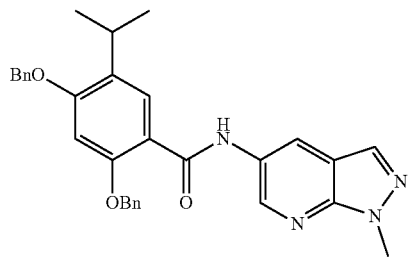 [SMILES: CC(C)c1cc(C(=O)Nc2cnc3c(cnn3C)c2)c(OCc2ccccc2)cc1OCc1ccccc1]

2,4-dihydroxy-5-isopropyl-N-(1H-pyrazolo[3,4-b]pyridin-5-yl)benzamide (26a)

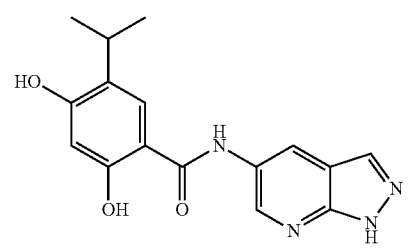 [SMILES: CC(C)c1cc(C(=O)Nc2cnc3[nH]ncc3c2)c(O)cc1O]

2,4-dihydroxy-5-isopropyl-N-(1-methyl-1H-pyrazolo[3,4-b]pyridin-5-yl)benzamide (26b)

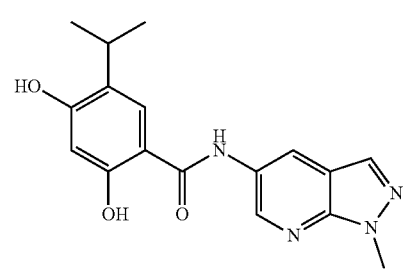 [SMILES: CC(C)c1cc(C(=O)Nc2cnc3c(cnn3C)c2)c(O)cc1O]

81

2,4-dihydroxy-5-isopropyl-N-methyl-N-(1-methyl-1H-pyrazolo[3,4-b]pyridin-5-yl)benzamide (26c)

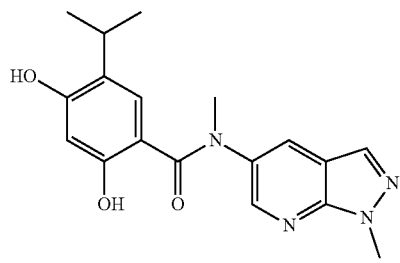 [SMILES: CC(C)c1cc(C(=O)N(C)c2cnc3c(cnn3C)c2)c(O)cc1O]

N-ethyl-2,4-dihydroxy-5-isopropyl-N-(1-methyl-1H-pyrazolo[3,4-b]pyridin-5-yl)benzamide (26d)

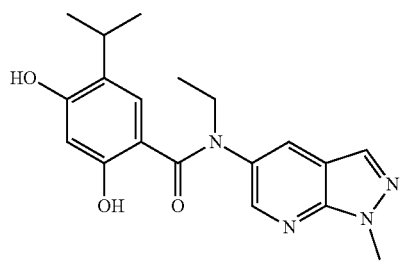 [SMILES: CCN(C(=O)c1cc(C(C)C)c(O)cc1O)c1cnc2c(cnn2C)c1]

2,4-dihydroxy-5-isopropyl-N-(1-methyl-1H-pyrazolo[3,4-b]pyridin-5-yl)-N-propylbenzamide (26e)

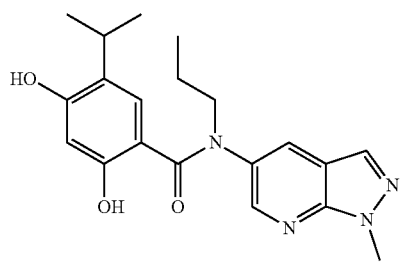 [SMILES: CCCN(C(=O)c1cc(C(C)C)c(O)cc1O)c1cnc2c(cnn2C)c1]

2,4-dihydroxy-N, 5-diisopropyl-N-(1-methyl-1H-pyrazolo[3,4-b]pyridin-5-yl)benzamide (26f)

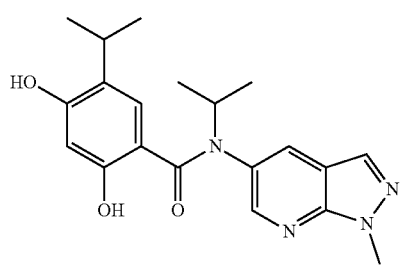 [SMILES: CC(C)c1cc(C(=O)N(c2cnc3c(cnn3C)c2)C(C)C)c(O)cc1O]

82

7-methyl-7H-pyrrolo[2,3-d]pyrimidin-4-amine (111)

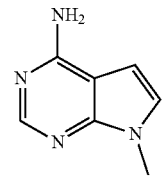

2,4-bis(benzyloxy)-5-isopropyl-N-(7-methyl-7H-pyrrolo[2,3-d]pyrimidin-4-yl)benzamide (112)

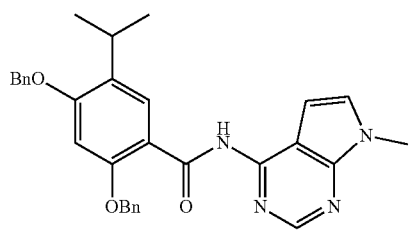 [SMILES: CC(C)c1cc(C(=O)Nc2ncnc3c2ccn3C)c(OCc2ccccc2)cc1OCc1ccccc1]

2,4-dihydroxy-5-isopropyl-N-(7-methyl-7H-pyrrolo[2,3-d]pyrimidin-4-yl)benzamide (27a)

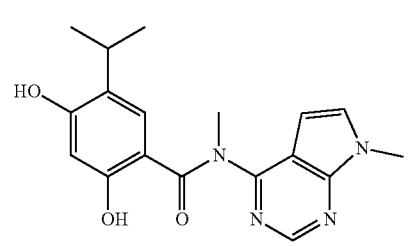 [SMILES: CC(C)c1cc(C(=O)N(C)c2ncnc3c2ccn3C)c(O)cc1O]

2,4-dihydroxy-5-isopropyl-N-methyl-N-(7-methyl-7H-pyrrolo[2,3-d]pyrimidin-4-yl)benzamide (27b)

N-ethyl-2,4-dihydroxy-5-isopropyl-N-(7-methyl-7H-pyrrolo[2,3-d]pyrimidin-4-yl)benzamide (27c)

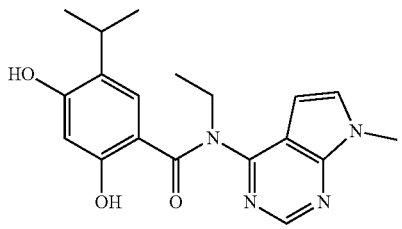

2,4-dihydroxy-5-isopropyl-N-(7-methyl-7H-pyrrolo[2,3-d]pyrimidin-4-yl)-N-propylbenzamide (27d)

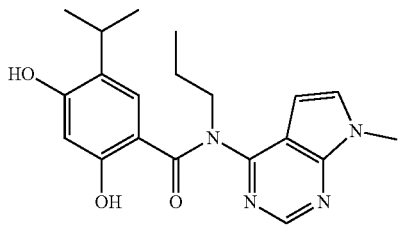 [SMILES: CCCN(C(=O)c1cc(C(C)C)c(O)cc1O)c1ncnc2c1ccn2C]

2,4-dihydroxy-N, 5-diisopropyl-N-(7-methyl-7H-pyrrolo[2,3-d]pyrimidin-4-yl)benzamide (27e)

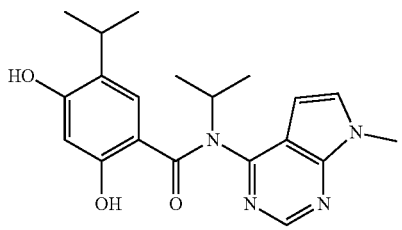 [SMILES: CC(C)c1cc(C(=O)N(c2ncnc3c2ccn3C)C(C)C)c(O)cc1O]

2,4-bis(benzyloxy)-5-isopropyl-N-(quinolin-3-yl)benzamide (113)

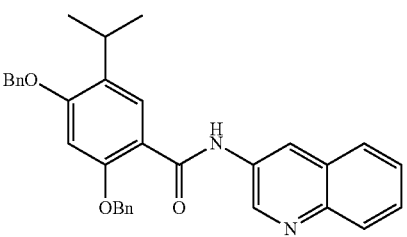 [SMILES: CC(C)c1cc(C(=O)Nc2cnc3ccccc3c2)c(OCc2ccccc2)cc1OCc1ccccc1]

The title compound was prepared using a mixture of 47 (1.28 g, 3.40 mmol), EDC.HCl (0.97 g, 5.06 mmol), HOBt (0.55 g, 4.07 mmol), NMM (0.9 ml, 8.19 mmol) and DMF (5 ml) and similar process as mentioned herein to afford 113 (1.03 g, 61%). $^1$H-NMR (300 MHz, CDCl$_3$): δ 1.29 (d, J=6.9 Hz, 6H), 3.37 (qui, J=6.9 Hz, 1H), 5.19 (s, 2H), 5.20 (s, 2H), 7.35-7.64 (m, 13H), 7.74-7.78 (m, 1H), 8.00-8.15 (m, 2H), 8.22 (s, 1H), 8.83 (d, J=2.4 Hz, 1H), 10.22 (s, 1H).

2,4-bis(benzyloxy)-5-isopropyl-N-(quinolin-5-yl)benzamide (114)

A mixture of 47 (1.28 g, 3.40 mmol), EDC.HCl (0.97 g, 5.06 mmol), 4-dimethyl-aminopyridine (0.42 g, 3.40 mmol) and DCM (5 ml) was stirred for 10 min then added 6-aminoquinoline (0.49 g, 3.40 mmol) for overnight, the reaction was quenched with water and extracted with DCM (30 ml*3). The organic layer was collected and dried over anhydrous MgSO$_4$ concentrated in vacuo to yield crude product. The residue was purified by silica gel chromatography (ethyl acetate:n-hexane=1:2) to afford 114 (0.93 g, 54%). $^1$H-NMR (300 MHz, CDCl$_3$): δ 1.29 (d, J=6.6 Hz, 6H), 3.38 (qui, J=6.9 Hz, 1H), 5.20 (s, 2H), 5.22 (s, 2H), 6.72 (s, 1H), 7.00-7.07 (m, 1H), 7.34-7.50 (m, 11H), 7.69-7.90 (m, 2H), 8.09 (d, J=8.4 Hz, 1H), 8.25 (s, 1H), 8.34 (d, J=7.8 Hz, 1H), 8.8 (d, J=4.2 Hz, 1H).

2,4-bis(benzyloxy)-5-isopropyl-N-(quinolin-6-yl)benzamide (115)

The title compound was prepared using a mixture of 47 (1.28 g, 3.40 mmol), EDC.HCl (0.97 g, 5.06 mmol), 4-dimethyl-aminopyridine (0.42 g, 3.40 mmol) and DCM (5 ml) and similar process as mentioned herein to afford 115 (0.91 g, 53%). $^1$H-NMR (300 MHz, CDCl$_3$): δ 1.31 (d, J=6.9 Hz, 6H), 3.38 (qui, J=6.9 Hz, 1H), 5.16 (s, 4H), 6.63 (s, 1H), 6.96 (dd, J=6.6, 9 Hz, 1H), 7.24-7.60 (m, 12H), 7.86 (d, J=9 Hz, 1H), 8.01 (d, J=8.1 Hz, 1H), 8.25-8.30 (m, 2H), 8.75 (dd, J=2.4, 3.9 Hz, 1H), 10.14 (s, 1H).

2,4-bis(benzyloxy)-5-isopropyl-N-(quinolin-8-yl)benzamide (116)

The title compound was prepared using a mixture of 47 (1.28 g, 7.97 mmol), EDC.HCl (0.97 g, 5.06 mmol), HOBt (0.55 g, 4.07 mmol), NMM (0.9 ml, 8.19 mmol) and DMF (5 ml) and similar process as mentioned herein to afford 116 (0.78 g, 45.64%) as a white solid. $^1$H-NMR (300 MHz, CDCl$_3$): δ 1.20 (d, J=6.6 Hz, 6H), 3.25 (qui, J=6.9 Hz, 1H), 4.90 (s, 2H), 5.30 (s, 2H), 6.44 (s, 1H), 7.13-8.19 (m, 11H), 8.33 (m, 1H), 8.34 (s, 1H), 8.99 (d, J=0.9 Hz, 1H), 9.02 (d, J=0.9 Hz, 1H), 12.25 (s, 1H).

2,4-bis(benzyloxy)-5-isopropyl-N-(2-methylquinolin-4-yl)benzamide (117)

The title compound was prepared using a mixture of 47 (1.42 g, 3.79 mmol), EDC.HCl (1.09 g, 5.69 mmol), HOBt (0.55 g, 4.07 mmol), NMM (1.0 ml, 9.10 mmol) and DMF (5 ml) and similar process as mentioned herein to afford 117 (0.97 g, 49%). $^1$H-NMR (300 MHz, CDCl$_3$): δ 1.27 (d, J=6.9 Hz, 6H), 2.68 (s, 3H), 3.34-3.39 (m, 1H), 5.27 (s, 2H), 5.42 (s, 2H), 7.00-7.10 (m, 2H), 7.26-7.62 (m, 13H), 7.86 (d, J=8.4 Hz, 1H), 8.11 (s, 1H), 8.39 (s, 1H).

2,4-dihydroxy-5-isopropyl-N-(quinolin-3-yl)benzamide (28a)

A mixture of 113 (0.1 g, 0.19 mmol) in ethanol (10 mL) was added 10% palladium on activated carbon (cat.). The mixture was stirred under H$_2$ for 6 hr. The reaction was filtered through celite packing and the organic layer was concentrated in vacuo and purified by silica gel chromatography (EtOAc: n-hexane=1:1) to afford 28a (0.10 g, 31%). m.p. 232.0-234.5. $^1$H-NMR (300 MHz, DMSO): δ 1.20 (d, J=6.9 Hz, 6H), 3.13 (qui, J=6.9 Hz, 1H), 6.43 (s, 1H), 7.55-7.72 (m, 2H), 7.82 (s, 1H), 7.93-8.01 (m, 2H), 8.70 (d, J=2.4 Hz, 1H), 9.06 (d, J=2.7 Hz, 1H), 10.22 (s, 1H), 10.58 (s, 1H).

2,4-dihydroxy-5-isopropyl-N-methyl-N-(quinolin-3-yl)benzamide (28b)

A mixture of 113 (1.00 g, 1.98 mmol) dissolved in acetonitrile (5 mL) was added cesium carbonate (0.65 g, 1.98 mmol). The mixture was heated at 60-70° C. and stirred for 30 min. The reaction was quenched with water and extracted with ethyl acetate (30 ml*3). The organic layer was collected and dried over anhydrous MgSO$_4$ concentrated in vacuo to yield colorless oil product. The residue was purified by silica gel chromatography (ethyl acetate:n-hexane=1:4) to afford product. To a solution of this product was dissolved in ethanol (10 mL) and stirred under H$_2$ at room temperature for 3 hr. The reaction was filtered through celite packing and the organic layer was concentrated in vacuo and purified by silica gel chromatography (EtOAc:n-hexane=1:4) to afford 28b (0.04 g, 79%). m.p. 236.9-238.6. $^1$H-NMR (300 MHz, d-Acetone): δ 1.27 (d, J=7.2 Hz, 10H), 3.26 (qui, J=7.2 Hz, 1H), 3.84 (s, 3H), 6.53 (s, 1H), 7.29-7.37 (m, 1H), 7.55-7.59 (m, 2H), 7.70-7.77 (m, 2H), 8.82 (s, 1H), 9.20 (s, 1H), 10.20 (s, 1H), 11.35 (s, 1H).

N-ethyl-2,4-dihydroxy-5-isopropyl-N-(quinolin-3-yl)benzamide (28c)

The title compound was prepared using a mixture of 113 (0.5 g, 1 mmol), NaH (0.05 g, 2 mmole) and DMF (5 ml) and similar process as mentioned herein to afford 28c (0.10 g, 73%). m.p. 207.2-209.8. $^1$H-NMR (500 MHz, MeOD): δ 0.70 (d, J=6.9 Hz, 6H), 1.26 (t, J=7.2 Hz, 3H), 2.80-2.94 (m, 1H), 4.04-4.14 (m, 2H), 6.11 (s, 1H), 6.67 (s, 1H), 7.57-7.65 (m, 1H), 7.70-7.79 (m, 1H), 7.88 (d, J=8.4 Hz, 1H), 7.96 (d, J=8.7 Hz, 1H), 8.21 (d, J=2.4 Hz, 1H), 8.55 (d, J=2.4 Hz, 1H).

2,4-dihydroxy-5-isopropyl-N-propyl-N-(quinolin-3-yl)benzamide (28d)

The title compound was prepared using a mixture of compound 113 (0.35 g, 0.90 mmol) in tetrahydrofuran (5 mL) and potassium tert-butoxide (0.15 g, 1.35 mmol) and similar process as mentioned herein to afford 28d (0.04 g, 13%). m.p. 197.8-199.5. $^1$H-NMR (300 MHz, CDCl$_3$): δ 0.42 (d, J=6.9 Hz, 6H), 0.96 (t, J=7.2 Hz, 3H), 1.65-1.79 (m, 2H), 2.75 (qui, J=6.9 Hz, 1H), 3.93-4.01 (m, 2H), 6.29 (s, 1H), 6.37 (s, 1H), 7.53-7.63 (m, 1H), 7.67-7.81 (m, 2H), 7.96 (d, J=2.4 Hz, 1H), 8.08 (d, J=8.4 Hz, 1H), 8.58 (d, J=2.7 Hz, 1H), 10.93 (s, 1H).

2,4-dihydroxy-5-isopropyl-N-(quinolin-5-yl)benzamide (29a)

A mixture of 114 (0.2 g, 0.40 mmol) in methanol (15 mL) was added 10% palladium on activated carbon (cat.) and formic acid (0.9 mL, 23.85 mmol). The mixture was stirred under H$_2$ for 12 hr. The reaction was filtered through celite packing and the organic layer was concentrated in vacuo and purified by silica gel chromatography (EtOAc:n-hexane=1: 1) to afford 29a (0.06 g, 45%). m.p. 222.0-224.5. $^1$H-NMR (300 MHz, MeOD): δ 1.26 (d, J=7.2 Hz, 7H), 3.18-3.24 (m, 1H), 6.4 (s, 1H), 7.56-7.63 (m, 1H), 7.78-7.99 (m, 4H), 8.48 (d, J=9 Hz, 1H), 8.88 (d, J=3.9 Hz, 1H).

2,4-dihydroxy-5-isopropyl-N-methyl-N-(quinolin-5-yl)benzamide (29b)

The title compound was prepared using a mixture of 29a (0.10 g, 0.31 mmol) in DCM (5 mL), tert-butyldimethylsilyl chloride (0.09 g, 0.62 mmol) and DIPEA (0.08 g, 0.62 mmol) and similar process as mentioned hereinto afford 29b (0.02 g, 71%). $^1$H-NMR (300 MHz, MeOD): δ 1.22-1.30 (m, 9H), 3.20-3.28 (m, 1H), 4.09 (s, 3H), 6.63 (s, 1H), 7.63 (q, J=4.5 Hz, 1H), 7.84 (m, 1H), 7.95 (m, 2H), 8.06 (d, J=7.5 Hz, 1H), 8.48 (dd, J=1.2, 8.4 Hz, 1H), 8.87-8.91 (m, 1H).

N-ethyl-2,4-dihydroxy-5-isopropyl-N-(quinolin-5-yl)benzamide (29c)

The title compound was prepared using a mixture of 29a (0.10 g, 0.31 mmol) in DCM (5 mL), tert-butyldimethylsilyl chloride (0.09 g, 0.62 mmol) and DIPEA (0.08 g, 0.62 mmol) and similar process as mentioned herein to afford 29c (0.02 g, 33%). m.p. 152.3-154.9. $^1$H-NMR (300 MHz, MeOD): δ 1.24 (d, J=6.9 Hz, 6H), 1.57 (t, J=6.9 Hz, 3H), 3.16-3.28 (m, 1H), 4.33 (q, J=6.9 Hz, 2H), 6.61 (s, 1H), 7.74-7.81 (m, 1H), 7.89-8.01 (m, 3H), 8.15 (d, J=6.9 Hz, 1H), 8.76 (d, J=8.4 Hz, 1H), 9.00 (s, 1H).

2,4-dihydroxy-5-isopropyl-N-(quinolin-6-yl)benzamide (30a)

A mixture of 115 (0.1 g, 0.19 mmol) in methanol (10 mL) was added 10% palladium on activated carbon (cat.). The mixture was stirred under H$_2$ for 12 hr. The reaction was filtered through celite packing and the organic layer was concentrated in vacuo and purified by silica gel chromatography (EtOAc:n-hexane=1:1) to afford 30a (0.04 g, 63%). m.p. 162.1-164.2. $^1$H-NMR (300 MHz, DMSO): δ 1.20 (d, J=6.9 Hz, 6H), 3.14 (qui, J=6.9 Hz, 1H), 6.43 (s, 1H), 7.50 (q, J=4.2 Hz, 1H), 7.82 (s, 1H), 7.92-8.05 (m, 2H), 8.28-8.42 (m, 2H), 8.78-8.84 (m, 1H), 10.18 (s, 1H), 10.46 (s, 1H).

2,4-dihydroxy-5-isopropyl-N-methyl-N-(quinolin-6-yl)benzamide (30b)

The title compound was prepared using a mixture of 30a (0.61 g, 1.89 mmol) in DCM (15 mL), tert-butyldimethylsilyl chloride (0.57 g, 3.78 mmol) and DIPEA (0.49 g, 3.78 mmol) and similar process as mentioned herein to afford 30b (0.1 g, 40%). m.p. 277.5-279.8. $^1$H-NMR (300 MHz, DMSO): δ 1.17 (d, J=6.9 Hz, 6H), 3.10-3.22 (m, 1H), 3.93 (s, 3H), 6.60 (s, 1H), 7.46-7.53 (m, 1H), 7.69 (s, 1H), 7.93-7.99 (m, 2H), 8.28 (dd, J=1.5, 8.4 Hz, 1H), 8.51 (d, J=1.5 Hz, 1H), 8.76-8.82 (m, 1H), 10.13 (s, 1H).

N-ethyl-2,4-dihydroxy-5-isopropyl-N-(quinolin-6-yl)benzamide (30c)

The title compound was prepared using a mixture of 115 (0.40 g, 0.80 mmol) dissolved in tetrahydrofuran (5 ml), potassium tert-butoxide (0.13 g, 1.20 mmol) and ethyl iodide (3.30 mL) and similar process as mentioned herein to afford 30c (0.09 g, 38%). m.p. 220.8-221.2. $^1$H-NMR (300 MHz, DMSO): δ 0.57 (d, J=6.6 Hz, 6H), 1.14 (t, J=6.9 Hz, 3H), 2.71-2.77 (m, 1H), 3.93 (q, J=6.9 Hz, 2H), 6.12 (s, 1H), 6.53 (s, 1H), 7.49 (q, J=4.2 Hz, 1H), 7.58 (dd, J=2.4, 9 Hz, 1H), 7.76 (d, J=2.4 Hz, 1H), 7.94 (d, J=9 Hz, 1H), 8.23-8.28 (m, 1H), 8.83-8.87 (m, 1H).

2,4-dihydroxy-5-isopropyl-N-propyl-N-(quinolin-6-yl)benzamide (30d)

A mixture of 30a (0.61 g, 1.89 mmol) in DCM (15 mL) was added tert-butyldimethylsilyl chloride (0.57 g, 3.78 mmol) and DIPEA (0.49 g, 3.78 mmol). The mixture was stirred at room temperature for 12 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:2) to afford product. Then this product was dissolved in tetrahydrofuran (5 mL) and added potassium tert-butoxide (0.06 g, 0.51 mmol) and 1-iodopropane (1.65 mL) to the reaction solution and stirred at room temperature for 12 hours. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford product. Then this product was dissolved in DCM (3 ml) and added tetra-n-butylammonium fluoride (0.15 ml). The reaction solution was stirred at room temperature for 2 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford 30d (0.01 g, 13%). $^1$H-NMR (300 MHz, DMSO): δ 1.03 (t, J=7.5 Hz, 3H), 1.17 (d, J=6.9 Hz, 7H), 1.87-1.99 (m, 2H), 3.15 (t, J=6.9 Hz, 1H), 4.07 (t, J=6.6 Hz, 2H), 6.59 (s, 1H), 7.49 (q, J=4.2 Hz, 1H), 7.70 (s, 1H), 7.80 (dd, J=2.4, 9 Hz, 1H), 8.00 (d, J=9 Hz, 1H), 8.29 (d, J=6.6 Hz, 1H), 8.52 (d, J=2.4 Hz, 1H), 8.76-8.81 (m, 1H).

2,4-dihydroxy-5-isopropyl-N-(quinolin-8-yl)benzamide (31a)

A mixture of 116 (0.21 g, 0.42 mmol), 10% palladium on activated carbon (cat.) and MeOH (10 ml) was under the hydrogen gas. The reaction was stirred at room temperature for 12 h. The 10% palladium on activated carbon was removed by methyl alcohol wash through celite packing. The organic layer was concentrated in vacuo and purified by silica gel chromatography (ethyl acetate:n-hexane=1:2, Rf=0.4) to afford 31a (0.07 g, 51.70%) as a yellow solid. m.p. 172.5-174.6. H-NMR (300 MHz, MeOD): δ 1.27 (d, J=6.9 Hz, 6H), 3.23 (qui, J=6.9 Hz, 1H), 6.41 (s, 1H), 7.49-7.60 (m, 3H), 7.81 (s, 1H), 8.26 (dd, J=1.8, 8.4 Hz, 1H), 8.80 (dd, J=2.1, 6.9 Hz, 1H), 8.85 (dd, J=1.5, 4.2 Hz, 1H).

2,4-dihydroxy-5-isopropyl-N-methyl-N-(quinolin-8-yl)benzamide (31b)

A mixture of 31a (0.21 g, 0.65 mmol) in DCM (10 mL) was added tert-butyldimethylsilyl chloride (0.20 g, 1.30 mmol) and DIPEA (0.18 g, 1.30 mmol). The mixture was stirred at room temperature for 5 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:3) to afford product. Then this product was dissolved in tetrahydrofuran (5 ml) and added potassium tert-butoxide (0.03 g, 0.25 mmol) and methyl iodide (0.51 ml) to the reaction solution and stirred at room temperature for 4 hours. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:8) to afford product. Then this product was dissolved in DCM (3 ml) and added tetra-n-butylammonium fluoride (0.11 ml). The reaction solution was stirred at room temperature for 3 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford 31b (0.02 g, 9%). m.p. 229.5-231.5. $^1$H-NMR (300 MHz, d-Acetone): δ 1.27 (d, J=6.9 Hz, 6H), 3.03 (qui, J=6.9 Hz, 1H), 4.17 (s, 3H), 6.73 (s, 1H), 7.56-7.62 (m, 3H), 8.15 (s, 1H), 8.34 (dd, J=1.5, 8.1 Hz, 1H), 8.96-9.07 (m, 2H), 12.33 (s, 1H).

N-ethyl-2,4-dihydroxy-5-isopropyl-N-(quinolin-8-yl)benzamide (31c)

A mixture of compound 116 (0.35 g, 0.69 mmol) in tetrahydrofuran (5 mL) was added potassium tert-butoxide (0.12 g, 1.03 mmol). The mixture was stirred for 10 min and added ethyl iodide (2.85 mL) and stirred at room temperature for 6 hours. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:3) to afford product. A mixture of above product in ethanol was added formic acid (0.68 mL), 10% palladium on activated carbon (cat.). The resulting mixture was refluxed for 12 hr. After cooling to room temperature, The organic layer was concentrated in vacuo and purified by silica gel chromatography (ethyl acetate:n-hexane=1:2) to afford 31c (0.07 g, 66%). m.p. 82.5-85.9. $^1$H-NMR (300 MHz, CDCl$_3$): δ 1.21 (qui, J=7.2 Hz, 6H), 2.03 (s, 3H), 2.66 (t, J=6.9 Hz, 1H), 4.10 (q, J=7.2 Hz, 1H), 6.20 (s, 1H), 6.40 (s, 1H), 6.46 (s, 1H), 7.25-7.50 (m, 3H), 7.75 (dd, J=1.8, 7.8 Hz, 1H), 8.19 (dd, J=1.8, 8.4 Hz, 1H), 8.96 (dd, J=1.8, 4.2 Hz, 1H), 11.23 (s, 1H).

2,4-dihydroxy-5-isopropyl-N-(2-methylquinolin-4-yl)benzamide (32a)

A mixture of 117 (0.73 g, 1.41 mmol), 10%/a palladium on activated carbon (cat.) and MeOH (105 ml) was added formic acid (3.2 ml, 84.81 mmol). The reaction was stirred at room temperature for 12 h. The 10% palladium on activated carbon was removed by methyl alcohol wash through celite packing. The organic layer was concentrated in vacuo and purified by silica gel chromatography (ethyl acetate:n-hexane=2:1) to afford 32a (0.15 g, 31%). m.p. 216.3-218.6. $^1$H-NMR (300 MHz, MeOD): δ 1.23-1.28 (m, 6H), 2.70 (s, 3H), 3.21 (qui, J=6.9 Hz, 1H), 6.45 (d, J=1.5 Hz, 1H), 7.54-7.62 (m, 1H), 7.71-7.79 (m, 1H), 7.94 (d, J=9 Hz, 2H), 8.06 (d, J=8.4 Hz, 1H), 8.42-8.47 (m, 1H).

2,4-dihydroxy-5-isopropyl-N-methyl-N-(2-methylquinolin-4-yl)benzamide (32b)

A mixture of 32a (0.15 g, 0.44 mmol) in DCM (5 mL) was added tert-butyldimethylsilyl chloride (0.13 g, 0.89 mmol) and DIPEA (0.12 g, 0.89 mmol). The mixture was stirred at room temperature for 6 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford product. Then this product was dissolved in tetrahydrofuran (5 ml) and added potassium tert-butoxide (0.04 g, 0.36 mmol) and methyl iodide (0.77 ml) to the reaction solution and stirred at room temperature for 5 hours. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford product. Then this product was dissolved in DCM (3 ml) and added tetra-n-butylammonium fluoride (0.09 ml). The reaction solution was stirred at room temperature for 3 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford 32b (0.02 g, 27%). $^1$H-NMR (300 MHz, MeOD): δ 1.25 (d, J=6.9 Hz, 7H), 2.67 (s, 3H), 3.22-3.26 (m, 1H), 4.13 (s, 3H), 6.60 (s, 1H), 7.58-7.63 (m, 1H), 7.71-7.76 (m, 1H), 7.87-7.92 (m, 2H), 8.01 (s, 1H), 8.40 (s, 1H).

N-ethyl-2,4-dihydroxy-5-isopropyl-N-(2-methylquinolin-4-yl)benzamide (32c)

A mixture of 32a (0.15 g, 0.44 mmol) in DCM (5 mL) was added tert-butyldimethylsilyl chloride (0.13 g, 0.89 mmol) and DIPEA (0.12 g, 0.89 mmol). The mixture was stirred at room temperature for 6 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford product. Then this product was dissolved in tetrahydrofuran (5 ml) and added potassium tert-butoxide (0.02 g, 0.17 mmol) and ethyl iodide (0.77 ml) to the reaction solution and stirred at room temperature for 6 hours. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford product. Then this product was dissolved in DCM (3 ml) and added tetra-n-butylammonium fluoride (0.09 ml). The reaction solution was stirred at room temperature for 3 hr. The reaction was quenched with water and extracted with DCM (30 ml*3). The organic layer was collected and dried over anhydrous MgSO$_4$ concentrated in vacuo and purified by silica gel chromatography (ethyl acetate:n-hexane=1:1) to afford 32c (0.02 g, 20%). $^1$H-NMR (300 MHz, MeOD): δ 1.25 (d, J=7.2 Hz, 6H), 1.62 (t, J=7.2 Hz, 3H), 2.71 (s, 3H), 3.19-3.28 (m, 1H), 4.38 (q, J=7.2 Hz, 2H), 6.62 (s, 1H), 7.59-7.67 (m, 1H), 7.75-7.83 (m, 1H), 7.94-8.09 (m, 3H), 8.45 (s, 1H).

1-(6-amino-3,4-dihydroquinolin-1(2H)-yl)ethanone (119)

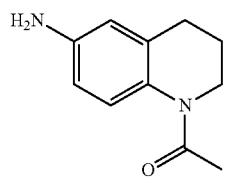

2,4-bis(benzyloxy)-5-isopropyl-N-(1,2,3,4-tetrahydroquinolin-6-yl)benzamide (120)

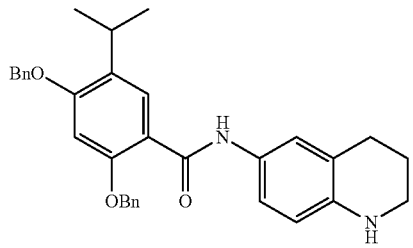 [SMILES: CC(C)c1cc(C(=O)Nc2ccc3c(c2)CCCN3)c(OCc2ccccc2)cc1OCc1ccccc1]

2,4-bis(benzyloxy)-5-isopropyl-N-methyl-N-(1,2,3,4-tetrahydroquinolin-6-yl)benzamide (121)

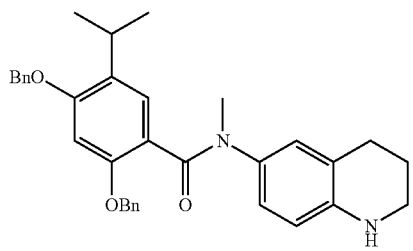 [SMILES: CC(C)c1cc(C(=O)N(C)c2ccc3c(c2)CCCN3)c(OCc2ccccc2)cc1OCc1ccccc1]

2,4-dihydroxy-5-isopropyl-N-methyl-N-(1,2,3,4-tetrahydroquinolin-6-yl)benzamide (33a)

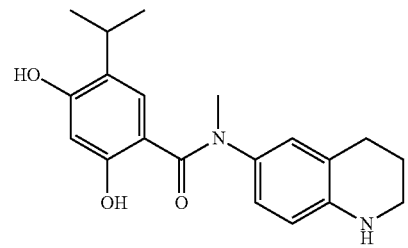 [SMILES: CC(C)c1cc(C(=O)N(C)c2ccc3c(c2)CCCN3)c(O)cc1O]

N-ethyl-2,4-dihydroxy-5-isopropyl-N-(1,2,3,4-tetrahydroquinolin-6-yl)benzamide (33b)

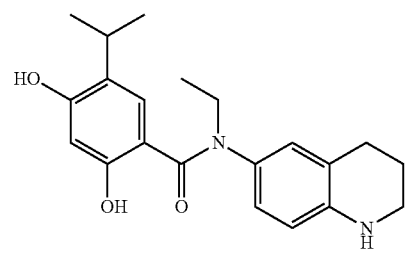 [SMILES: CCN(C(=O)c1cc(C(C)C)c(O)cc1O)c1ccc2c(c1)CCCN2]

2,4-dihydroxy-5-isopropyl-N-methyl-N-(1-methyl-1,
2,3,4-tetrahydroquinolin-6-yl)benzamide (33c)

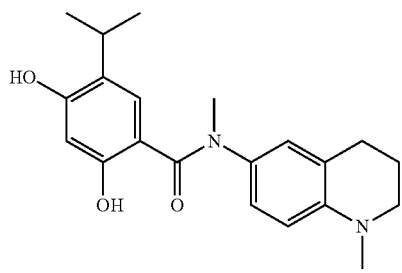 [SMILES: CC(C)c1cc(C(=O)N(C)c2ccc3c(c2)CCCN3C)c(O)cc1O]

N-ethyl-2,4-dihydroxy-5-isopropyl-N-(1-methyl-1,2,
3,4-tetrahydroquinolin-6-yl)benzamide (33d)

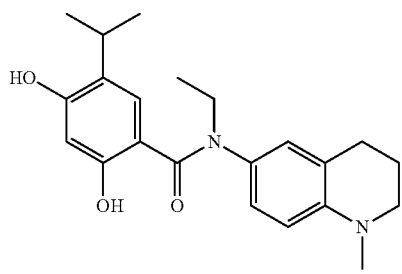 [SMILES: CCN(C(=O)c1cc(C(C)C)c(O)cc1O)c1ccc2c(c1)CCCN2C]

2,4-bis(benzyloxy)-5-isopropyl-N-(2-methylpyridin-
3-yl)benzamide (124)

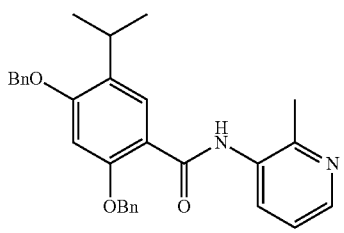 [SMILES: Cc1ncccc1NC(=O)c1cc(C(C)C)c(OCc2ccccc2)cc1OCc1ccccc1]

2,4-bis(benzyloxy)-N-(2-(benzyloxy)pyridin-3-yl)-5-
isopropylbenzamide (125)

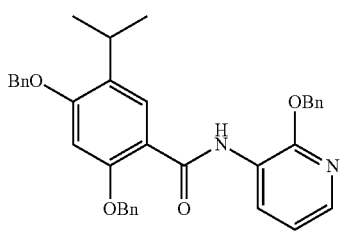 [SMILES: CC(C)c1cc(C(=O)Nc2cccnc2OCc2ccccc2)c(OCc2ccccc2)cc1OCc1ccccc1]

N-ethyl-2,4-dihydroxy-5-isopropyl-N-(2-methylpyri-
din-3-yl)benzamide (34a)

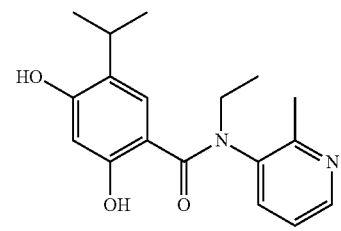 [SMILES: CCN(C(=O)c1cc(C(C)C)c(O)cc1O)c1cccnc1C]

N-(2-(benzyloxy)pyridin-3-yl)-N-ethyl-2,4-dihy-
droxy-5-isopropylbenzamide (34b)

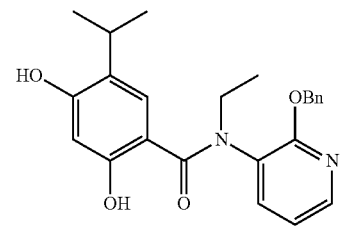 [SMILES: CCN(C(=O)c1cc(C(C)C)c(O)cc1O)c1cccnc1OCc1ccccc1]

N-(benzo[d]isoxazol-5-yl)-2,4-bis(benzyloxy)-5-
isopropylbenzamide (127)

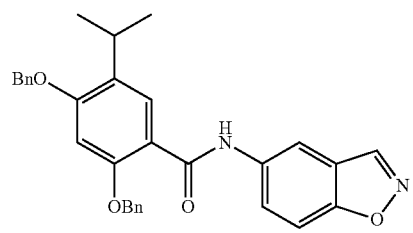 [SMILES: CC(C)c1cc(C(=O)Nc2ccc3oncc3c2)c(OCc2ccccc2)cc1OCc1ccccc1]

N-(benzo[d]isoxazol-5-yl)-2,4-dihydroxy-5-isopro-
pyl-N-methylbenzamide (35a)

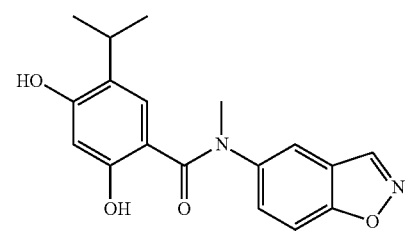 [SMILES: CC(C)c1cc(C(=O)N(C)c2ccc3oncc3c2)c(O)cc1O]

N-(benzo[d]isoxazol-5-yl)-N-ethyl-2,4-dihydroxy-5-isopropylbenzamide (35b)

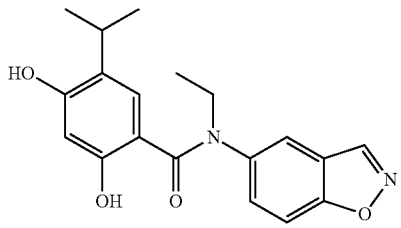 [SMILES: CCN(C(=O)c1cc(C(C)C)c(O)cc1O)c1ccc2oncc2c1]

((((4-isopropyl-6-nitro-1,3-phenylene)bis(oxy))bis(methylene))dibenzene (128)

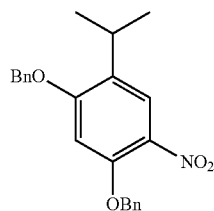 [SMILES: CC(C)c1cc([N+](=O)[O-])c(OCc2ccccc2)cc1OCc1ccccc1]

A mixture of 45 (3.00 g, 9.04 mmol), nitric acid (20 ml) and acetic acid (50 ml) was stirred for 10 min at room temperature. The reaction was quenched with water and extracted with $CH_2Cl_2$ (30 ml*3). The organic layer was collected and dried over anhydrous $MgSO_4$ concentrated in vacuo to yield colorless oil product. The residue was purified by silica gel chromatography (ethyl acetate:n-hexane=1:4, Rf=0.4) to afford 128 (1.83 g, 53.67%) as a yellow solid. $^1$H-NMR (500 MHz, $CDCl_3$): δ 1.22 (d, J=7 Hz, 6H), 3.28 (Sep, J=7 Hz, 1H), 5.07 (s, 2H), 5.16 (s, 2H), 6.54 (s, 1H), 7.39 (m, 10H), 7.89 (s, 1H).

2,4-bis(benzyloxy)-5-isopropylaniline (129)

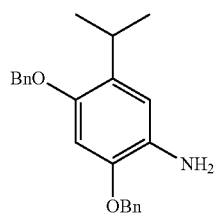

A mixture of 128 (1 g, 2.65 mmol), Fe powder (0.8 g, 14.33 mmol), $NH_4Cl$ (0.6 g, 11.11 mmol), IPA (20 ml) and $H_2O$ (5 ml), was stirred and reflux for 1.5 h. The Fe powder was removed by ethyl acetate wash through celite packing. The organic layer was concentrated in vacuo and purified by silica gel chromatography (ethyl acetate:n-hexane=1:2, Rf=0.3) to afford 129 (0.67 g, 72.83%) as a block solid. $^1$H-NMR (500 MHz, $CDCl_3$): δ 1.18 (d, J=7 Hz, 6H), 3.31 (Sep, J=7 Hz, 1H), 4.34 (s, 2H), 4.96 (s, 2H), 5.02 (s, 2H), 6.56 (s, 1H), 6.66 (s, 1H), 7.36 (m, 10H).

N-(2,4-bis(benzyloxy)-5-isopropylphenyl)-3-fluorobenzamide (130)

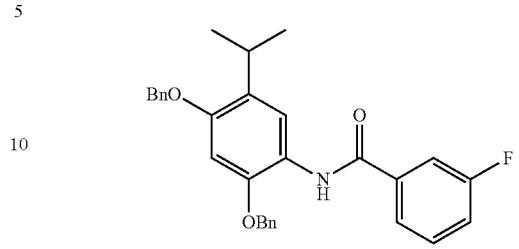

A mixture of 129 (1 g, 7.14 mmol), EDC.HCl (2 g, 10.47 mmol), HOBt (1.20 g, 8.89 mmol), NMM (2 ml, 18.98 mmol) and DMF (10 ml) was stirred for 10 min then added 3-fluorobenzoic acid (2 g, 5.76 mmol) for overnight, the reaction was quenched with water and extracted with ethyl acetate (30 ml*3). The organic layer was collected and dried over anhydrous $MgSO_4$ concentrated in vacuo to yield colorless oil product. The residue was purified by silica gel chromatography (ethyl acetate:n-hexane=1:2, Rf=0.6) to afford 130 (1.73 g, 64.07%) as a block solid. $^1$H-NMR (500 MHz, $CDCl_3$): δ 1.30 (d, J=7 Hz, 6H), 3.42 (Sep, J=7 Hz, 1H), 5.05 (s, 2H), 5.11 (s, 2H), 6.64 (s, 1H), 7.36 (m, 14H), 8.39 (s, 1H), 8.43 (s, 1H).

N-(2,4-bis(benzyloxy)-5-isopropylphenyl)-4-fluorobenzamide (131)

A mixture of 129 (1 g, 7.14 mmol), EDC.HCl (2 g, 10.47 mmol), HOBt (1.20 g, 8.89 mmol), NMM (2 ml, 18.98 mmol) and DMF (10 ml) was stirred for 10 min then added 4-fluorobenzoic acid (2 g, 5.76 mmol) for overnight, the reaction was quenched with water and extracted with ethyl acetate (30 ml*3). The organic layer was collected and dried over anhydrous $MgSO_4$ concentrated in vacuo to yield colorless oil product. The residue was purified by silica gel chromatography (ethyl acetate:n-hexane=1:4, Rf=0.7) to afford 131 (1.64 g, 60.74%) as a block solid. $^1$H-NMR (500 MHz, $CDCl_3$): 51.25 (d, J=7 Hz, 6H), 3.38 (Sep, J=7 Hz, 1H), 5.03 (s, 2H), 5.08 (s, 2H), 6.61 (s, 1H), 7.09 (m, 2H), 7.36 (m, 10H), 7.78 (m, 2H), 8.30 (s, 1H), 8.40 (s, 1H).

N-(2,4-dihydroxy-5-isopropylphenyl)-3-fluorobenzamide (36a)

A mixture of 130 (0.35 g, 0.75 mmol), 10% palladium on activated carbon (0.04 g, 0.04 mmol) and MeOH (8 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.4) to afford 36a (0.19 g, 86.36%) as a brown oil. $^1$H-NMR (500 MHz, MeOD): δ 1.19 (d, J=7 Hz, 6H), 3.19 (Sep, J=7 Hz, 1H), 6.41 (s, 1H), 7.28 (m, 1H), 7.67 (qui, J=7.5 Hz, 1H), 7.75 (d, J=7.5 Hz, 1H).

N-(2,4-dihydroxy-5-isopropylphenyl)-3-fluoro-N-methylbenzamide (36b)

A mixture of 130 (0.37 g, 0.79 mmol), NaH (0.04 g, 1 mmole) and DMF (4 ml) was added methyl iodide (0.1 ml, 1.61 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.5) to get the oily product, then the oily product was dissolved in MeOH (8 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.2) to afford 36b (0.15 g, 62.50%) as a brown oil. ¹H-NMR (500 MHz, MeOD): δ 0.90 (d, J=7 Hz, 3H), 1.05 (d, J=7 Hz, 3H), 3.00 (Sep, J=7 Hz, 1H), 3.29 (s, 3H), 6.24 (s, 1H), 6.61 (s, 1H), 6.94 (m, 1H), 7.00 (m, 1H), 7.08 (d, J=7.5 Hz, 1H), 7.16 (m, 1H).

N-(2,4-dihydroxy-5-isopropylphenyl)-N-ethyl-3-fluorobenzamide (36c)

A mixture of 130 (0.33 g, 0.70 mmol), NaH (0.04 g, 1 mmole) and DMF (4 ml) was added ethyl iodide (0.1 ml, 1.24 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.5) to get the oily product, then the oily product was dissolved in MeOH (7 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 36c (0.13 g, 59.09%) as a pink solid. m.p. 183.8-184.1. ¹H-NMR (500 MHz, MeOD): δ 0.92 (d, J=7 Hz, 3H), 1.06 (d, J=7 Hz, 3H), 1.17 (t, J=7 Hz, 3H), 3.01 (Sep, J=7 Hz, 1H), 3.58 (Sex, J=7 Hz, 1H), 4.01 (Sex, J=7 Hz, 1H), 6.23 (s, 1H), 6.57 (s, 1H), 6.93 (m, 1H), 6.98 (m, 1H), 7.01 (m, 1H), 7.15 (m, 1H).

N-(2,4-dihydroxy-5-isopropylphenyl)-3-fluoro-N-propylbenzamide (36d)

A mixture of 130 (0.34 g, 0.72 mmol), NaH (0.04 g, 1 mmole) and DMF (4 ml) was added 1-iodopropane (0.1 ml, 1.03 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.5) to get the oily product, then the oily product was dissolved in MeOH (9 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 36d (0.14 g, 58.33%) as a pink solid. m.p. 185.1-186.4. ¹H-NMR (500 MHz, MeOD): δ 0.92 (d, 6H), 1.06 (d, J=7 Hz, 3H), 1.61 (m, 2H), 3.01 (qui, J=7 Hz, 1H), 3.97 (m, 1H), 6.23 (s, 1H), 6.57 (s, 1H), 6.93 (m, 1H), 7.01 (m, 1H), 7.08 (m, 1H), 7.16 (m, 1H).

N-(2,4-dihydroxy-5-isopropylphenyl)-3-fluoro-N-isopropylbenzamide (36e)

A mixture of 130 (0.34 g, 0.72 mmol), NaH (0.04 g, 1 mmole) and DMF (4 ml) was added 2-iodopropane (0.1 ml, 1.03 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.5) to get the oily product, then the oily product was dissolved in MeOH (7 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 36e (0.13 g, 54.17%) as a pink solid. m.p. 226.4-228.9. ¹H-NMR (500 MHz, MeOD): δ 1.02 (d, J=7 Hz, 3H), 1.12 (t, J=7 Hz, 6H), 1.25 (d, J=7 Hz, 3H), 3.05 (Sep, J=7 Hz, 1H), 4.81 (m, 1H), 6.15 (s, 1H), 6.67 (s, 1H), 6.89 (m, 1H), 7.00 (d, J=9.5 Hz, 1H), 7.06 (d, J=7.5 Hz, 1H), 7.12 (m, 1H).

N-(2,4-dihydroxy-5-isopropylphenyl)-4-fluorobenzamide (37a)

A mixture of 131 (0.34 g, 0.72 mmol), 10% palladium on activated carbon (0.04 g, 0.04 mmol) and MeOH (9 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 37a (0.17 g, 80.95%) as a brown oil. ¹H-NMR (500 MHz, CDCl₃): δ 1.20 (d, J=7 Hz, 6H), 3.14 (Sep, J=7 Hz, 1H), 5.35 (s, 1H), 6.47 (s, 1H), 6.87 (s, 1H), 7.17 (m, 2H), 7.92 (m, 2H), 8.04 (s, 1H), 8.73 (s, 1H).

N-(2,4-dihydroxy-5-isopropylphenyl)-4-fluoro-N-methylbenzamide (37b)

A mixture of 131 (0.37 g, 0.79 mmol), NaH (0.04 g, 1 mmole) and DMF (4 ml) was added methyl iodide (0.1 ml, 1.61 mmol) at room temperature for 2 h. The reaction was quenched with water and extracted with ethyl acetate (30 ml*3). The organic layer was collected and dried over anhydrous MgSO₄ concentrated in vacuo and purified by silica gel chromatography (ethyl acetate:n-hexane=1:2, Rf=0.6) to get the oily product, then the oily product was dissolved in MeOH (7 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 37b (0.14 g, 58.33%) as a white solid. m.p. 180.1-180.9. ¹H-NMR (500 MHz, MeOD): δ 0.90 (d, J=7 Hz, 3H), 1.04 (d, J=7 Hz, 3H), 3.00 (Sep, J=1H), 3.29 (s, 3H), 6.24 (s, 1H), 6.58 (s, 1H), 6.88 (m, 2H), 7.31 (m, 1H).

N-(2,4-dihydroxy-5-isopropylphenyl)-N-ethyl-4-fluorobenzamide (37c)

A mixture of 131 (0.32 g, 0.68 mmol), NaH (0.04 g, 1 mmole) and DMF (4 ml) was added ethyl iodide (0.1 ml, 1.24 mmol) at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.5) to get the oily product, then the oily product was dissolved in MeOH (7 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 37c (0.13 g, 59.09%) as a white solid. m.p. 209.9-211.3. $^1$H-NMR (500 MHz, MeOD): δ 0.91 (d, J=7 Hz, 3H), 1.05 (d, J=7 Hz, 3H), 1.16 (t, J=7 Hz, 3H), 3.02 (Sep, J=7 Hz, 1H), 3.58 (6, J=7 Hz, 1H), 4.00 (6, J=7 Hz, 1H), 6.24 (s, 1H), 6.54 (s, 1H), 6.86 (m, 2H), 7.31 (m, 2H).

N-(2,4-dihydroxy-5-isopropylphenyl)-4-fluoro-N-propylbenzamide (37d)

A mixture of 131 (0.36 g, 0.77 mmol), NaH (0.04 g, 1 mmole) and DMF (4 ml) was added 1-iodopropane (0.1 ml, 1.03 mmol) at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.5) to get the oily product, then the oily product was dissolved in MeOH (8 ml) and added 10% palladium on activated carbon (0.04 g, 0.04 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 37d (0.15 g, 57.69%) as a pink solid. m.p. 178.1-178.7. $^1$H-NMR (500 MHz, MeOD): δ 0.92 (m, 6H), 1.05 (d, J=7 Hz 3H), 1.59 (m, 2H), 3.00 (Sex, J=7 Hz, 1H), 4.45 (m, 1H), 3.96 (m, 1H), 6.23 (s, 1H), 6.54 (s, 1H), 6.86 (m, 2H), 7.29 (m, 2H).

N-(2,4-dihydroxy-5-isopropylphenyl)-4-methoxy-benzenesulfonamide (38a)

A mixture of 131 (0.8 g, 2.3 mmol), pyridine (2 ml) and DCM (8 ml) was added 4-methoxybenzesulfonyl chloride (0.7 g, 3.39 mmol) and stirred at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.6) to get the oily product, then the oily product was dissolved in MeOH (15 ml) and added 10% palladium on activated carbon (0.10 g, 0.09 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.2) to afford 38a (0.51 g, 65.38%) as a block solid. m.p. 127.5-129.8. $^1$H-NMR (500 MHz, CDCl$_3$): δ 0.93 (d, J=6.5 Hz, 6H), 2.96 (qui, J=6.5 Hz, 1H), 3.82 (s, 3H), 6.23 (s, 1H), 6.32 (s, 1H), 6.40 (s, 1H), 6.88 (d, J=9 Hz, 2H), 7.60 (d, J=9 Hz, 2H).

N-(2,4-dihydroxy-5-isopropylphenyl)-4-fluorobenzenesulfonamide (38b)

A mixture of 131 (0.45 g, 1.30 mmol), pyridine (2 ml) and DCM (8 ml) was added 4-fluorobenzenesulfonyl chloride (0.4 g, 2.06 mmol) and stirred at room temperature for 2 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.5) to get the oily product, then the oily product was dissolved in MeOH (7 ml) and added 10% palladium on activated carbon (0.05 g, 0.05 mmol) under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 38b (0.27 g, 64.29%) as a brown solid. m.p. 168.3-169.1. $^1$H-NMR (500 MHz, CDCl$_3$): δ 0.94 (d, J=7 Hz, 6H), 2.98 (Sep, J=7 Hz, 1H), 6.16 (s, 1H), 6.55 (s, 1H), 6.99 (m, 2H), 7.61 (m, 2H).

4-isopropyl-6-(3,4,5-trimethoxyphenethyl)benzene-1,3-diol (39a)

A mixture of 3,4,5-trimethoxybenzyl chloride (0.8 g, 3.69 mmol), triphenylphosphine (3 g, 11.44 mmol) and toluene (10 ml) was refluxed for overnight. The reaction was filtered by hexane wash and took the precipitate and directly used in next step. A mixture of 46 (1 g, 2.78 mmol), NaH (0.15 g, 3.75 mmol) and toluene (15 ml) was stirred for 10 min then added the former precipitate at room temperature for overnight. The residue was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.6) to afford as an oily product and directly used in next step. A mixture of oily product, 10% palladium on activated carbon (0.1 g, 0.09 mmol) and MeOH (6 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:2, Rf=0.3) to afford 39a (0.54 g, 56.25%) as a colorless oil. $^1$H-NMR (500 MHz, MeOD): δ 1.06 (d, J=7 Hz, 6H), 2.74 (s, 4H), 3.09 (Sep, J=7 Hz, 1H), 3.70 (s, 3H), 3.73 (s, 6H), 6.28 (s, 1H), 6.36 (s, 2H), 6.55 (s, 1H).

4-isopropyl-6-(4-methoxyphenethyl)benzene-1,3-diol (39b)

A mixture of 4-methoxybenzyl chloride (0.6 g, 3.83 mmol), triphenylphosphine (3 g, 11.44 mmol) and toluene (9 ml) was refluxed for overnight. The reaction was filtered by hexane wash and took the precipitate and directly used in next step. A mixture of 46 (1 g, 2.78 mmol), NaH (0.15 g, 3.75 mmol) and toluene (15 ml) was stirred for 10 min then added the former precipitate at room temperature for overnight. The residue was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:3, Rf=0.7) to afford as an oily product and directly used in next step. A mixture of oily product, 10% palladium on activated carbon (0.1 g, 0.09 mmol) and MeOH (7 ml)

was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:3, Rf=0.2) to afford 39b (0.43 g, 53.75%) as a brown oil. $^1$H-NMR (500 MHz, CDCl$_3$): δ 1.19 (d, J=7 Hz, 6H), 2.80 (m, 4H), 3.06 (Sep, J=7 Hz, 1H), 3.78 (s, 3H), 4.67 (s, 1H), 4.86 (s, 1H), 6.21 (s, 1H), 6.81 (m, 3H), 7.07 (d, J=8.5 Hz, 2H).

4-(4-fluorophenethyl)-6-isopropylbenzene-1,3-diol (39c)

A mixture of 4-fluorobenzyl chloride (0.5 g, 3.47 mmol), triphenylphosphine (3 g, 11.44 mmol) and toluene (9 ml) was refluxed for overnight. The reaction was filtered by hexane wash and took the precipitant and directly used in next step. A mixture of 46 (1 g, 2.78 mmol), NaH (0.15 g, 3.75 mmol) and toluene (15 ml) was stirred for 10 min then added the former precipitant at room temperature for overnight. The residue was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:3, Rf=0.6) to afford as an oily product and directly used in next step. A mixture of oily product, 10% palladium on activated carbon (0.1 g, 0.09 mmol) and MeOH (7 ml) was under the hydrogen gas. The reaction was stirred at room temperature for 2 h. The 10% palladium on activated carbon was removed by methyl alcohol wash through celite packing. The organic layer was concentrated in vacuo and purified by silica gel chromatography (ethyl acetate:n-hexane=1:3, Rf=0.3) to afford 39c (0.39 g, 51.31%) as a pink solid. m.p. 82.6-83.3. $^1$H-NMR (500 MHz, CDCl$_3$): δ 1.17 (d, J=6.5 Hz, 6H), 2.81 (m, 4H), 3.04 (qui, J=7 Hz, 1H), 4.60 (s, 1H), 4.72 (s, 1H), 6.23 (s, 1H), 6.74 (s, 1H), 6.93 (m, 2H), 7.09 (m, 2H).

1-(2,4-dihydroxy-5-isopropylphenyl)ethanone (139)

A mixture of 45 (3.00 g, 9.04 mmol), 10% palladium on activated carbon (0.4 g, 0.38 mmol) and MeOH (15 ml) was under the hydrogen gas and 40 psi at room temperature for overnight. The 10% palladium on activated carbon was removed by methyl alcohol wash through celite packing. The organic layer was concentrated in vacuo and purified by silica gel chromatography (ethyl acetate:n-hexane=1:4, Rf=0.5) to afford as an oily product, and directly used in next step. A mixture of the oily product, ZnCl$_2$ (2.00 g, 20 mmol) and acetic acid (8 ml) was refluxed for overnight. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:4, Rf=0.3) to afford 139 (1.02 g, 58.29%) as an oily product. $^1$H-NMR (500 MHz, CDCl$_3$): δ 1.25 (d, J=6.5 Hz, 6H), 2.57 (s, 3H), 3.13 (Sep, J=7 Hz, 1H), 5.57 (s, 1H), 6.30 (s, 1H), 7.26 (s, 1H), 7.49 (s, 1H), 12.53 (s, 1H).

1-(5-isopropyl-2,4-bis((4-methoxybenzyl)oxy)phenyl)ethanone (140)

A mixture of 139 (1.02 g, 5.25 mmol), Cs$_2$CO$_3$ (5 g, 15.35 mmol), KI (cat.) and DMF (8 ml) was added 4-methoxybenzyl chloride (2 ml, 14.75 mmol) at room temperature for overnight. The reaction was quenched with 6N NaOH (aq.) and extracted with ethyl acetate (30 ml*3). The organic layer was collected and dried over anhydrous MgSO$_4$ concentrated in vacuo to and purified by silica gel chromatography (ethyl acetate:n-hexane=1:3, Rf=0.4) to afford 140 (1.51 g, 66.23%) as a yellow solid. $^1$H-NMR (500 MHz, CDCl$_3$): δ 1.20 (d, J=6.5 Hz, 6H), 2.53 (s, 3H), 3.24 (qui, J=7 Hz, 1H), 3.82 (s, 6H), 5.03 (s, 2H), 5.04 (s, 2H), 6.53 (s, 1H), 6.92 (m, 4H), 7.32 (m, 4H), 7.74 (s, 1H).

(E)-3-(3,4-dimethoxyphenyl)-1-(5-isopropyl-2,4-bis((4-methoxybenzyl)oxy)phenyl)prop-2-en-1-one (143)

A mixture of 140 (1.00 g, 2.30 mmol),1N NaOH (5 ml), MeOH (8 ml) and DCM (3 ml) was stirred for 10 min then added 3,4-dimethoxybenzaldehyde (0.6 g, 3.61 mmol) at room temperature for overnight. The reaction was quenched with water and extracted with CH$_2$Cl$_2$ (30 ml*3). The organic layer was collected and dried over anhydrous MgSO$_4$ concentrated in vacuo to yield colorless oil product. The residue was purified by silica gel chromatography (ethyl acetate:n-hexane=1:2, Rf=0.2) to afford 143 (0.68 g, 50.75%) as a yellow solid. $^1$H-NMR (500 MHz, MeOD): δ 1.22 (d, J=6.5 Hz, 6H), 3.28 (Sep, J=7 Hz, 1H), 3.72 (d, J=4.5 Hz, 6H), 3.79 (s, 3H), 3.87 (s, 3H), 5.02 (s, 2H), 5.06 (s, 2H), 6.76 (m, 3H), 6.90 (m, 4H), 7.33 (m, 4H), 7.52 (d, J=16 Hz, 1H), 7.51 (d, J=16 Hz, 1H), 7.77 (s, 1H).

(E)-3-(2,5-dimethoxyphenyl)-1-(5-isopropyl-2,4-bis((4-methoxybenzyl)oxy)phenyl)prop-2-en-1-one (144)

A mixture of 140 (1.00 g, 2.30 mmol), 1N NaOH (6 ml), MeOH (9 ml) and DCM (3 ml) was stirred for 10 min then added 2,5-dimethoxybenzaldehyde (0.6 g, 3.61 mmol) at room temperature for overnight. The reaction was quenched with water and extracted with CH$_2$Cl$_2$ (30 ml*3). The organic layer was collected and dried over anhydrous MgSO$_4$ concentrated in vacuo to yield colorless oil product. The residue was purified by silica gel chromatography (ethyl acetate:n-hexane=1:3, Rf=0.2) to afford 144 (0.70 g, 52.24%) as a yellow solid. $^1$H-NMR (500 MHz, CDCl$_3$): δ 1.25 (d, J=6.5 Hz, 6H), 3.31 (Sep, J=7 Hz, 1H), 3.66 (s, 3H), 3.74 (d, J=7 Hz, 6H), 3.80 (s, 3H), 5.05 (s, 2H), 5.06 (s, 2H), 6.61 (s, 1H), 6.80 (m, 3H), 6.87 (m, 1H), 6.95 (m, 3H), 7.33 (m, 4H), 7.66 (d, J=16 Hz, 1H), 7.76 (s, 1H), 8.04 (d, J=16 Hz, 1H).

(E)-1-(2,4-dihydroxy-5-isopropylphenyl)-3-(3,4-dimethoxyphenyl)prop-2-en-1-one (40a)

A mixture of 143 (0.6 g, 1.03 mmol) and DCM (20 ml) was added titanium (IV) chloride (0.3 ml, 2.73 mmol) at 0° C. for 1 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:3, Rf=0.3) to afford 40a (0.19 g, 54.29%) as an yellow solid. m.p. 177.2-178.1. $^1$H-NMR (500 MHz, MeOD): δ 1.27 (d, J=7.5 Hz, 6H), 3.20 (Sep, J=7 Hz, 1H), 3.88 (s, 2H), 3.91 (s, 2H), 6.29 (s, 1H), 7.00 (d, J=8.5 Hz, 1H), 7.32 (m, 1H), 7.37 (d, J=2 Hz, 1H), 7.64 (d, J=15 Hz, 1H), 7.79 (m, 2H).

(E)-1-(2,4-dihydroxy-5-isopropylphenyl)-3-(2,5-dimethoxyphenyl)prop-2-en-1-one (40b)

A mixture of 144 (0.72 g, 1.24 mmol) and DCM (25 ml) was added titanium(IV) chloride (0.3 ml, 2.73 mmol) at 0°

C. for 1 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:2, Rf=0.4) to afford 40b (0.2 g, 47.62%) as an orange solid. m.p. 140.3-142.1. $^1$H-NMR (500 MHz, CDCl$_3$): δ 1.28 (d, J=6.5 Hz, 6H), 3.17 (Sep, J=7 Hz, 1H), 3.83 (s, 3H), 3.88 (s, 3H), 6.12 (s, 1H), 6.37 (s, 1H), 6.88 (d, J=9 Hz, 1H), 6.95 (m, 1H), 7.16 (d, J=3 Hz, 1H), 7.69 (m, 2H), 8.10 (d, J=16 Hz, 1H), 13.29 (s, 1H).

2,4-dihydroxy-5-isopropylbenzaldehyde (145)

A mixture of 45 (3.00 g, 9.04 mmol), 10% palladium on activated carbon (0.4 g, 0.38 mmol) and MeOH (15 ml) was under the hydrogen gas and 40 psi at room temperature for overnight. The 10% palladium on activated carbon was removed by methyl alcohol wash through celite packing. The organic layer was concentrated in vacuo and purified by silica gel chromatography (ethyl acetate:n-hexane=1:4, Rf=0.2) to afford as an oily product, and directly used in next step. A mixture of POCl$_3$ (4 ml, 42.91 mmol) and DMF (3.5 ml, 45.40 mmol) was stirred at 0° C. for 10 min then added the oily product dissolved in DMF (4 ml). The reaction was stirred at room temperature for overnight. The reaction was quenched with 6N NaOH (aq.) and extracted with ethyl acetate (30 ml*3). The organic layer was collected and dried over anhydrous MgSO$_4$ concentrated in vacuo to yield a yellow product. The residue was without more purification to afford 145 (0.91 g, 55.82%) as a yellow solid. $^1$H-NMR (500 MHz, MeOD): δ 1.20 (d, J=6.5 Hz, 6H), 3.16 (Sex, J=7 Hz, 1H), 6.27 (s, 1H), 7.38 (s, 1H), 9.68 (s, 1H).

5-isopropyl-2,4-bis((4-methoxybenzyl)oxy)benzaldehyde (146)

A mixture of 145 (1 g, 5.56 mmol), K$_2$CO$_3$ (2 g, 14.47 mmol), KI (cat.) and DMF (8 ml) was added 4-methoxybenzyl chloride (2 ml, 14.75 mmol) at room temperature for overnight. The reaction was quenched with 6N NaOH (aq.) and extracted with ethyl acetate (30 ml*3). The organic layer was collected and dried over anhydrous MgSO$_4$ concentrated in vacuo and purified by silica gel chromatography (ethyl acetate:n-hexane=1:4, Rf=0.4) to afford 146 (1.49 g, 63.67%) as a yellow solid. $^1$H-NMR (500 MHz, CDCl$_3$): δ 1.19 (d, J=7 Hz, 6H), 3.23 (Sex, J=7 Hz, 1H), 3.82 (s, 3H), 3.83 (s, 3H), 5.04 (s, 2H), 5.06 (s, 2H), 6.53 (s, 1H), 6.92 (m, 4H), 7.31 (d, J=8.5 Hz, 4H), 7.72 (s, 1H), 10.35 (s, 1H).

(E)-3-(2,4-bis(benzyloxy)-5-isopropylphenyl)-1-(3,4,5-trimethoxyphenyl)prop-2-en-1-one (148)

A mixture of 1-(3,4,5-trimethoxyphenyl)ethanone (0.6 g, 2.86 mmol), 1N NaOH (5 ml) and MeOH (10 ml) was stirred for 10 min then added 146 (0.8 g 1.90 mmol) at room temperature for overnight. The reaction was quenched with water and extracted with CH$_2$Cl$_2$ (30 ml*3). The organic layer was collected and dried over anhydrous MgSO$_4$ concentrated in vacuo to yield colorless oil product. The residue was purified by silica gel chromatography (ethyl acetate:n-hexane=1:4, Rf=0.2) to afford 148 (0.50 g, 43.10%) as a orange solid. $^1$H-NMR (500 MHz, CDCl$_3$): δ 1.22 (d, J=7 Hz, 6H), 3.28 (hept, J=7 Hz, 1H), 3.79 (d, J=2 Hz, 9H), 3.81 (s, 3H), 3.90 (s, 3H), 5.02 (s, 2H), 5.04 (s, 2H), 6.59 (s, 1H), 6.90 (m, 4H), 7.17 (s, 2H), 7.33 (m, 4H), 7.43 (s, 1H), 7.53 (d, J=15.5 Hz, 1H), 8.02 (d, J=15.5 Hz, 1H).

(E)-3-(2,4-dihydroxy-5-isopropylphenyl)-1-(3,4,5-trimethoxyphenyl)prop-2-en-1-one (41)

A mixture of 148 (0.66 g, 1.07 mmol) and DCM (25 ml) was added titanium(IV) chloride (0.3 ml, 2.73 mmol) at 0° C. for 1 h. The reaction was quenched with water and extracted with ethyl acetate (30 ml*3). The organic layer was collected and dried over anhydrous MgSO$_4$ concentrated in vacuo and purified by silica gel chromatography (ethyl acetate:n-hexane=1:1, Rf=0.3) to afford 41 (0.19 g, 47.50%) as an red solid. m.p. 114.8-115.9. $^1$H-NMR (500 MHz, CDCl$_3$): δ 1.19 (d, J=7 Hz, 6H), 3.13 (Sep, J=7 Hz, 1H), 3.88 (d, J=2.5 Hz, 9H), 6.32 (s, 1H), 7.22 (s, 2H), 7.30 (s, 1H), 7.44 (d, J=15.5 Hz, 1H), 8.03 (d, J=15.5 Hz, 1H).

Compound G-9

$^1$H NMR (300 MHz, CD$_3$OD): δ 1.25 (d, J=6.9 Hz, 6H), 1.39-1.42 (m, 4H), 1.62-1.72 (m, 4H), 2.12 (t, J=7.5 Hz, 2H), 2.38 (t, J=7.5 Hz, 2H), 3.16-3.26 (m, 1H), 6.35 (s, 1H), 7.53-7.60 (m, 4H), 7.75 (s, 1H). LRMS m/z: calculated 480.49 found 480.2 (M+Na).

Compound G-10

$^1$H NMR (300 MHz, CD$_3$OD): δ 0.82 (d, J=6.6 Hz, 6H), 1.30-1.38 (m, 4H), 1.63-1.69 (m, 4H), 2.10 (t, J=7.2 Hz, 2H), 2.36 (t, J=7.2 Hz, 2H), 2.88-2.97 (m, 1H), 3.82 (s, 3H), 6.19 (s, 1H), 6.61 (s, 1H), 7.12 (d, J=8.4 Hz, 2H), 7.56 (d, J=8.7 Hz, 1H). LRMS m/z: calculated 494.52 found 494.2 (M+Na).

Compound G-11

$^1$H NMR (300 MHz, CD$_3$OD): δ 0.82 (d, J=6.9 Hz, 6H), 1.20 (t, J=6.3 Hz, 3H), 1.38-1.39 (m, 4H), 1.62-1.70 (m, 4H), 2.10 (t, J=6.9 Hz, 2H), 2.37 (t, J=7.2 Hz, 2H), 2.90-2.97 (m, 1H), 3.89-3.96 (m, 2H), 6.19 (s, 1H), 6.60 (s, 1H), 7.11 (d, J=8.7 Hz, 2H), 7.57 (d, J=8.7 Hz, 1H). LRMS m/z: calculated 508.55 found 508.2 (M+Na).

Compound G-12

$^1$H NMR (300 MHz, CD$_3$OD): δ 0.85 (d, J=6.9 Hz, 6H), 1.18 (d, J=6.9 Hz, 6H), 1.36 (m, 4H), 1.61-1.63 (m, 4H), 2.00-2.10 (m, 3H), 2.34 (t, J=7.2 Hz, 2H), 2.85-2.98 (m, 1H), 4.93-4.97 (m, 1H), 6.13 (s, 1H), 6.58 (s, 1H), 7.07 (d, J=8.7 Hz, 2H), 7.52 (d, J=8.7 Hz, 1H).

Compound G-13

$^1$H NMR (300 MHz, DMSO): δ 1.18 (d, J=6.9 Hz, 6H), 1.22-1.28 (m, 4H), 1.44-1.59 (m, 4H), 1.93 (t, J=7.5 Hz, 2H), 2.29 (t, J=7.5 Hz, 2H), 3.06-3.24 (m, 1H), 6.36 (s, 1H), 7.21-7.35 (m, 4H), 7.76 (s, 1H), 7.95 (s, 1H), 8.65 (s, 1H), 9.90 (s, 1H), 10.14 (d, J=8.4 Hz, 2H), 10.33 (s, 1H). LRMS m/z: calculated 480.49 found 480.1 (M+Na).

Compound G-14

$^1$H NMR (300 MHz, DMSO): δ 0.77 (d, J=6.9 Hz, 6H), 1.23 (bs, 8H), 1.42-1.53 (m, 4H), 1.90-1.95 (m, 2H), 2.24 (t, J=7.5 Hz, 2H), 2.79-2.86 (m, 1H), 3.29 (s, 3H), 6.19 (s, 1H), 6.60 (s, 1H), 6.86 (d, J=7.8 Hz, 2H), 7.23 (t, J=8.1 Hz, 1H), 7.41 (d, J=8.1 Hz, 1H), 7.50 (s, 1H), 8.64 (s, 1H), 9.72 (s, 1H), 9.78 (s, 1H), 10.31 (s, 1H), 10.70 (s, 1H). LRMS m/z: calculated 494.52 found 494.2 (M+Na).

Compound G-15

$^1$H NMR (300 MHz, DMSO): δ 0.75 (d, J=6.9 Hz, 6H), 1.09 (t, J=7.2 Hz, 3H), 1.23 (bs, 9H), 1.42-1.53 (m, 4H), 1.90-1.96 (m, 2H), 2.24 (t, J=7.2 Hz, 2H), 2.78-2.85 (m, 1H), 3.74-3.80 (m, 2H), 6.18 (s, 1H), 6.57 (s, 1H), 6.83 (d, J=9.0 Hz, 2H), 7.24 (t, J=8.1 Hz, 1H), 7.43-7.48 (m, 2H), 8.64 (s, 1H), 9.72 (s, 1H), 9.90 (s, 1H), 10.31 (s, 1H), 10.83 (s, 1H). LRMS m/z: calculated 508.55 found 508.2 (M+Na).

Compound G-16

$^1$H NMR (300 MHz, CD$_3$OD): δ 1.25 (d, J=6.9 Hz, 7H), 1.29-1.34 (m, 4H), 1.49-1.58 (m, 2H), 1.65-1.72 (m, 2H) 2.02-2.04 (m, 2H), 2.44 (t, J=7.5 Hz, 2H), 3.17-3.26 (m, 1H), 6.37 (s, 1H), 7.19-7.32 (m, 3H), 7.68 (s, 1H), 7.81 (d, J=7.8 Hz, 7H). LRMS m/z: calculated 480.49 found 480.2 (M+Na).

Compound G-17

$^1$H NMR (300 MHz, CD$_3$OD): δ 0.82 (d, J=6.9 Hz, 6H), 1.36-1.44 (m, 2H), 1.61-1.75 (m, 4H), 2.11 (t, J=7.2 Hz, 2H), 2.36 (t, J=7.5 Hz, 2H), 2.88-2.97 (m, 1H), 3.40 (s, 3H), 6.20 (s, 1H), 6.61 (s, 1H), 7.11 (d, J=9 Hz, 2H), 7.55 (d, J=8.7 Hz, 1H). (sample didnt send for mass yet)

Compound G-18

$^1$H NMR (300 MHz, CD$_3$OD): δ 0.76 (d, J=6.9 Hz, 6H), 1.25-1.32 (m, 6H), 1.54-1.65 (m, 4H), 2.04 (t, J=7.5 Hz, 2H), 2.30 (t, J=7.5 Hz, 2H), 2.83-2.92 (m, 1H), 3.36 (s, 3H), 6.15 (s, 1H), 6.56 (s, 1H), 7.07 (d, J=8.7 Hz, 2H), 7.51 (d, J=8.7 Hz, 1H).

Example 2: In Vitro Inhibition of HSP90 with Compounds of Formula (I)

Certain compounds of formula (I) prepared in Example 1 were evaluated using the above-described SRB assay.

Shown in Table 1 below are antiproliferative activities of compounds of formula (I) in inhibiting proliferation of lung A549, colorectal HCT116, liver Hep3B, breast MDA-MB-231, prostate PC3, oral KB, and HUVEC cells.

TABLE 1

In vitro activity against human cancer cell lines and HUVEC cell, GI$_{50}$ (μM)

| Compd. No. | Lung A549 | Colorectal HCT116 | Liver Hep3B | Breast MDA-MB-231 | Prostate PC3 | Oral KB | HUVEC |
|---|---|---|---|---|---|---|---|
| 18a | | | | | | >50 | |
| 18b | 0.07 ± 0.01 | 0.09 ± 0.01 | 0.20 ± 0.03 | 0.09 ± 0.01 | | 0.05 ± 0.02 | 0.87 ± 0.01 |
| 18c | | | | | | 0.51 ± 0.17 | |
| 18d | | | | | | 0.28 ± 0.00 | |
| 19a | | | | | | >50 | |
| 19b | 0.12 ± 0.01 | 0.64 ± 0.41 | 0.10 ± 0.01 | 0.08 ± 0.01 | | 0.04 ± 0.01 | <0.1 |
| 19c | | | | | | 0.42 ± 0.08 | |
| 19d | | | | | | 0.25 ± 0.05 | |
| 20a | | | | | | 23.83 ± 5.19 | |
| 20b | 0.17 ± 0.01 | 1.00 ± 0.49 | 0.18 ± 0.04 | 0.07 ± 0.01 | | 0.024 ± 0.004 | 0.57 ± 0.02 |
| 20c | 0.11 ± 0.01 | 0.37 ± 0.05 | 0.11 ± 0.02 | 0.08 ± 0.01 | | 0.032 ± 0.004 | <0.1 |
| 20d | | | | | | 0.330 ± 0.010 | |
| 20e | | | | | | 0.165 ± 0.007 | |
| 20f | | | | | | 30.24 ± 3.87 | |
| 20g | 0.28 ± 0.02 | 0.70 ± 0.06 | 0.57 ± 0.32 | 0.10 ± 0.02 | | 0.049 ± 0.018 | 0.82 ± 0.03 |
| 20h | | | | | | 0.076 ± 0.006 | |
| 20i | | | | | | 0.400 ± 0.000 | |
| 21a | 0.30 ± 0.03 | | | | | | |
| 21b | >10 | | | | | | |
| 21c | 0.10 ± 0.02 | | | | | | |
| 21d | 0.09 ± 0.01 | | | | | | |
| 21e | 1.62 ± 0.12 | | | | | | |
| 21f | 0.84 ± 0.04 | | | | | | |
| 22a | >10 | | | | | | |
| 22b | >10 | | | | | | |
| 22c | >10 | | | | | | |
| 22d | >10 | | | | | | |
| 22e | >10 | | | | | | |
| 23a | | | | | | 32.13 ± 3.29 | |
| 23b | 2.82 ± 0.03 | 5.53 ± 0.38 | | | | 0.036 ± 0.001 | |
| 23c | | | | | | 0.041 ± 0.010 | |
| 23d | | | | | | 0.473 ± 0.085 | |
| 23e | | | | | | 0.460 ± 0.014 | |
| 23h | | | | | | 1.46 ± 0.04 | |
| 24b | >10 | >10 | | | >10 | | |
| 24c | 0.27 ± 0.03 | 0.71 ± 0.08 | | | | | |
| 24d | 0.23 ± 0.03 | 0.44 ± 0.19 | | | | | |
| 24e | 2.10 ± 0.17 | 3.76 ± 0.23 | | | | | |
| 24f | 2.06 ± 0.12 | 3.14 ± 0.87 | | | | | |
| 25a | >10 | | | | | >10 | |
| 25b | 0.11 ± 0.01 | | | | | 0.10 ± 0.01 | |
| 26a | >10 | >10 | | | >10 | | |
| 26b | >10 | >10 | | | | | |
| 26c | 0.70 ± 0.04 | 1.15 ± 0.22 | | | | | |
| 26d | 0.38 ± 0.02 | 0.71 ± 0.06 | | | | | |
| 26e | 4.21 ± 0.22 | 8.29 ± 0.29 | | | | | |
| 26f | 3.64 ± 0.05 | 6.86 ± 0.48 | | | | | |
| 27a | | >10 | | | | >10 | |
| 27b | | 8.96 ± 0.18 | | | | 8.49 ± 0.49 | |
| 27c | | 3.49 ± 0.15 | | | | 6.68 ± 0.55 | |
| 27d | | >10 | | | | >10 | |
| 27e | | 8.77 ± 0.10 | | | | >10 | |
| 28a | >10 | | | | | >10 | |
| 28b | >10 | | | | | >10 | |
| 28c | 0.28 ± 0.05 | | | | | 0.14 ± 0.01 | |

TABLE 1-continued

In vitro activity against human cancer cell lines and HUVEC cell, GI$_{50}$ (μM)

| Compd. No. | Lung A549 | Colorectal HCT116 | Liver Hep3B | Breast MDA-MB-231 | Prostate PC3 | Oral KB | HUVEC |
|---|---|---|---|---|---|---|---|
| 28d | 1.16 ± 0.10 | 1.21 ± 0.13 | | | 2.33 ± 0.04 | | |
| 29a | >10 | | | | >10 | | |
| 29b | >10 | >10 | | | >10 | | |
| 30a | >10 | | | | >10 | | |
| 30b | >10 | | | | >10 | | |
| 30c | 0.51 ± 0.09 | | | | 0.46 ± 0.13 | | |
| 31a | >10 | | | | >10 | | |
| 31b | 8.70 ± 0.25 | >10 | | | 8.93 ± 0.25 | | |
| 31c | 3.70 ± 0.17 | | | | 2.40 ± 0.27 | | |
| 32a | >10 | | | | >10 | | |
| 32c | 5.67 ± 0.06 | 5.99 ± 0.30 | | | 6.30 ± 0.30 | | |
| 33a | | 5.79 ± 0.11 | | | 7.66 ± 0.42 | | |
| 33b | | 5.38 ± 0.10 | | | 6.01 ± 0.41 | | |
| 33c | | 6.51 ± 0.09 | | | 8.50 ± 0.45 | | |
| 33d | | 5.71 ± 0.12 | | | 8.18 ± 0.46 | | |
| 34a | >10 | | | | | | |
| 34b | 0.21 ± 0.01 | | | | | | |
| 35a | | | | | | 0.265 ± 0.021 | |
| 35b | | | | | | 0.080 ± 0.014 | |

Several tested compounds and two reference HSP90 inhibitors, namely, BIIBO21 and Tanespimycin (i.e., 17-AAG), were evaluated using the above-described HSP90 ATP-binding assay and SRB assay.

Among the tested compounds, compounds 18b, 19b, 20b, 20c, and 20 g showed high antiproliferative activity against lung A549, colon HCT116, liver Hep3B, breast MDA-MB-231 cancer cell lines as shown in Table 2 below. These five compounds all exhibited better HSP90 enzyme inhibition activity than 17-AAG and better cellular activity against A549 cell line than BIIBO21. Unexpectedly, compound 18b displayed a 4-fold improvement of antiproliferative activity as compared to that of 17-AAG in HCT116. Further, compound 18b exhibited a high safety margin with a therapeutic index of 12.4 (measured by GI$_{50}$ (HUVEC)/GI$_{50}$ (A549)). Compound 18b also showed high antiproliferative activity against leukemia HL60, lymphoblast MOLT4 and bone marrow K562.

TABLE 2

In vitro activity of synthetic HSP90 inhibitors

| Compound | A549 | HCT116 | Hep3B | MDA-MB-231 | HUVEC | TI$^a$ | HSP90 IC$_{50}$$^b$ (nM) |
|---|---|---|---|---|---|---|---|
| | | | GI$_{50}$ (μM) | | | | |
| 18b | 0.07 ± 0.01 | 0.09 ± 0.01 | 0.20 ± 0.03 | 0.09 ± 0.01 | 0.87 ± 0.01 | 12.4 | 110.18 ± 3.13 |
| 19b | 0.12 ± 0.01 | 0.64 ± 0.41 | nd$^c$ | nd | nd | nd | 109.23 ± 5.35 |
| 20b | 0.17 ± 0.01 | 1.00 ± 0.49 | 0.18 ± 0.04 | 0.07 ± 0.01 | 0.57 ± 0.02 | 3.4 | 115.39 ± 10.66 |
| 20c | 0.11 ± 0.01 | 0.37 ± 0.05 | nd | nd | nd | nd | 117.34 ± 9.62 |
| 20g | 0.28 ± 0.02 | 0.70 ± 0.06 | 0.57 ± 0.32 | 0.10 ± 0.02 | 0.82 ± 0.03 | 2.9 | 105.54 ± 7.58 |
| 17-AAG | 0.08 ± 0.01 | 0.34 ± 0.06 | nd | nd | nd | nd | 141.62 ± 12.75 |
| BIIB021 | 0.26 ± 0.03 | 0.25 | nd | nd | nd | nd | nd |

Antiproliferative activity against cancer cell

| Compound | HL60 | MOLT4 | K562 |
|---|---|---|---|
| | | IC$^{50}$ (μM, MTT) | |
| 18b | 0.24 ± 0.04 | 0.19 ± 0.01 | 0.13 ± 0.09 |

TI$^a$ Therapeutic Index measured by GI$_{50}$(HUVEC)/GI$_{50}$(A549);

HSP90 IC$_{50}$$^b$ enzyme inhibition;

nd$^c$ no data.

To confirm the inhibition of HSP90, western blotting analysis was performed to evaluate the levels HSP90 client proteins, i.e., EGFR, Akt, CDK-4, and HSP70, in HCT-116 tumor cells treated with compounds 18b, 20b, and 20 g. Total cellular extracts were obtained 24 hours after treatment. It was observed that all tested compounds were effective, causing substantial depletion of the examined client proteins and inducing an increase in the expression levels of the chaperone HSP70, which confirmed the inhibition of HSP90.

These results indicate that compounds of formula (I) have high activity in inhibiting HSP90.

Example 3: In Vivo Efficacy of Compounds of Formula (I)

An in vivo study was conducted to evaluate the efficacy of compounds of formula (I) in suppressing tumor growth in a human colon HCT116 xenograft model.

As shown in Table 3 below, among five tested compounds, compounds 18b and 20 g showed marked anticancer activity with tumor growth inhibition (TGI) values of 74.3% and 83.9%, respectively, via oral administration (100 mg/kg, daily) in the human colon HCT116 xenograft model (n=7-8). Compound 20g caused 10.4% weight loss and exhibited narrower therapeutic index as compared to compound 18b. Further, compound 18b unexpectedly exhibited dose-dependent tumor growth inhibition, the highest maximum-tolerated dose (MTD) of 250 mg/kg, and a higher therapeutic index of 10, as compared to other tested compounds.

TABLE 3

Anti-tumor activity of HSP90 inhibitors in an HCT116 xenograft model (n = 7-8).

| Compound | Dosage (mg/kg) | Schedule | Route | TGI$^a$ (%) | Loss of Body | MTD$^b$ (mg/kg) | TI$^c$ |
| --- | --- | --- | --- | --- | --- | --- | --- |
| 18b | 25 | qd | po | 55.6 | 0% | 250 | 10 |
| 18b | 100 | qd | po | 74.3 | 0% | — | — |
| 19b | 100 | qd | po | 29.1 | −3.1% Day 5 | — | — |
| 20b | 100 | qd × 7/ 5 on 2 off | po | 37.7 | −8.5% Day 5 | <250 | <2.5 |
| 20c | 100 | qd × 7/ 5 on 2 off | po | 33.1 | −15.4% Day 7 | 100 | 1 |
| 20g | 100 | qd | po | 83.9 | −10.4% Day 7 | <250 | <2.5 |

TGI$^a$ Tumor growth inhibition.

MTD$^b$ Maximum Tolerated Dose.

TI$^c$ Therapeutic Index. TI is defined as the ratio of the maximum tolerated dose (MTD) to the minimum efficacious dose (MED).

Compound 18b was also evaluated via daily oral administration in the human lung NSCLC A549 cancer xenograft model. This compound unexpectedly suppressed the tumor growth with TGIs of 46.7%, 46.9%, and 50.9% at dosages of 25, 50, and 100 mg/kg, respectively, without significant body weight loss.

These results indicate that compounds of formula (I) have high in vivo efficacy in suppressing tumor growth.

Example 4: Evaluation of Pharmacokinetic Properties of Compounds of Formula (I)

A pharmacokinetic study was conducted to evaluate the pharmacokinetic properties of compounds of formula (I). Pharmacokinetics is proposed to study the absorption, the distribution, the biotrasformations and the elimination of drugs in man and animals (Rescigno A, Segre G. Drug and Tracer Kinetics. Blaisdell, Waltham (Mass) 1966).

Five compounds of formula (I), i.e., compounds 18b, 19b, 20b, 20c, and 20g, were evaluated for their pharmacokinetic profiles in rat. See Table 4 below. It was observed that compound 18b, when orally dosed at 20 mg/kg, exhibited a long half-life of about 27.7 hours, a low clearance of about 64 ml/min/kg, a high AUC of about 1310 ng/mL*hr, and a good oral bioavailability of 25%.

TABLE 4

Pharmacokinetic profiles of HSP90 inhibitors in rat.

| | IV (2 mg/kg) | | | | PO (20 mg/kg) | | | | |
|---|---|---|---|---|---|---|---|---|---|
| Compound | $T_{1/2}$ (hr) | CL (ml/min/kg) | $V_{ss}$ (l/kg) | $AUC_{(0-inf)}$ (ng/mL*hr) | $T_{1/2}$ (hr) | $C_{max}$ (ng/ml) | $T_{max}$ (hr) | $AUC_{(0-inf)}$ (ng/mL*hr) | F (%) |
| 18b | 4.0 ± 1.7 | 64 ± 1.8 | 5.5 ± 1.1 | 520 ± 14 | 27.7 ± 13 | 40 ± 13 | 6 ± 2 | 1310 ± 252 | 25 |
| 19b | 8.1 ± 4.7 | 75 ± 4.8 | 12.0 ± 8.9 | 442 ± 49 | 11 ± 7.6 | 51 ± 9 | 0.3 ± 0.1 | 485 ± 103 | 11 |
| 20b | 1.3 ± 0.3 | 237 ± 37 | 18.0 ± 4.5 | 142 ± 25 | 7.5 ± 1.3 | 82 ± 34 | 2.2 ± 1.8 | 533 ± 154 | 37 |
| 20c | 1.5 ± 0.5 | 170 ± 64 | 9.0 ± 2.8 | 234 ± 114 | 5.9 ± 1.6 | 67 ± 23 | 2.7 ± 1.2 | 499 ± 38 | 22 |
| 20g | 0.7 ± 0.1 | 117 ± 23 | 4.3 ± 1.3 | 288 ± 59 | 2.2 ± 0.6 | 12.8 ± 8.3 | 0.5 ± 0.4 | 36 ± 5 | 1.3 |

These results indicate that compounds of formula (I) have excellent pharmacokinetic properties suitable for oral administration.

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, and in embodiments or examples of the present invention, any of the terms "comprising", "consisting essentially of", and "consisting of" may be replaced with either of the other two terms in the specification. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A compound of formula (I):

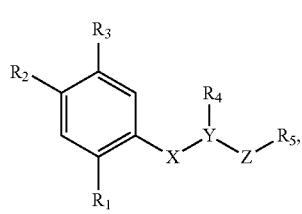

wherein
X is CO;
Y is N;
Z is phenyl, and $R_5$ is $CF_3$, CN, $NO_2$, $NR_6R_7$, —NHCO$(CH_2)_n$CONHOH, —CONH$(CH_2)_n$CONHOH, CONHOH, $CO_2NH_2$, $C_{1-6}$ alkoxyl, $C_{3-10}$ cycloalkyl, aryl, or heteroaryl; or
Z is selected from

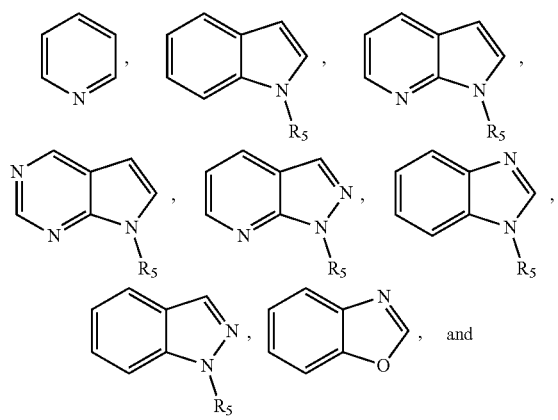

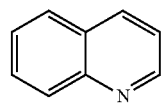

and $R_5$ is H, halogen, $CF_3$, CN, $NO_2$, $NR_6R_7$, —NHCO$(CH_2)_n$CONHOH, —CONH$(CH_2)_n$CONHOH, CONHOH, $CO_2NH_2$, $CH_2NR_6R_7$, $C_{1-6}$ alkyl, $C_{1-6}$ alkoxyl, $C_{3-10}$ cycloalkyl, $C_{3-10}$ heterocycloalkyl, aryl, or heteroaryl;

each of $R_1$ and $R_2$, independently, is OH or $NH_2$;

$R_3$ is $C_{1-6}$ alkyl or halogen; and $R_4$ is $C_{1-6}$ alkyl, $C_{3-8}$ cycloalkyl, $C_{1-6}$ alkylamine, or $C_{1-6}$ alkyl alcohol;

in which each of $R_6$ and $R_7$, independently, is H, $C_{1-6}$ alkyl, $C_{1-6}$ alkoxyl, $C_{3-10}$ cycloalkyl, $C_{3-10}$ heterocycloalkyl, aryl, or heteroaryl; or $R_6$, together with $R_7$ and the nitrogen atom bonded to $R_6$ and $R_7$, is $C_{3-10}$ heterocycloalkyl; or $R_6$, together with Z and the nitrogen atom bonded to $R_6$ and $R_7$, forms a fused bicycle; and n is 5 to 7.

2. The compound of claim 1, wherein each of $R_1$ and $R_2$ is OH and $R_3$ is isopropyl.

3. The compound of claim 1, wherein Z is phenyl and $R_5$ is —NHCO$(CH_2)_n$CONHOH or —CONH$(CH_2)_n$CONHOH, or Z is

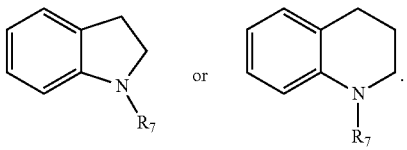

4. The compound of claim 1, wherein Z is selected from

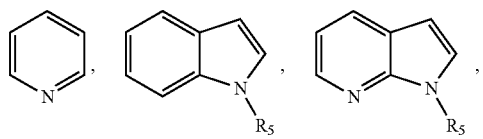

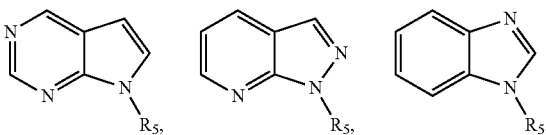

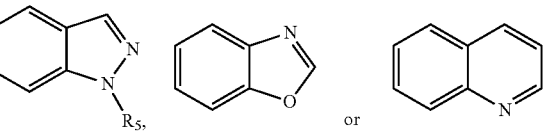

5. The compound of claim 3, wherein Z is phenyl and $R_5$ is —NHCO$(CH_2)_n$CONHOH or —CONH$(CH_2)_n$CONHOH.

6. The compound of claim 3, wherein Z is
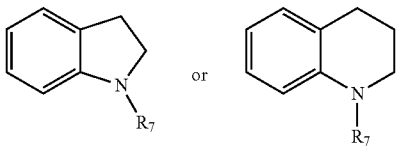
and R$_7$ is C$_{1-6}$ alkyl.
7. The compound of claim 4, wherein Z is
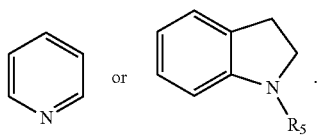
8. The compound of claim 7, wherein Z is
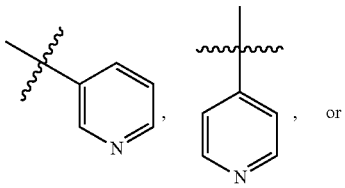
and R$_4$ is C$_{1-6}$ alkyl.
9. The compound of claim 8, wherein the compound is one of the following compounds:
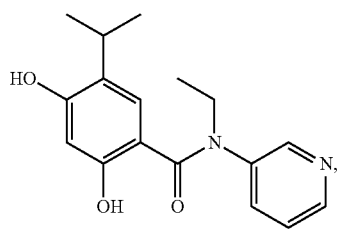 [SMILES: CCN(C(=O)c1cc(C(C)C)c(O)cc1O)c1cccnc1]
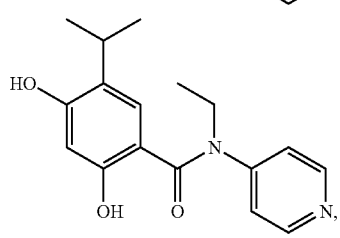
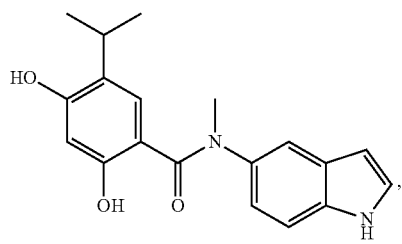
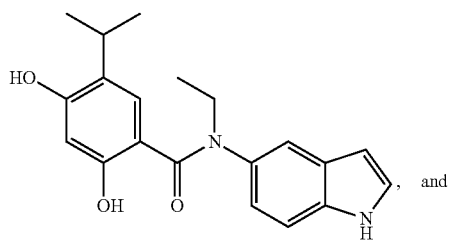, and
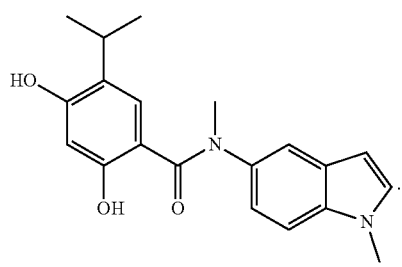
10. The compound of claim 1, wherein Z is selected from
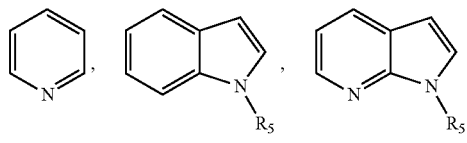
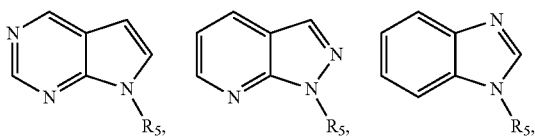
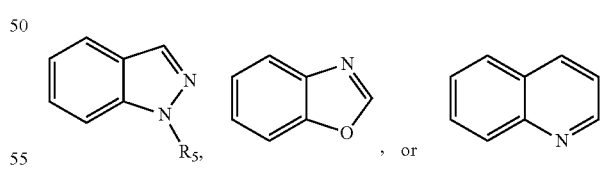
11. The compound of claim 10, wherein Z is
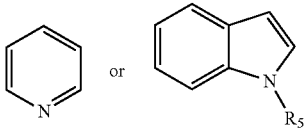

12. The compound of claim 11, wherein Z is

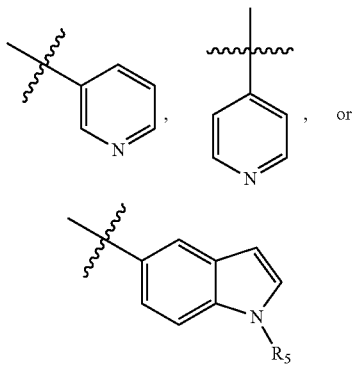

and R$_4$ is C$_{1-6}$ alkyl.

13. A pharmaceutical composition comprising a compound of claim 1 and a pharmaceutically acceptable carrier.

14. A method of treating breast cancer, non-small cell lung cancer, gastric cancer, lymphoma, or multiple myeloma, the method comprising administering to a subject in need thereof an effective amount of a compound of formula (I):

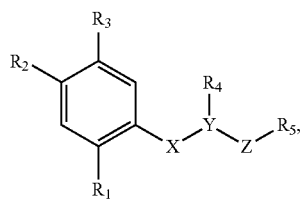

wherein

X is CO;

Y is N;

Z is phenyl, and R$_5$ is CF$_3$, CN, NO$_2$, NR$_6$R$_7$, —NHCO(CH$_2$)$_n$CONHOH, —CONH(CH$_2$)$_n$CONHOH, CONHOH, CO$_2$NH$_2$, C$_{1-6}$ alkoxyl, C$_{3-10}$ cycloalkyl, aryl, or heteroaryl; or Z is selected from

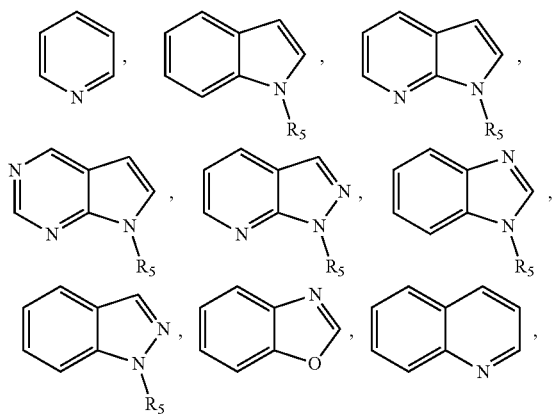

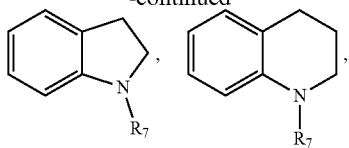

and R$_5$ is H, halogen, CF$_3$, CN, NO$_2$, NR$_6$R$_7$, —NHCO(CH$_2$)$_n$CONHOH, —CONH(CH$_2$)$_n$CONHOH, CONHOH, CO$_2$NH$_2$, CH$_2$NR$_6$R$_7$, C$_{1-6}$ alkyl, C$_{1-6}$ alkoxyl, C$_{3-10}$ cycloalkyl, C$_{3-10}$ heterocycloalkyl, aryl, or heteroaryl;

each of R$_1$ and R$_2$, independently, is OH or NH$_2$;

R$_3$ is C$_{1-6}$ alkyl or halogen; and

R$_4$ is C$_{1-6}$ alkyl, C$_{3-8}$ cycloalkyl, C$_{1-6}$ alkylamine, or C$_{1-6}$ alkylalcohol;

in which each of R$_6$ and R$_7$, independently, is H, C$_{1-6}$ alkyl, C$_{1-6}$ alkoxyl, C$_{3-10}$ cycloalkyl, C$_{3-10}$ heterocycloalkyl, aryl, or heteroaryl; or R$_6$, together with R$_7$ and the nitrogen atom bonded to R$_6$ and R$_7$, is C$_{3-10}$ heterocycloalkyl; or R$_6$, together with Z and the nitrogen atom bonded to R$_6$ and R$_7$, forms a fused bicycle; and n is 5 to 7.

15. The method of claim 14, wherein each of R$_1$ and R$_2$ is OH, and R$_3$ is isopropyl.

16. The method of claim 15, wherein Z is heteroaryl selected from the group consisting of

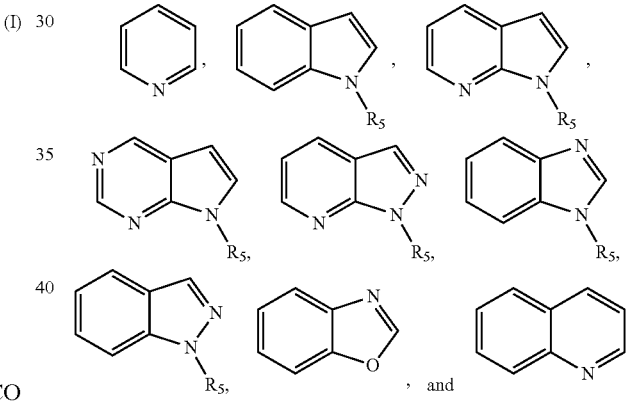

17. The method of claim 16, wherein the compound is one of the following compounds:

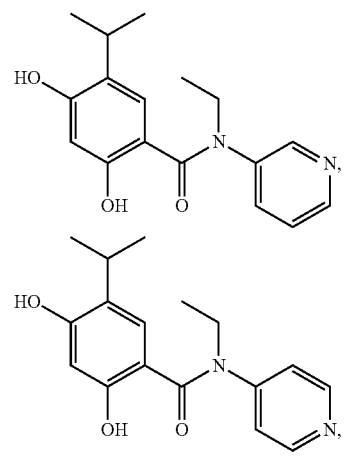

117
-continued
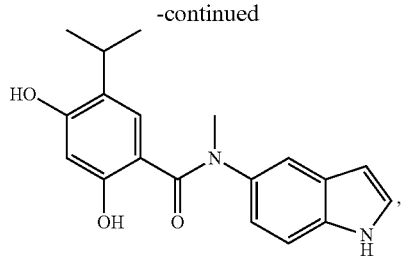
118
-continued
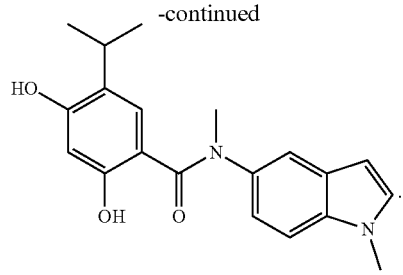
18. The method of claim 17, wherein the compound is
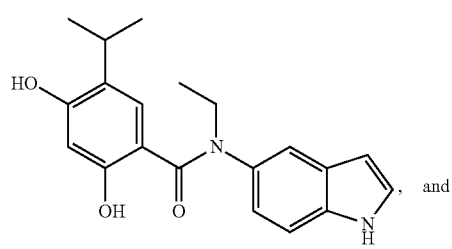, and
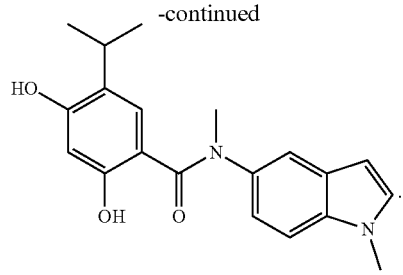
19. The method of claim 14, wherein the compound is administered orally.
* * * * *